US012625065B2

(12) United States Patent
Marrinucci et al.

(10) Patent No.: US 12,625,065 B2
(45) Date of Patent: May 12, 2026

(54) SYSTEMS AND METHODS FOR MULTIANALYTE DETECTION

(71) Applicant: Truvian Sciences, Inc., San Diego, CA (US)

(72) Inventors: Dena C. Marrinucci, San Diego, CA (US); Randal L. Erman, San Marcos, CA (US); Bala S. Manian, San Diego, CA (US)

(73) Assignee: Truvian Sciences, Inc., San Diego, CA (US)

( * ) Notice: Subject to any disclaimer, the term of this patent is extended or adjusted under 35 U.S.C. 154(b) by 591 days.

(21) Appl. No.: 17/968,674

(22) Filed: Oct. 18, 2022

(65) Prior Publication Data

US 2023/0228674 A1 Jul. 20, 2023

Related U.S. Application Data

(63) Continuation of application No. 16/082,878, filed as application No. PCT/US2017/023784 on Mar. 23, 2017, now abandoned.

(Continued)

(51) Int. Cl.
*G01N 21/64* (2006.01)
*B01L 3/00* (2006.01)
(Continued)

(52) U.S. Cl.
CPC .......... *G01N 21/253* (2013.01); *B01L 3/5085* (2013.01); *B01L 3/545* (2013.01);
(Continued)

(58) Field of Classification Search
None
See application file for complete search history.

(56) References Cited

U.S. PATENT DOCUMENTS 4,042,462 A 8/1977 Johnson et al.
4,042,463 A 8/1977 Haque et al.
(Continued)

FOREIGN PATENT DOCUMENTS

WO WO-9533986 A1 12/1995
WO WO-2009093838 A9 9/2010
(Continued)

OTHER PUBLICATIONS

US 7,833,478 B2, 11/2010, Andersson et al. (withdrawn)
(Continued)

*Primary Examiner* — Neil N Turk
(74) *Attorney, Agent, or Firm* — Snell & Wilmer, L.L.P.; April Wurster

(57) ABSTRACT

Provided herein are systems, devices and methods for performing multianalyte detection in a biological sample, such as a human blood sample. Multiwell plates useful for performing multianalyte detection are also provided. The systems, devices and methods provided herein relate to the field of direct-to-consumer diagnostics (DTC diagnostics) and are useful, e.g., for facilitating consumer access to consumer healthcare and consumer wellness information. Other uses of the systems, devices and methods provided herein relate to the fields of medical research and drug discovery.

1 Claim, 40 Drawing Sheets

Related U.S. Application Data

(60) Provisional application No. 62/312,191, filed on Mar. 23, 2016.

(51) Int. Cl.

| | |
|---|---|
| *G01N 21/25* | (2006.01) |
| *G01N 33/53* | (2006.01) |
| G01N 21/17 | (2006.01) |

(52) U.S. Cl.
CPC ..... *G01N 21/6452* (2013.01); *G01N 21/6454* (2013.01); *G01N 21/6456* (2013.01); *G01N 33/5304* (2013.01); *B01L 2200/028* (2013.01); *B01L 2300/0681* (2013.01); *B01L 2300/0803* (2013.01); *B01L 2300/0829* (2013.01); *G01N 2021/1738* (2013.01); *G01N 2021/6471* (2013.01)

(56) References Cited

U.S. PATENT DOCUMENTS

| | | | |
|---|---|---|---|
| 4,656,009 A | 4/1987 | Benajam | |
| 4,911,642 A | 3/1990 | Knowles | |
| 5,693,233 A | 12/1997 | Schembri | |
| 6,143,248 A | 11/2000 | Kellogg et al. | |
| 6,235,531 B1 | 5/2001 | Kopf-Sill et al. | |
| 6,302,134 B1 | 10/2001 | Kellogg et al. | |
| 6,399,361 B2 | 6/2002 | Brotherston et al. | |
| 6,548,788 B2 | 4/2003 | Kellogg et al. | |
| 6,582,662 B1 | 6/2003 | Kellogg et al. | |
| 6,632,399 B1 | 10/2003 | Kellogg et al. | |
| 6,752,961 B2 | 6/2004 | Kopf-Sill et al. | |
| 6,811,755 B2 | 11/2004 | McLuen et al. | |
| 6,818,435 B2 | 11/2004 | Carvalho et al. | |
| 7,094,354 B2 | 8/2006 | Pugia et al. | |
| 7,238,538 B2 | 7/2007 | Freitag et al. | |
| 7,790,110 B2 | 9/2010 | Cho et al. | |
| 7,881,262 B2 | 2/2011 | Shousterman | |
| 7,947,186 B2 | 5/2011 | Soares et al. | |
| 7,998,411 B2 | 8/2011 | Kopf-Sill et al. | |
| 8,119,393 B2 | 2/2012 | Qinwei | |
| 8,221,701 B2 | 7/2012 | Cho et al. | |
| D672,050 S | 12/2012 | Lee et al. | |
| 8,372,357 B2 | 2/2013 | Andersson et al. | |
| 8,731,721 B2 | 5/2014 | Heiner et al. | |
| 8,932,538 B2 | 1/2015 | Kim et al. | |
| 8,945,914 B1 | 2/2015 | Schaff et al. | |
| 8,962,346 B2 | 2/2015 | Schaff et al. | |
| 8,969,070 B2 | 3/2015 | Yoo | |
| 9,108,198 B2 | 8/2015 | Kim et al. | |
| 9,164,091 B2 | 10/2015 | Kim | |
| 9,186,668 B1 | 11/2015 | Schaff et al. | |
| 9,186,672 B2 | 11/2015 | Amasia et al. | |
| 9,213,040 B2 | 12/2015 | Hwang et al. | |
| 9,244,065 B1 | 1/2016 | Schaff et al. | |
| 9,279,818 B2 | 3/2016 | Yoo | |
| 9,304,129 B2 | 4/2016 | Schaff et al. | |
| 9,410,127 B2 | 8/2016 | Kim et al. | |
| 9,421,541 B2 | 8/2016 | Moon et al. | |
| 9,500,579 B1 | 11/2016 | Sommer et al. | |
| 9,616,424 B2 | 4/2017 | Lee et al. | |
| 9,624,474 B2 | 4/2017 | Park | |
| 9,625,916 B2 | 4/2017 | Garcia Da Fonseca et al. | |
| 9,726,685 B2 | 8/2017 | Lee et al. | |
| 9,737,889 B2 | 8/2017 | Moon et al. | |
| 9,816,987 B2 | 11/2017 | Mehra et al. | |
| 9,829,426 B2 | 11/2017 | Lee et al. | |
| 2002/0031833 A1 | 3/2002 | Heyneker et al. | |
| 2003/0127609 A1 | 7/2003 | El-Hage et al. | |
| 2003/0161761 A1 | 8/2003 | Williams et al. | |
| 2005/0048575 A1 | 3/2005 | Coassin et al. | |
| 2005/0123445 A1 | 6/2005 | Blecka et al. | |
| 2005/0136545 A1 | 6/2005 | Schmid et al. | |
| 2006/0160210 A1 | 7/2006 | Mori et al. | |
| 2010/0055766 A1 | 3/2010 | Hwang et al. | |
| 2011/0086778 A1 | 4/2011 | Herrmann et al. | |
| 2011/0151435 A1 | 6/2011 | Mehra et al. | |
| 2011/0189701 A1 | 8/2011 | Kim | |
| 2011/0269151 A1 | 11/2011 | Kim | |
| 2012/0028850 A1* | 2/2012 | Lee | G01N 35/00069 422/68.1 |
| 2012/0053068 A1* | 3/2012 | Remacle | C12Q 1/6851 435/6.12 |
| 2012/0142089 A1 | 6/2012 | Park | |
| 2012/0300194 A1* | 11/2012 | Zimenkov | G01J 3/4406 356/432 |
| 2013/0203634 A1 | 8/2013 | Jovanovich et al. | |
| 2013/0280748 A1* | 10/2013 | Gebetsroither | G01N 21/59 435/29 |
| 2014/0017806 A1 | 1/2014 | Lee | |
| 2014/0045168 A1* | 2/2014 | Childs | B01L 9/56 435/5 |
| 2014/0287524 A1 | 9/2014 | Lee et al. | |
| 2014/0341788 A1 | 11/2014 | Kim et al. | |
| 2015/0064774 A1 | 3/2015 | Moon et al. | |
| 2015/0090674 A1 | 4/2015 | Lee et al. | |
| 2015/0226652 A1 | 8/2015 | Jayavanth et al. | |
| 2015/0321192 A1 | 11/2015 | Lee | |
| 2015/0360225 A1 | 12/2015 | Schaff et al. | |
| 2016/0038939 A1 | 2/2016 | Min et al. | |
| 2016/0252499 A1* | 9/2016 | Wang | G01N 21/82 436/501 |
| 2017/0108438 A1* | 4/2017 | Zimenkov | G01N 21/6456 |
| 2017/0108494 A1 | 4/2017 | Mehra et al. | |
| 2017/0151559 A1 | 6/2017 | Da Fonseca et al. | |
| 2017/0176306 A1 | 6/2017 | Boehm et al. | |
| 2017/0304826 A1 | 10/2017 | Lee et al. | |
| 2017/0354970 A1 | 12/2017 | Reis et al. | |
| 2018/0038853 A1 | 2/2018 | Mehra et al. | |
| 2022/0244249 A1* | 8/2022 | Korpimäki | G01N 33/76 |

FOREIGN PATENT DOCUMENTS

| | | |
|---|---|---|
| WO | WO-2011084697 A2 | 7/2011 |
| WO | WO-2011093602 A2 | 8/2011 |
| WO | WO-2011160015 A2 | 12/2011 |
| WO | WO-2014010927 A1 | 1/2014 |
| WO | WO-2016204638 A2 | 12/2016 |
| WO | WO-2016204638 A3 | 2/2017 |
| WO | WO-2017103029 A1 | 6/2017 |
| WO | WO-2017212031 A1 | 12/2017 |
| WO | WO-2018005464 A1 | 1/2018 |

OTHER PUBLICATIONS

International Preliminary Report on Patentability for International Application No. PCT/US2017/023784, mailed Oct. 4, 2018, 9 Pages.

International Search Report and Written Opinion for International Application No. PCT/US2017/023784, mailed Jul. 27, 2017, 12 Pages.

Theranos' Elizabeth Holmes Speaks at AACC Meeting. "Theranos Science & Technology: The Miniaturization of Laboratory Testing," American Association for Clinical Chemistry [Video] [Screen captures from video retrieved on the Internet at URL: https://www.mpo-mag.com/contents/view_videos/2016-08-02/theranos-elizabeth-holmes-speaks-at-aacc-meeting/] pp. 1-6 (Aug. 2, 2016).

* cited by examiner

500a

500b

618A

619A

600a

618B

619B

600b

618C

619C

Trough

600c

700

800

900

1000

1100b

1100a

1200b

1200a

1300b

1300a

1300d

1300c

130f

130e

1300h

1300g

1300i

1300i

1300l

1300k

1300n

1300m

1300o

No Washes Required

Peaks from labeled beads

Baseline from unreacted reagent

SYSTEMS AND METHODS FOR MULTIANALYTE DETECTION

This application is a Continuation Application of U.S. patent application Ser. No. 16/082,878 filed Sep. 6, 2018, which is a US National Stage of International Application No. PCT/US2017/023784 having an international filing date of Mar. 23, 2017, which claims the benefit of priority to U.S. Provisional Application No. 62/312,191 filed Mar. 23, 2016, the entire contents of each of which are incorporated herein by reference.

1. INTRODUCTION

Provided herein are systems, devices and methods for performing multianalyte detection in a biological sample, such as a human blood sample. Multiwell plates useful for performing multianalyte detection are also provided. The systems, devices and methods provided herein relate to the field of direct-to-consumer diagnostics (DTC diagnostics) and are useful, e.g., for facilitating consumer access to consumer healthcare and consumer wellness information. Other uses of the systems, devices and methods provided herein relate to the fields of medical research and drug discovery.

2. BACKGROUND

DTC diagnostics involves consumers (e.g., patients) directly accessing healthcare or wellness-related diagnostic tests and test results, without the need for a doctor's prescription. Recently, U.S. and international DTC diagnostics markets have expanded rapidly as a result of growing consumer interest in the tracking of personalized fitness, wellness, and healthcare-related information.

A key to the success of DTC diagnostics is the availability of robust technologies for testing a broad range of diagnostically meaningful analytes with accuracy, fast turnaround times, and at low-cost. While certain handheld or portable devices, such as blood glucose meters, or test strips, e.g., for urine analysis, have been developed to facilitate personalized medical testing ("bedside testing" or point-of-care testing (POCT)") by healthcare providers, there remains a need for technologies facilitating the reliable, rapid, and cost-effective analysis of multiple analytes, e.g., at a "point-of-customer-contact (POCC)" site, such as in a pharmacy or a general store. See, e.g., Bond M. M. et al. (2015) Drop-to-Drop Variations in the Cellular Components of Fingerprick Blood. Am. J. Clin. Pathol. 144, 885-894.

3. SUMMARY

In one aspect, provided herein is a circular multiwell plate comprising a plurality of 100-500 wells, wherein the plurality of wells is organized in concentric circles around the center of the circular multiwell plate, wherein the plurality of wells is arranged in a spokes-like arrangement, and wherein the circular multiwell plate further comprises one or more troughs.

In some embodiments, the circular multiwell plate of claim 1, wherein the plurality of 100-500 wells comprises 120 or 400 wells.

In another aspect, provided herein is a multiwell plate comprising a carrier component and one or more chip components that are removable attached to the carrier component, wherein each of the one or more chip components comprises one or more pluralities of wells.

In some embodiments, wherein one or more chip component comprises two or more pluralities of different wells.

In some embodiments, all wells in one or more chip component share the same shape or the same dimensions.

In some embodiments, the multiwell plate has a circular shape.

In some embodiments, the carrier component comprises one or more troughs.

In another aspect, provided herein is a multiwell plate comprising two or more different pluralities of wells, wherein the two or more different pluralities of wells differ with respect to the wells' shape, dimension, optical properties, or surface properties.

In some embodiments, two or more different pluralities of wells are located on two or more chip components of the multiwell plate that are each independently removable from a carrier component of the multiwell plate.

In some embodiments, the shape of one or more pluralities of the two or more different pluralities of wells comprises a cylinder, a cone, a cube, or a rectangular cuboid.

In some embodiments, the multiwell plate comprises a plurality of cylindrical wells and a different plurality of rectangular cuboid wells.

In some embodiments, the dimension comprises the height, width, length, radius, diameter, or volume of a well.

In some embodiments, the multiwell plate comprises a plurality of wells comprising a diameter of between about 5.0 mm and about 7.0 mm and a different plurality of wells comprising a diameter of between about 2.0 mm and about 7.0 mm.

In some embodiments, the optical properties comprise a light transmission characteristic of a well bottom or a well wall.

In some embodiments, the multiwell plate comprises a plurality of wells comprising a well bottom that is translucent for light of a wavelength between 200 nm and 850 nm and a different plurality of wells comprising a well bottom that is opaque for light of a wavelength between 200 nm and 850 nm.

In some embodiments, the surface properties comprise a characteristic of a high-binding surface for a biomolecule or a cell.

In some embodiments, the multiwell plate comprises a plurality of wells comprising a high protein-binding well bottom or wall surface and a different plurality of wells comprising a low protein-binding well bottom or wall surface.

In some embodiments, the two or more different pluralities of wells differ with respect to assay reagent content.

In some embodiments, the multiwell plate comprises a plurality of wells comprising an assay reagent for a cell-based assay and a different plurality of wells comprising an assay reagent for a biochemical assay.

In some embodiments, the assay reagent for a cell-based assay comprises and isotonic buffer solution or cell culture medium and the assay reagent for the biochemical assay comprises an enzyme.

In some embodiments, the multiwell plate comprises a plurality of wells comprising an assay reagent for an absorbance based assay and a different plurality of wells for a fluorescence based assay.

In some embodiments, the assay reagent for the absorbance assay comprises a chromogenic enzyme substrate and the assay reagent for the fluorescence based assay comprises a fluorogenic substrate or a fluorescently labeled binding protein.

In some embodiments, the multiwell plate comprises a plurality of wells comprising an assay reagent for a homogeneous assay and a different plurality of wells for a heterogeneous assay.

In some embodiments, the assay reagent for the homogeneous assay comprises an enzyme in solution and the assay reagent for the heterogeneous assay comprises a binding protein or oligonucleotide capture probe immobilized on a well surface or on the surface of a bead in a well.

In some embodiments, one or more plurality of the two or more pluralities of wells comprises a dried assay reagent.

In some embodiments, the multiwell plate has a circular shape or a disk shape.

In some embodiments, the two or more pluralities of different wells are arranged on one or more circles of wells on the multiwell plate.

In some embodiments, the two or more pluralities of different wells are arranged on two or more concentric circles of wells on the multiwell plate.

In some embodiments, each of the two or more pluralities of different wells is arranged on a different circle of the two or more concentric circles of wells.

In some embodiments, a plurality of wells on an outer circle of wells has a greater diameter or a larger volume than a different plurality of wells on an inner circle of wells.

In some embodiments, a plurality of wells on a peripheral circle of wells comprises a translucent well bottom.

In some embodiments, the peripheral circle of wells comprises 24 wells comprising a diameter of 1.5 mm.

In some embodiments, a plurality of wells on an inner circle of wells comprise an opaque well bottom.

In some embodiments, the circular or disc shaped multiwell plate comprises a single center well.

In some embodiments, the multiwell plate comprises a barcode.

In another aspect, provided herein is a kit comprising one or more multiwell plates provided herein, and, optionally, assay reagents for two or more different assays.

In some embodiments, one or more multiwell plates are packaged in a packaging material.

In some embodiments, the packaged one or more multiwell plates are sterile.

In some embodiments, one or more assay reagents are stored in a well of the multiwell plate.

In some embodiments, one or more assay reagents are stored in a container separate from the multiwell plate.

In another aspect, provided herein is an assembly comprising a multiwell plate provided herein and a plate holder, wherein the plate holder contacts the bottom of the multiwell plate and covers the bottoms of some or all wells on the multiwell plate.

In some embodiments, one or more pluralities of the two or more different pluralities of wells comprise a translucent well bottom.

In some embodiments, the multiwell plate has a circular shape or disk shape and the two or more pluralities of different wells are arranged on two or more different concentric circles of wells.

In some embodiments, the plate holder does not cover the bottoms of wells on the peripheral circle of wells on the multiwell plate and a plurality of wells on the peripheral circle of wells comprises a translucent bottom.

In another aspect, provided herein is an assay station comprising a housing and an assembly of a multiwell plate and a plate holder provided herein.

In some embodiments, the assay station comprises a light source for light of a wavelength between 200 nm and 850 nm in the housing, wherein the light source is configured such that a light path connects the light source and the bottoms of wells on the peripheral circle of wells on the multiwell plate.

In some embodiments, the assay station comprises a detector in the housing positioned to detect light transmitted from the light source through the peripheral circle of wells on the multiwell plate.

In some embodiments, the assay station comprises a motor and a seat configured to engage the assembly and to rotate the peripheral circle of wells relative to the light source.

In some embodiments, the assay station comprises a barcode reader.

In some embodiments, provided herein is a multianalyte detection system, comprising a consumer interface, a sample processing station, an assay station and a data processing unit.

In some embodiments, the sample processing station comprises a sample dilution station and, optionally, a sample collection station.

In some embodiments, the sample processing station comprises a sample quality control station.

In some embodiments, the multianalyte detection system comprises a multiwell plate storage unit.

In some embodiments, the assay station is an assay station provided herein.

In another aspect, provided herein is a method for multianalyte detection, comprising performing two or more different assays for two or more analytes of interest in a sample from a consumer in two or more different pluralities of wells of a multiwell plate to detect the two or more different analytes.

In some embodiments, the method comprises verifying the consumer's identity.

In some embodiments, the method comprises presenting the consumer with a selection of analytes of interest for testing in the two or more different assays.

In some embodiments, the method comprises transferring the results of the two or more different assays to a data processing unit.

In some embodiments, the method comprises presenting the results of the two or more different assays to the consumer.

In some embodiments, the method comprises collecting the sample from the consumer.

In some embodiments, the method comprises performing a quality control test on the sample from the consumer, and, if the sample fails the quality control test, requesting an additional sample from the consumer.

In some embodiments, the sample from the consumer is a blood sample.

In some embodiments, the blood sample is a fingerprick blood sample.

In some embodiments, the quality control test comprises determining the drop-to-drop variation in a component of fingerprick blood.

In some embodiments, the component of fingerprick blood comprises hemoglobin concentration, total white blood cell (WBC) count, three-part WBC differential or platelet count.

In some embodiments, the quality control test fails if the coefficient of variation (CV) in two or more successive drops of finger prick blood is greater than 1%, greater than 2%, greater than 3%, greater than 4%, greater than 5%, greater than 6%, greater than 7%, greater than 8%, greater than 9%, or greater than 10%.

In some embodiments, the two or more successive drops of fingerprick blood are 2, 3, 4, 5, 6, 7, 8, 9, or 10 successive drops of fingerprick blood.

In some embodiments, the two or more different assays comprise a cell-based assay and a biochemical assay.

In some embodiments, the two or more different assays comprise a homogeneous assay and a heterogeneous assay.

In some embodiments, the two or more different assays comprise a absorbance based assay and a fluorescence based assay.

In some embodiments, the two or more different assays comprise an assay for a high abundance analyte of interest and a low abundance analyte of interest.

In some embodiments, the two or more different assays comprise an assay for a medium abundance analyte of interest.

In some embodiments, the two or more different assays comprise an assay comprising a single endpoint read at the end of an assay reaction and, optionally, a baseline read at the beginning of the assay reaction, and a different assay comprising three or more reads during the time course of an assay reaction.

In some embodiments, one or more of the two or more different assays is a mix-and-read assay started by transferring a sample aliquot to a well of the multiwell plate.

In some embodiments, the two or more different assays comprise an absorbance based cellular assay. In some embodiments, the two or more different assays comprise a homogeneous fluorescence based assay. In some embodiments, the homogeneous fluorescence based assay is a biochemical assay. In some embodiments, the homogeneous fluorescence based assay is a cell-based assay. In some embodiments, the two or more different assays comprise a heterogeneous fluorescence based assay. In some embodiments, the heterogeneous fluorescence based assay is a biochemical assay. In some embodiments, the heterogeneous fluorescence based assay is a cell-based assay.

In some embodiments, the two or more different assays comprise an absorbance based biochemical assay. In some embodiments, the two or more different assays comprise a homogeneous fluorescence based assay. In some embodiments, the homogeneous fluorescence based assay is a biochemical assay. In some embodiments, the homogeneous fluorescence based assay is a cell-based assay. In some embodiments, the two or more different assays comprise a heterogeneous fluorescence based assay. In some embodiments, the heterogeneous fluorescence based assay is a biochemical assay. In some embodiments, the heterogeneous fluorescence based assay is a cell-based assay.

In some embodiments, at least one of the two or more assays comprises a lower limit of detection between 0.1 nM and 10 nM, at least one of the two or more assays comprises a lower limit of detection between 10 nM and 1 μM, at least one of the two or more assays comprises a lower limit of detection between 1 μM and 100 μM, and at least one of the two or more assays comprises a lower limit of detection between 100 μM and 10 mM.

In some embodiments, the Z-factor for each of the two or more different assays is >0.5, >0.6, >0.7, >0.8, or >0.9.

In some embodiments, the two or more analytes comprise a pre-diabetes panel, a cholesterol/lipid analyte panel, a nutrition panel, a fertility panel, a sexually transmitted disease (STD) panel, a thyroid panel, an electrolyte panel, a complete metabolic panel (CMP) or a complete blood cell (CBC) panel of analytes.

In some embodiments, the pre-diabetes panel comprises hemoglobin A1C, fasting blood glucose, trigycleride, high-sensitivity C-reactive protein (hsCRP), cytostatin C, alanine-aminotransferase (ALT) or aspartate aminotransferase (AST).

In some embodiments, the cholesterol/lipid panel comprises total cholesterol, triglyceride, high-density lipoprotein (HDL), low-density lipoprotein (LDL), blood glucose (fasting) or hsCRP.

In some embodiments, the nutrition panel comprises iron, potassium, sodium, zinc, calcium, vitamin D, magnesium, folate or vitamin B12.

In some embodiments, the fertility panel comprises human chorionic gonadotropin (HCG), follicle-stimulating hormone (FSH), estradiol, Anti-Millerian hormone (AMH), progesterone, or prolactine (PRL).

In some embodiments, the STD panel comprises *Chlamydia trachomatis, Neisseria gonorrhoeae, Treponema* palladium, HSV-1, HSV-2, HIV, hepatitis B or hepatitis C.

In some embodiments, the thyroid panel comprises thyroid-stimulating hormone (TSH), triiodothyronine (T3) or thyroxine (T4).

In some embodiments, the electrolyte panel comprises chloride, potassium, sodium or carbon dioxide.

In some embodiments, the complete metabolic panel (CMP) comprises glucose, calcium, albumin, total protein, sodium, potassium, carbon dioxide, chloride, blood urea nitrogen (BUN), creatine, alanine aminotransferase (ALT), alkaline phophatase (ALP), aspartate aminotransferase (AST) or bilirubin.

In some embodiments, the complete blood cell (CBC) panel comprises white blood cell count (WBC), white blood cell differential (DIFF), absolute neutrophil count or percent neutrophils (Neu, PMN, polys), absolute lymphocyte count or percent lymphocytes (Lymph), absolute monocyte count or percent monocytes (Mono), absolute eosinophil count or percent eosinophils (EOS), absolute basophil count or percent basophils (BASO), red blood count (RBC), red blood cell distribution (RDW), hemoglobin (Hb), hematocrit (Hct), mean corpuscular volume (MCV), mean corpuscular hemoglobin (MCH), mean corpuscular hemoglobin concentration (MCHC), platelet count (PIT), or mean platelet volume (MPV).

In another aspect, provided herein is an integrated diagnostic apparatus for multianalyte detection in a consumer sample, comprising a chassis; a consumer interface, optionally attached to the chassis, for the consumer to enter identifying information, select a multianalyte panel, or confirm the selection of a preselected multianalyte panel to be assayed in the consumer sample; a sample collection station attached to the chassis for a consumer to deposit the consumer sample and, optionally, to analyze a sample characteristic; an assay station attached to the chassis for assaying two or more analytes from the multianalyte panel, wherein the platform is configured for the placement of a multiwell plate; a processor, and, optionally, a multiwell plate, wherein the processor is in electrical communication with the consumer interface to receive consumer identification information or multianalyte selection information, wherein the processor is optionally in electrical communication with the sample collection station to receive information confirming the presence of the sample and describing the sample characteristic, wherein the processor is optionally in electrical communication with the sample preparation station to receive a signal from the sample preparation station when the sample preparation is complete, and wherein the processor is in electrical communication with the assay station to receive the assay results.

In some embodiments, the consumer interface comprises a data entry device; a display, and, optionally, a consumer identification device.

In some embodiments, the apparatus comprises an operator interface, comprising a data entry device; a display, and, optionally, a barcode reader.

In some embodiments, the sample collection station comprises a sample collection device to receive the consumer sample; a barcode reader, and optionally, a sample verification device to confirm the presence or integrity of the sample or a consumer's compliance with protocol during sample collection.

In some embodiments, the integrated diagnostic apparatus comprises a sample preparation station attached to the chassis to prepare the consumer sample for multianalyte detection, comprising a filtration unit or centrifugation unit, and optionally, a sample dilution device.

In some embodiments, the sample preparation station or the sample collection station comprises a sample quality control station to assess sample contamination or sample variability.

In some embodiments, the assay station comprises a light source; a detector, and a platform configured for the placement of a multiwell plate.

In some embodiments, the detector comprises three detection modules arranged in a line next to one another.

In some embodiments, the three detection modules comprise a fluorescence detection module, an absorbance reader, and a cell-enumeration module.

In some embodiments, the platform configured for the placement of a multiwell plate is movably mounted on rails that are attached to the chassis, wherein the rails are arranged underneath the detector in a parallel alignment with the line of detection modules in the detector to allow the platform to move underneath the detector from a position underneath a first detection module to a position underneath a second detection module.

In some embodiments, the platform configured for the placement of a multiwell plate is rotatably mounted on the rails to allow for a multiwell plate placed on the platform to rotate underneath each of the detection modules.

In some embodiments, the processor is configured to process the assay results to determine the levels of the two or more analytes assayed in the sample.

In some embodiments, the processor is configured to communicate with an electronic device of the consumer to inform the consumer of the analyte levels or the status of the analyte levels.

In some embodiments, the electronic device of the consumer is a mobile device or a personal computer.

In some embodiments, the processor is configured to communicate with a database.

In some embodiments, the database comprises two parts, wherein the first part of the database comprises consumer identifying information and does not comprise information related to a consumer's medical records, and wherein the second part of the database comprises the consumer's medical records and does not comprise consumer identifying information.

In some embodiments, the dimensions of the apparatus are about 700 mm×600 mm×800 mm.

In some embodiments, the dimensions of the apparatus are about 400 mm×400 mm×400 mm.

In some embodiments, the sample collection device is configured to collect a sample from a consumer in the sample collection station.

In some embodiments, the sample collection station is configured to receive an aliquot of a sample collected from a consumer outside the sample collection station.

In some embodiments, the sample collection station comprises a camera configured to record sample collection from the consumer in the sample collection station or the deposition of a sample collected outside the sample collection station.

In some embodiments, the sample collection station comprises a device for measuring a sample volume.

In some embodiments, the assay station comprises a barcode reader configured to read a barcode on a multiwell plate placed on the platform in the assay station.

In some embodiments, the integrated diagnostic apparatus comprises a storage unit for two or more multiwell plates attached to the chassis.

In some embodiments, the multiwell plate comprises a barcode.

In some embodiments, the barcode encodes information related to the multiwell plate layout, analyte panels to be assayed using the multiwell plate, or multiwell plate manufacturing information.

In some embodiments, the multiwell plate comprises reagents for two or more different analyte assays in two or more different pluralities of wells.

In some embodiments, the integrated diagnostic apparatus comprises a waste disposal unit attached to the chassis.

In some embodiments, the waste disposal unit comprises a barcode reader configured to read the barcode of a multiwell plate in the waste disposal unit or a camera configured to detect a multiwell plate in the waste disposal unit.

In another aspect, provided herein is a multianalyte detection system comprising two or more integrated diagnostic apparatuses provided herein.

In some embodiments, the two or more integrated apparatuses communicate with the same database to store data from a plurality of consumers.

In some embodiments, the database comprises for at least one consumer diagnostic information for the same test collected at two or more time points.

4. BRIEF DESCRIPTION OF THE DRAWINGS

Figure 6A:
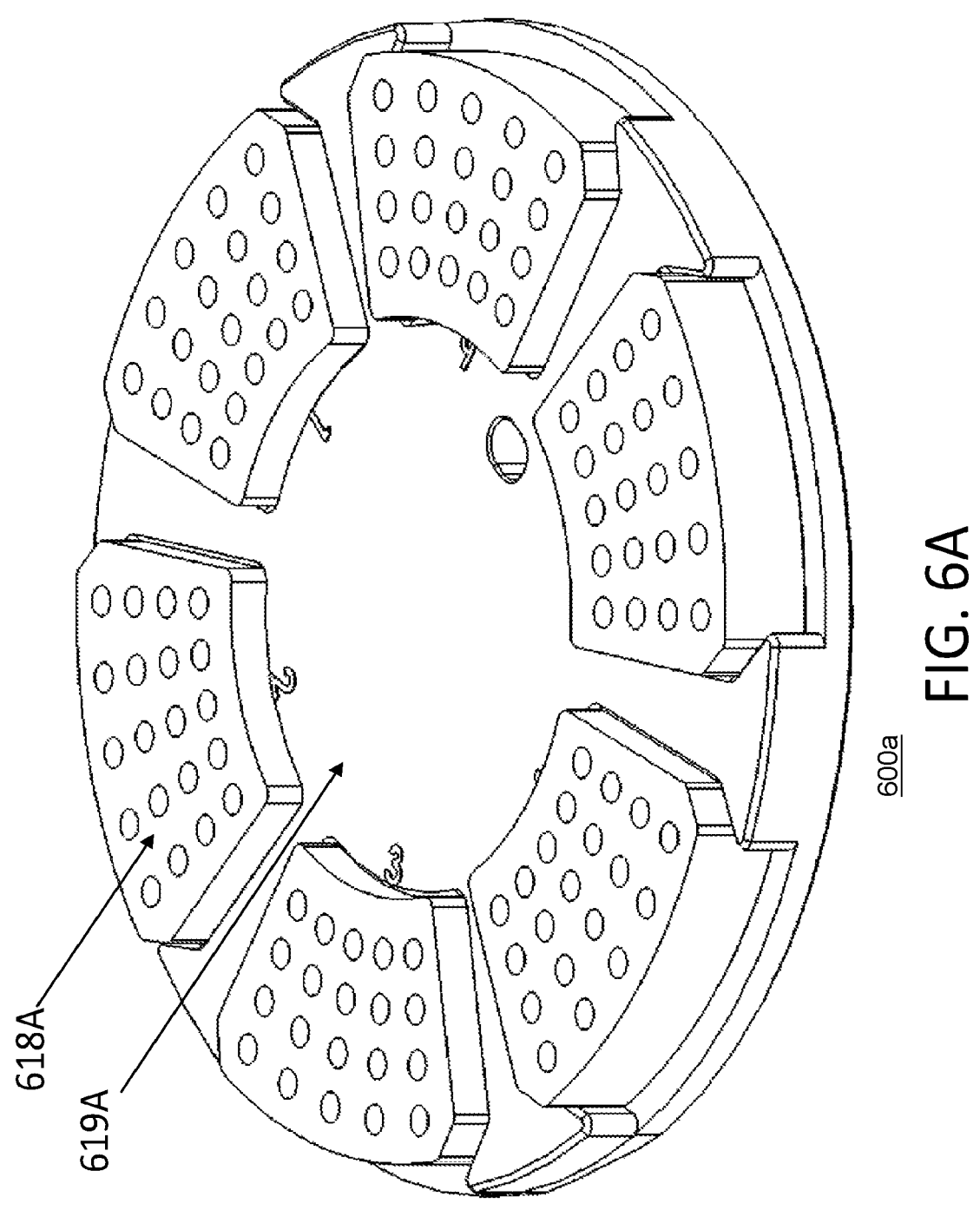
Figure 6B:
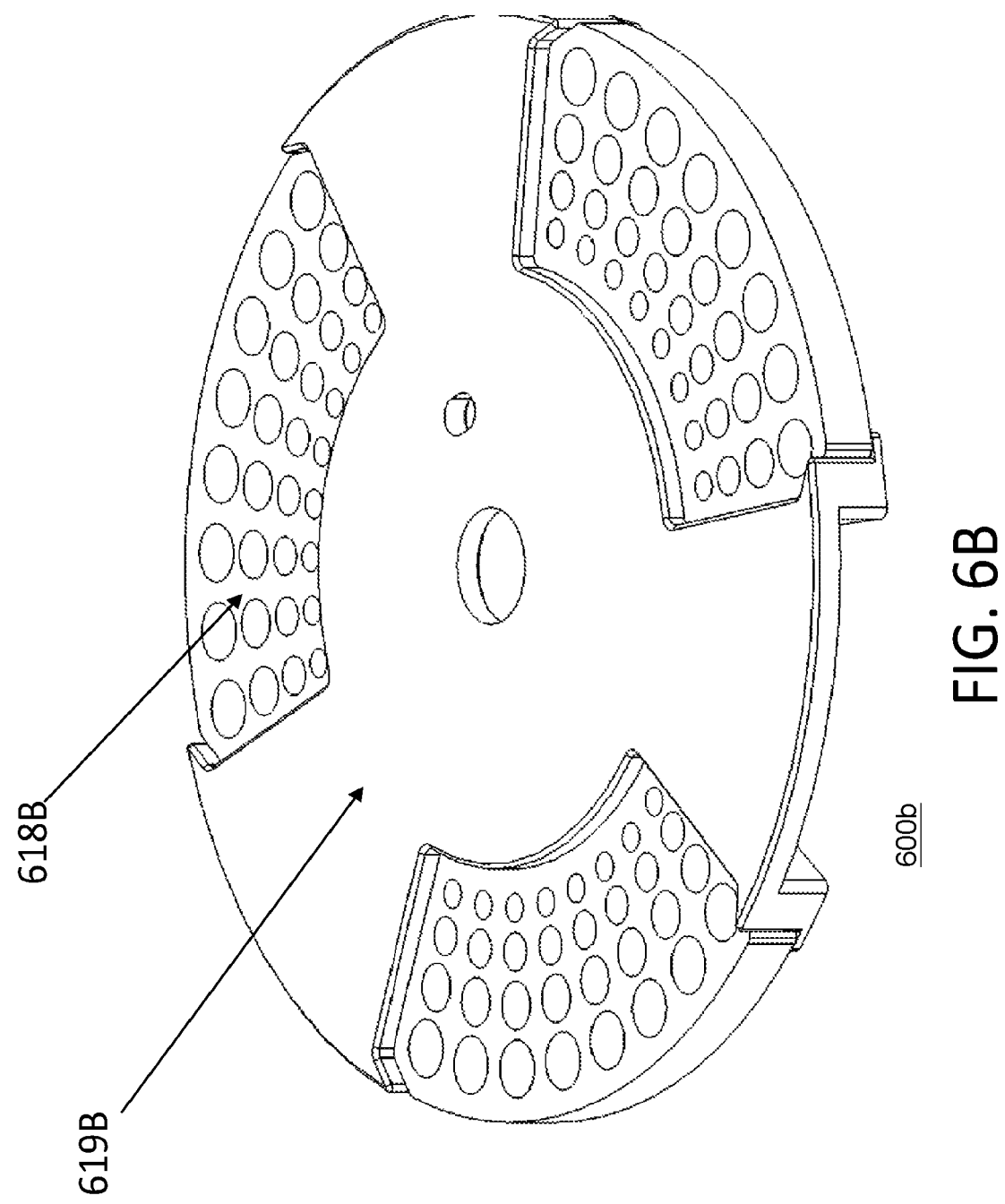
Figure 6C:
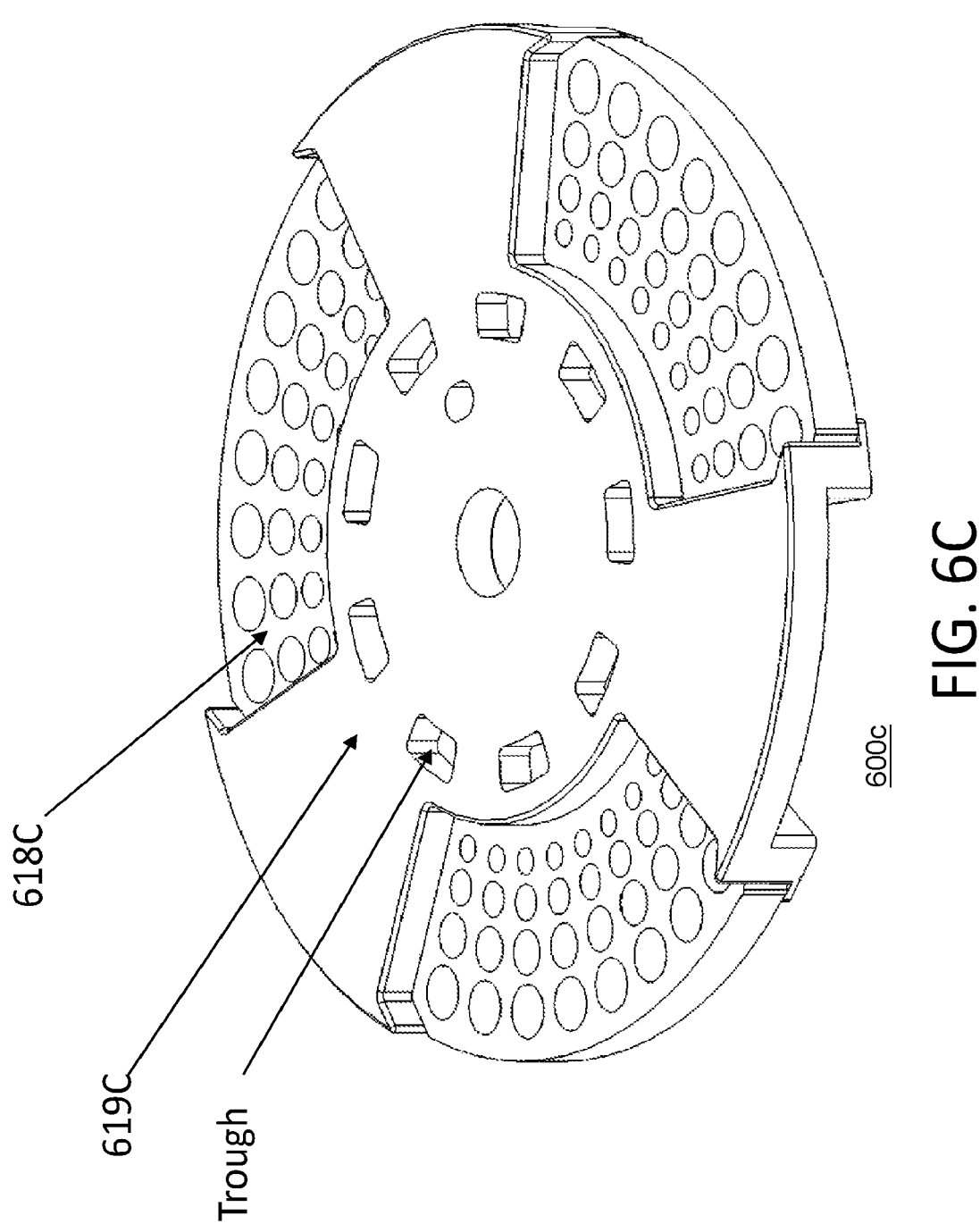
Figure 6D:
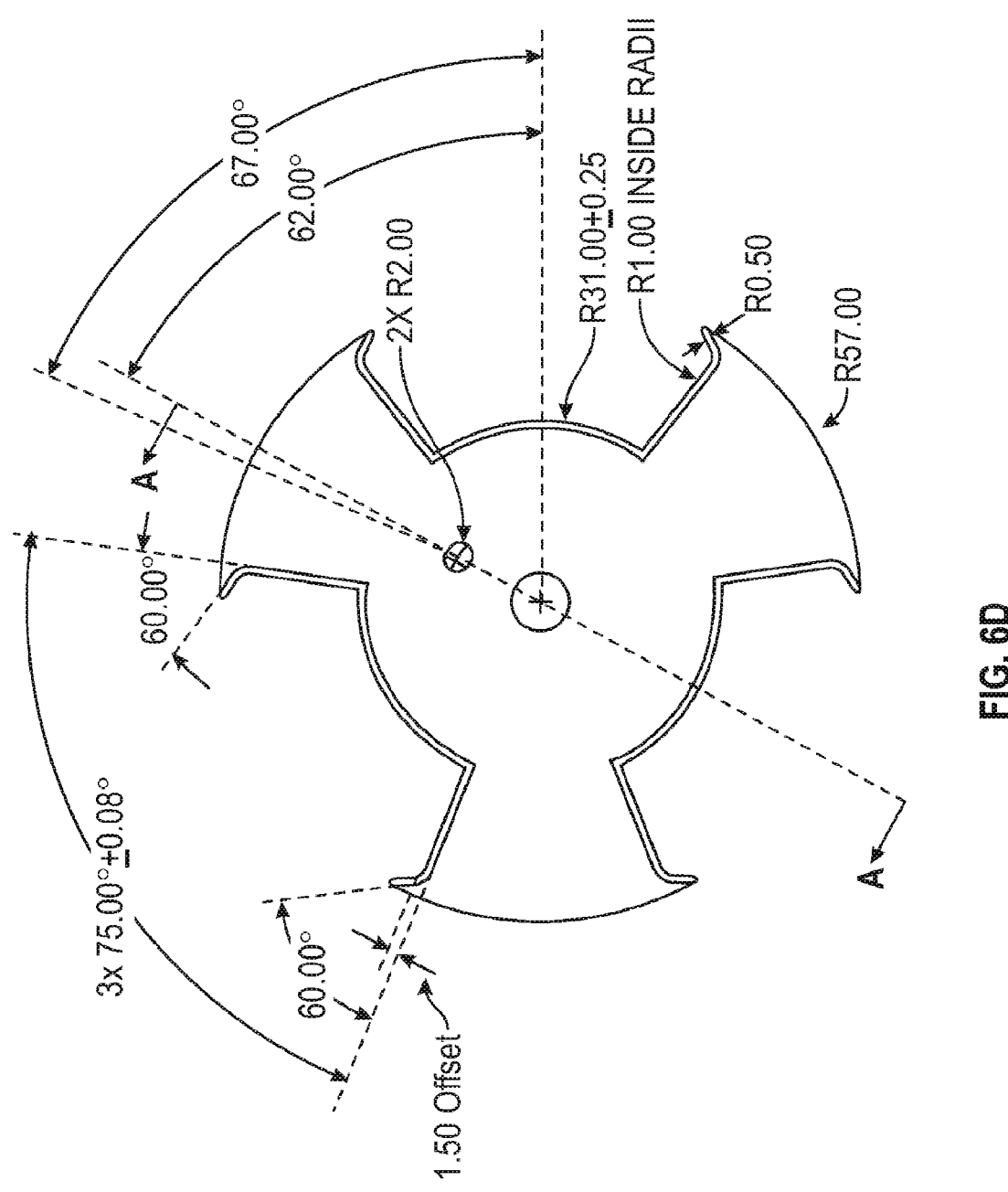
Figure 6E:
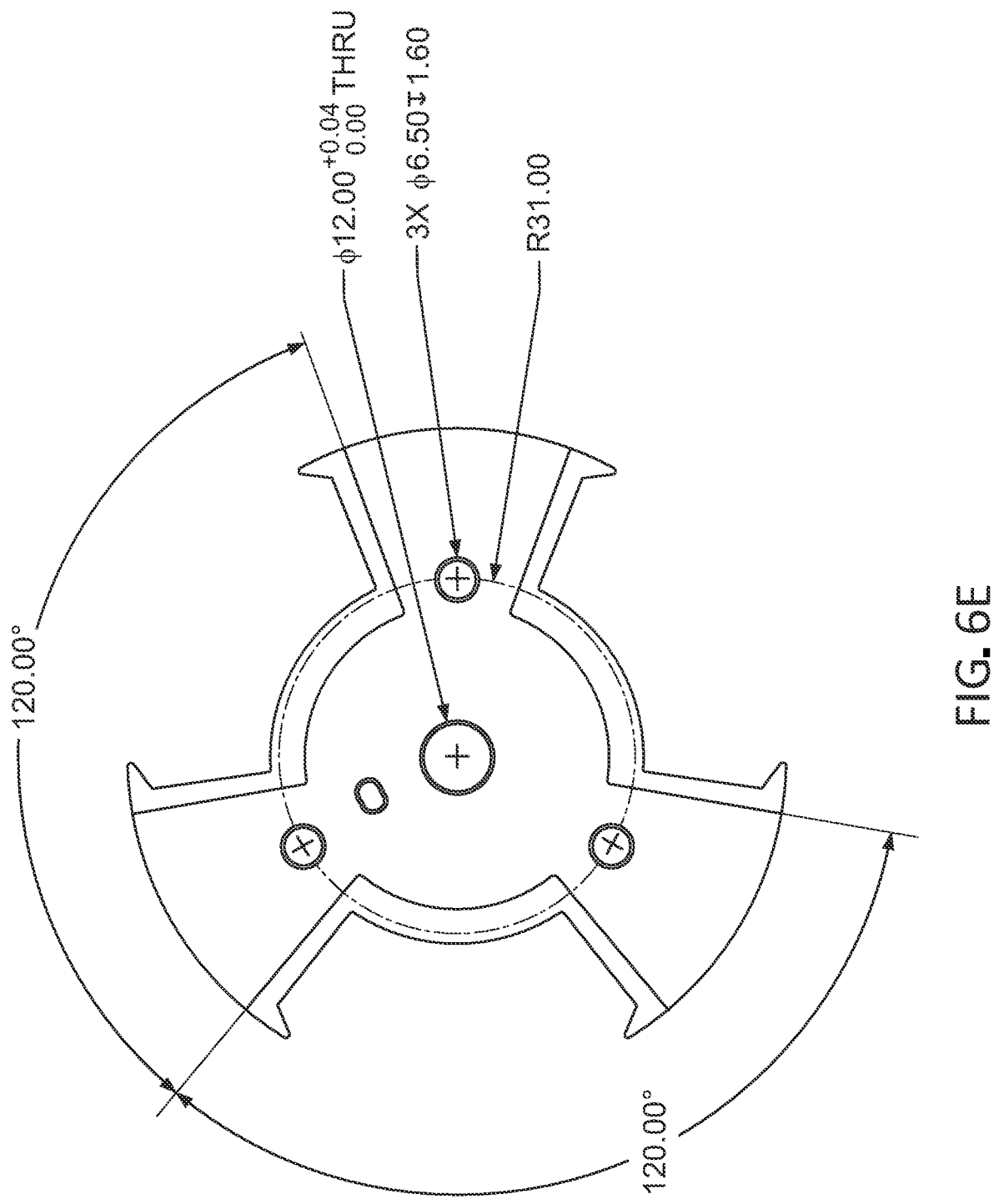
Figures 6F, 6G:
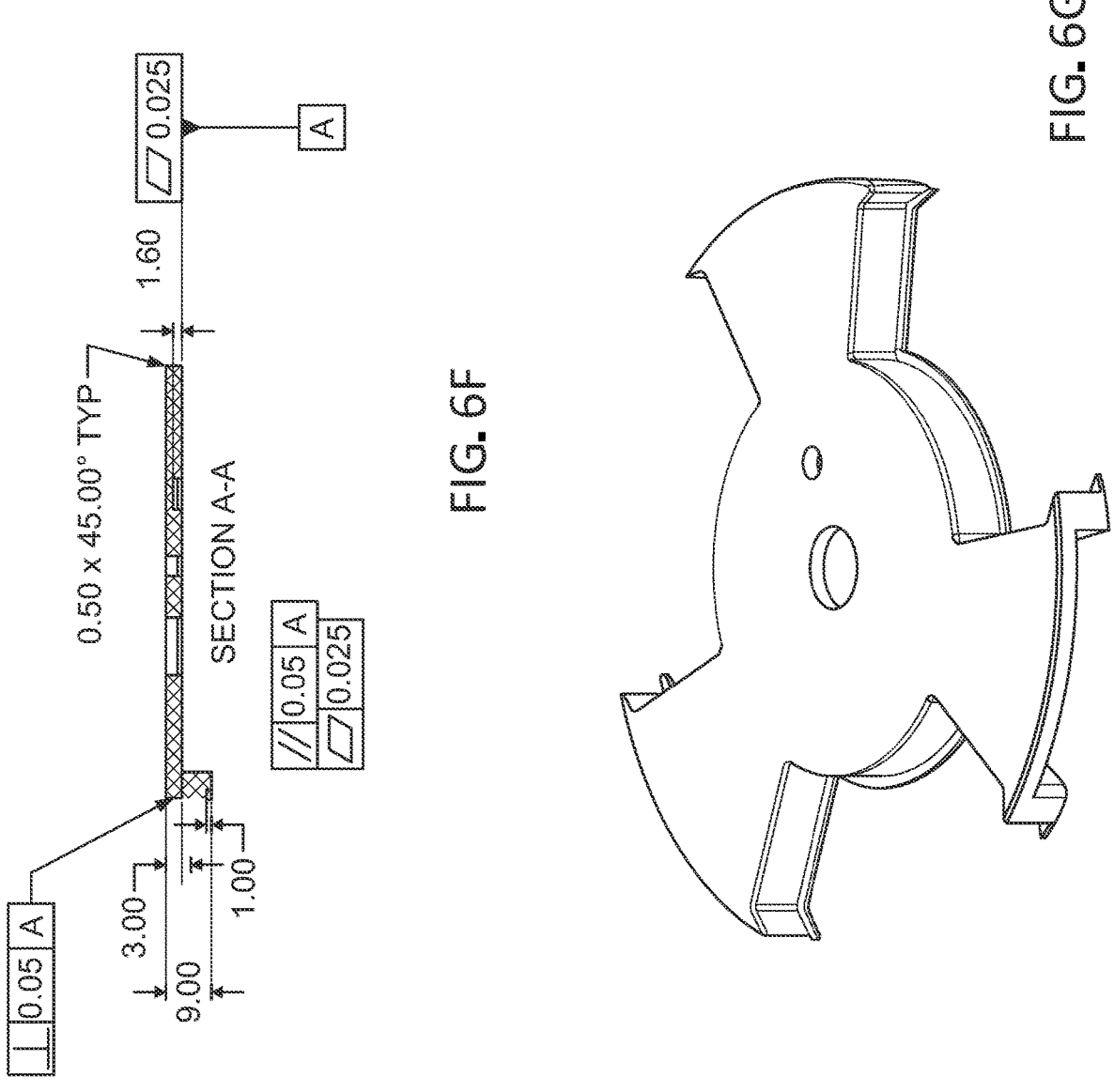

FIG. 6A, FIG. 6B, and FIG. 6C show drawings illustrating exemplary multiwell plates provided herein that each comprise a plurality of chips with assay wells and a carrier holding the plurality of chips.

FIG. 6D, FIG. 6E, FIG. 6F, and FIG. 6G. show drawings illustrating exemplary carriers of multiwell plates provided herein that are configured to hold multiwell chips with assay wells.

Figure 7:
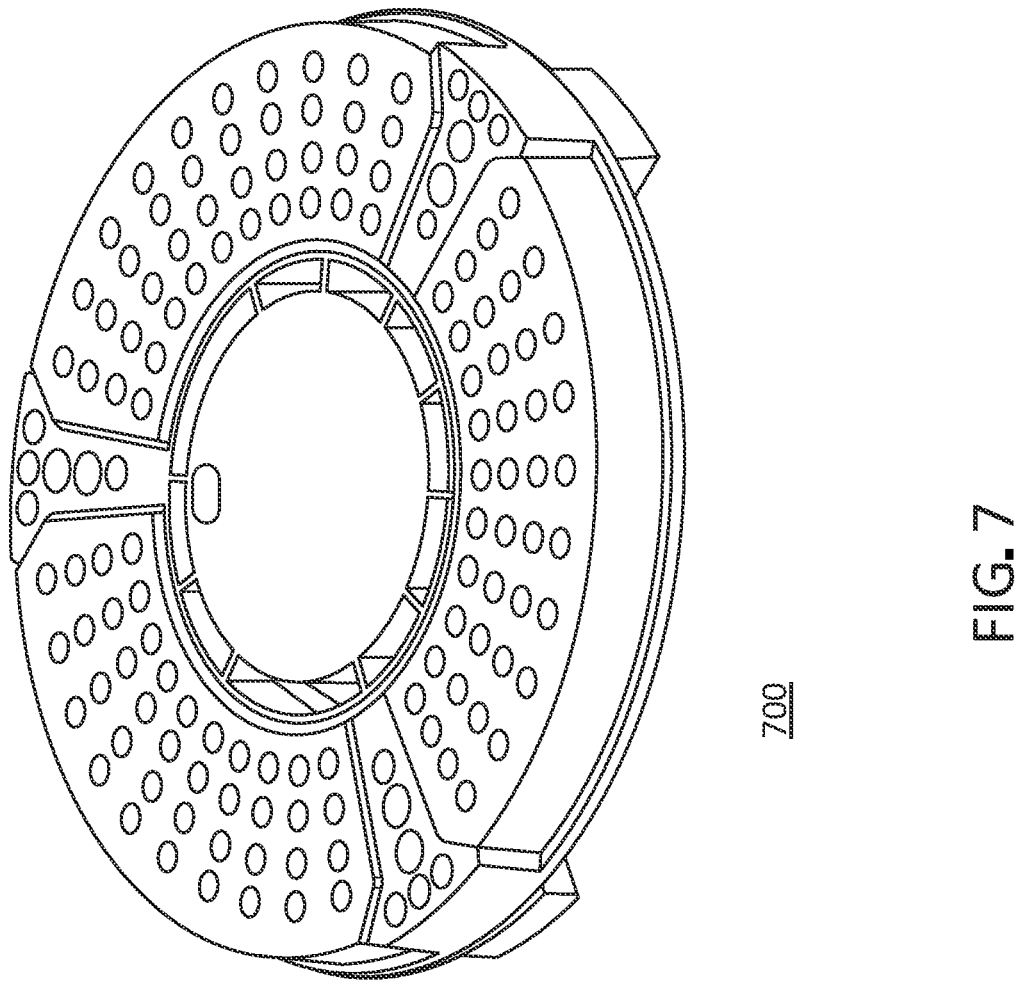

FIG. 7 shows a drawing illustrating an exemplary multi-well plate provided herein that comprises a carrier holding three chips with assay wells.

Figure 8:
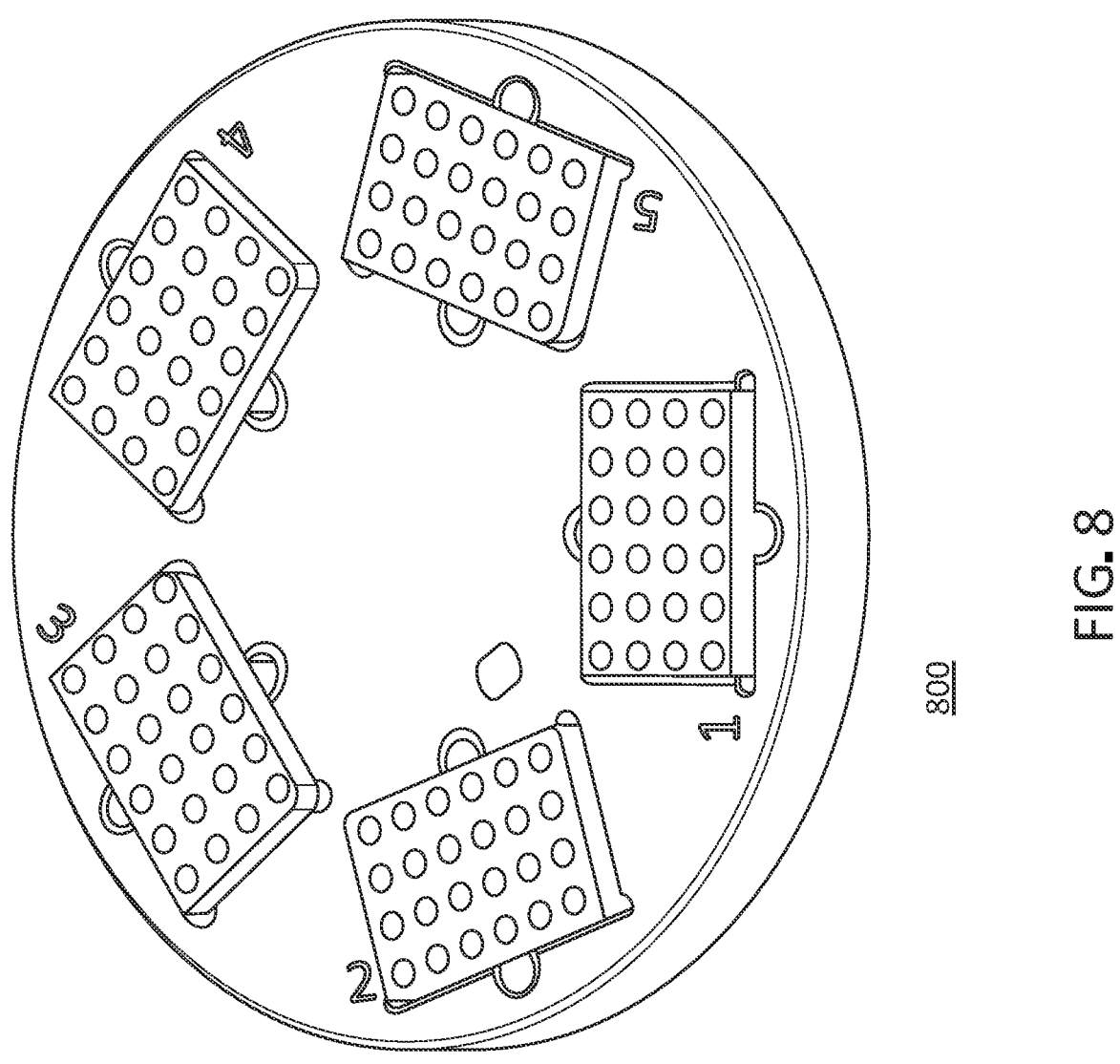

FIG. 8 shows a drawing illustrating an exemplary multi-well plate provided herein that comprises a carrier holding five multiwell chips with assay wells.

Figure 9:
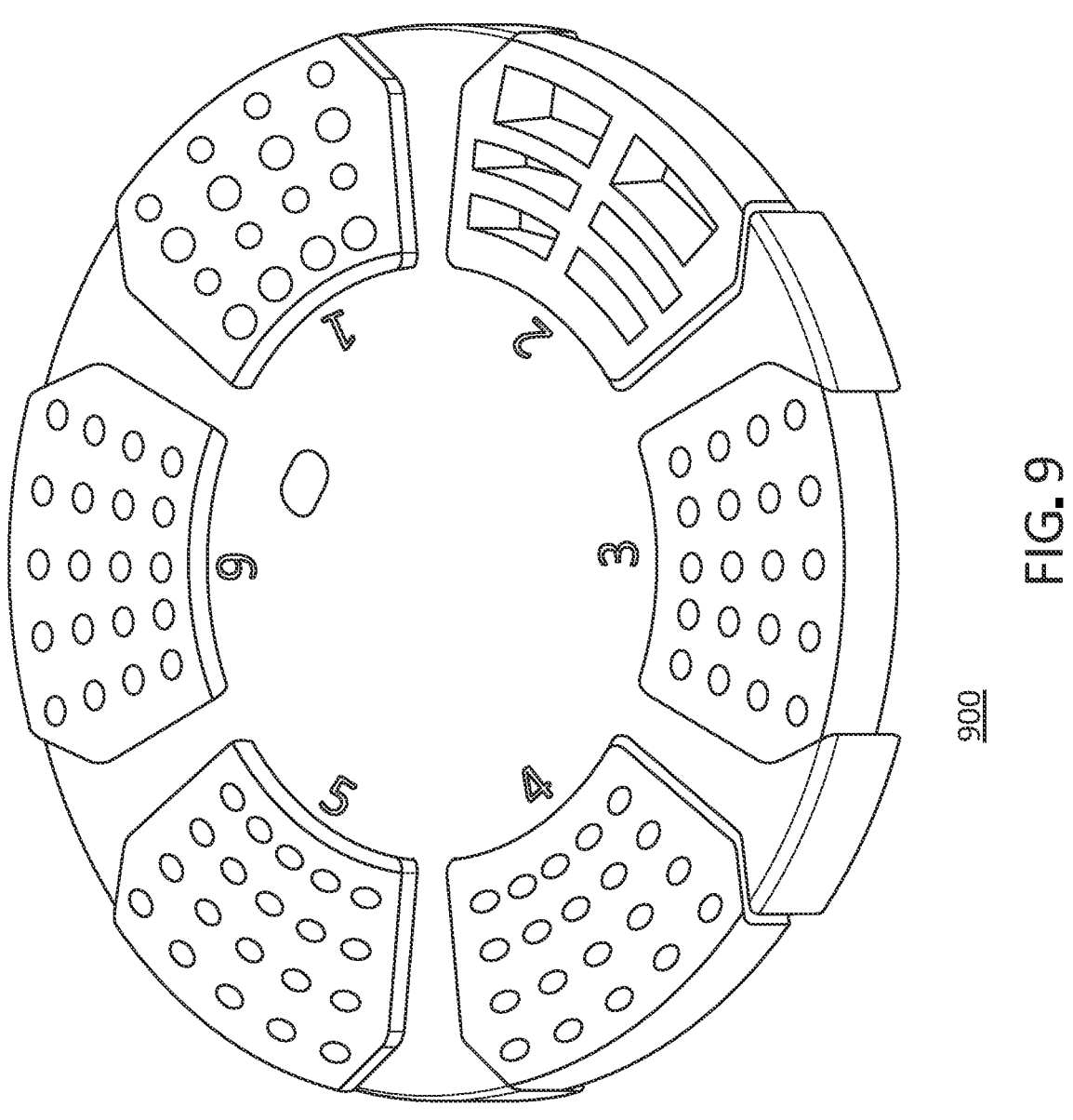

FIG. 9 shows a drawing illustrating an exemplary multi-well plate provided herein that comprises a carrier holding five multiwell chips with assay wells and a sixth multiwell chip with reagent troughs.

Figure 10:
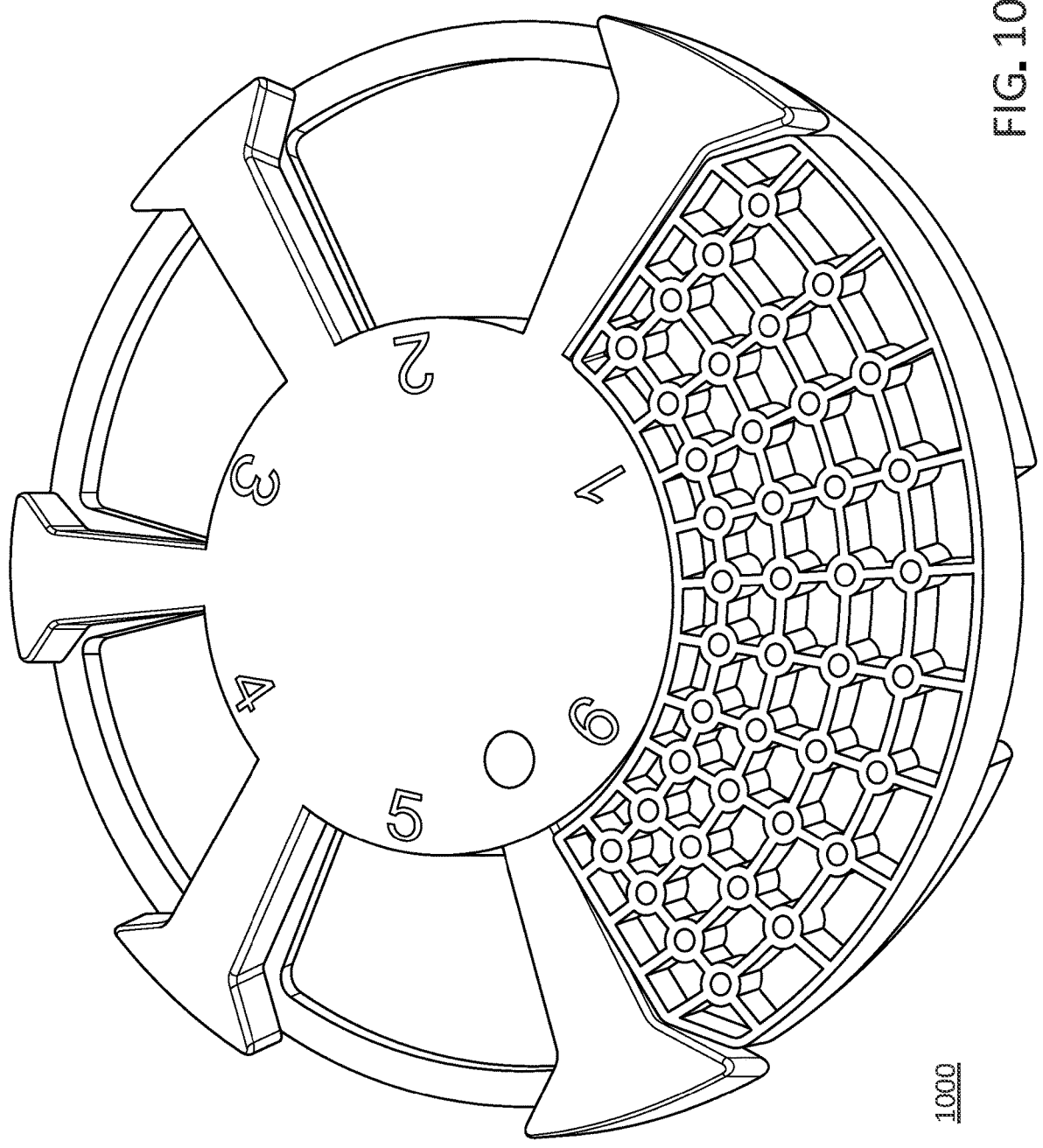

FIG. 10 shows as drawing illustrating an exemplary multiwell plate provided herein that comprises a solid black carrier, which is configured to hold a plurality of chips. One chip is shown that comprises assay wells and is made of a clear or translucent material. The multiwell plate is shown mounted in an assay measurement unit (AMU) or assay station provided herein.

Figure 11B:
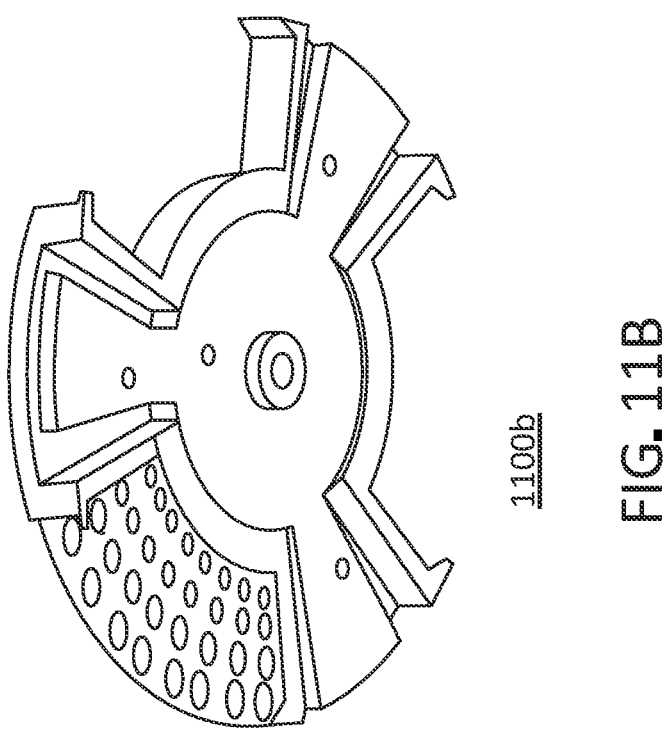
Figure 11A:
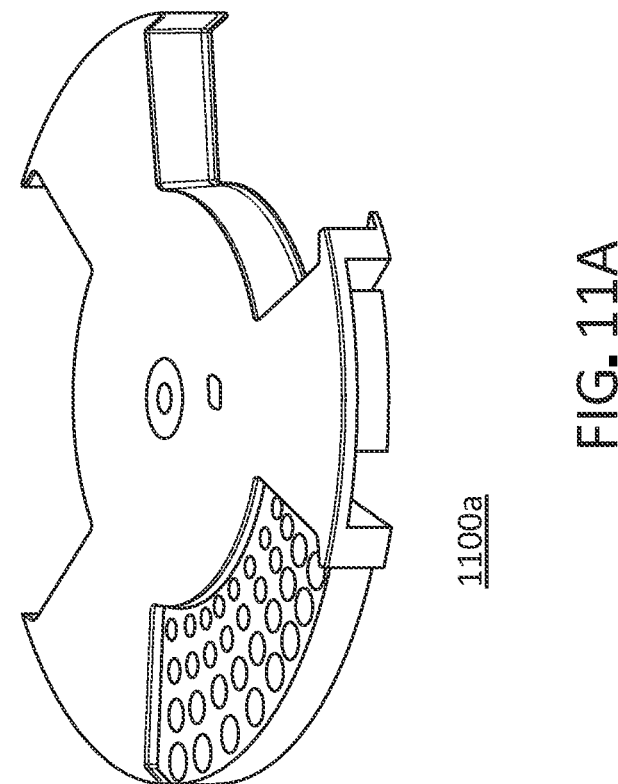

FIG. 11A and FIG. 11B show a top view (FIG. 11A) and a bottom view (FIG. 11B) of a carrier component of an exemplary multiwell plate provided herein. The carrier is configured to hold three chips. One chip is shown in solid black that is held by the carrier. The chip comprises four pluralities of wells (32 wells total) that are organized in a concentric arrangement around the center of the multiwell plate. Each well of the four pluralities of wells has a cylindrical shape. The four pluralities of wells differ from each other, e.g., in their diameters and volumes.

Figure 12B:
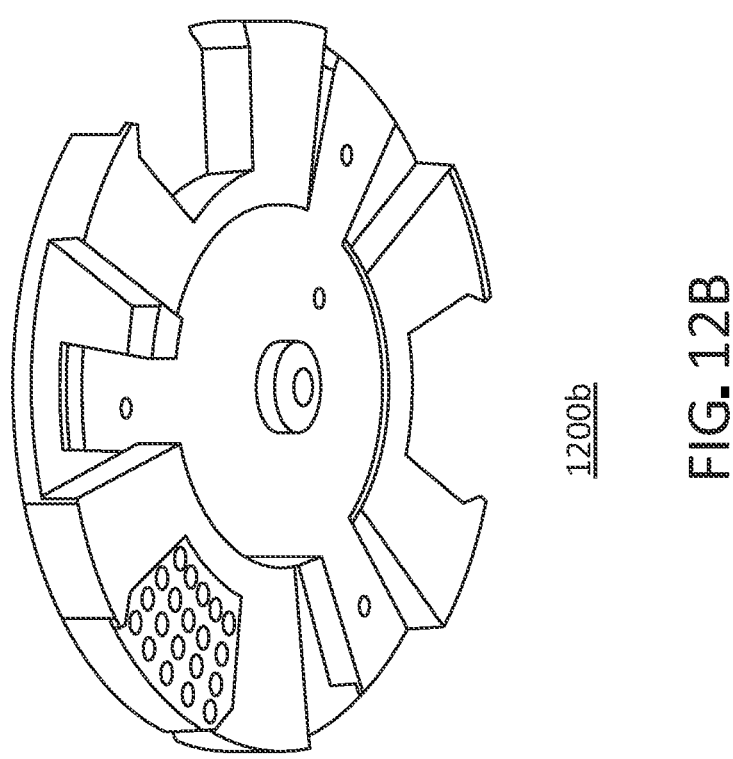
Figure 12A:
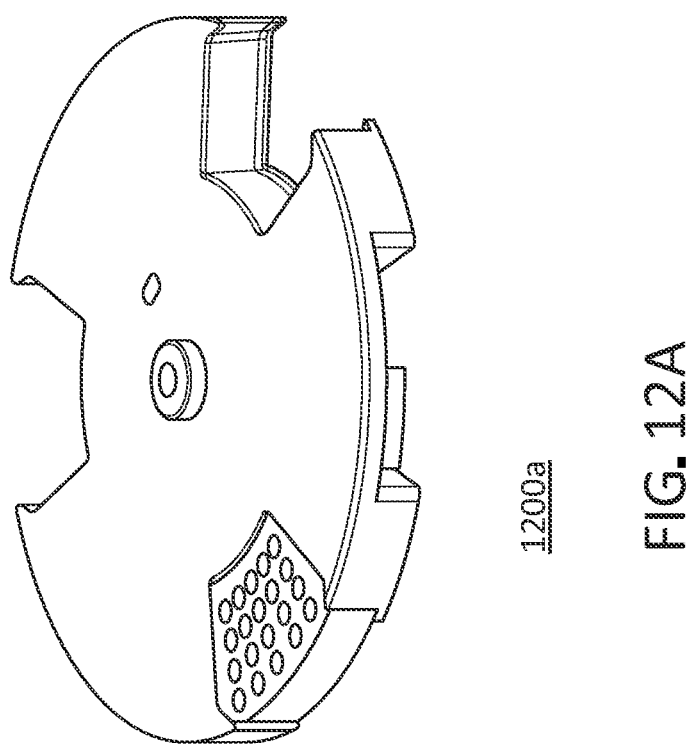

FIG. 12A and FIG. 12B show a top view (FIG. 12A) and a bottom view (FIG. 12B) of a carrier component of an exemplary multiwell plate provided herein. The carrier is configured to hold three chips. The carrier shown in FIG. 12A and FIG. 12B is configured to hold smaller chips than the carrier shown in FIG. 11A and FIG. 11B. One chip is shown in solid black that is held by the carrier. The chip comprises four pluralities of wells (20 wells total) that are organized in a concentric arrangement around the center of the multiwell plate. Each well of the four pluralities of wells has a cylindrical shape and identical dimensions.

Figure 13B:
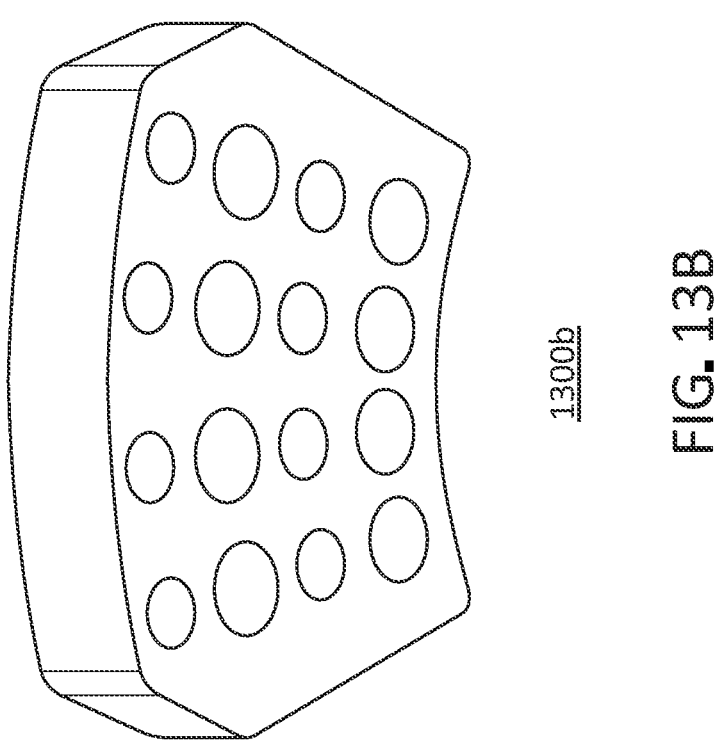
Figure 13A:
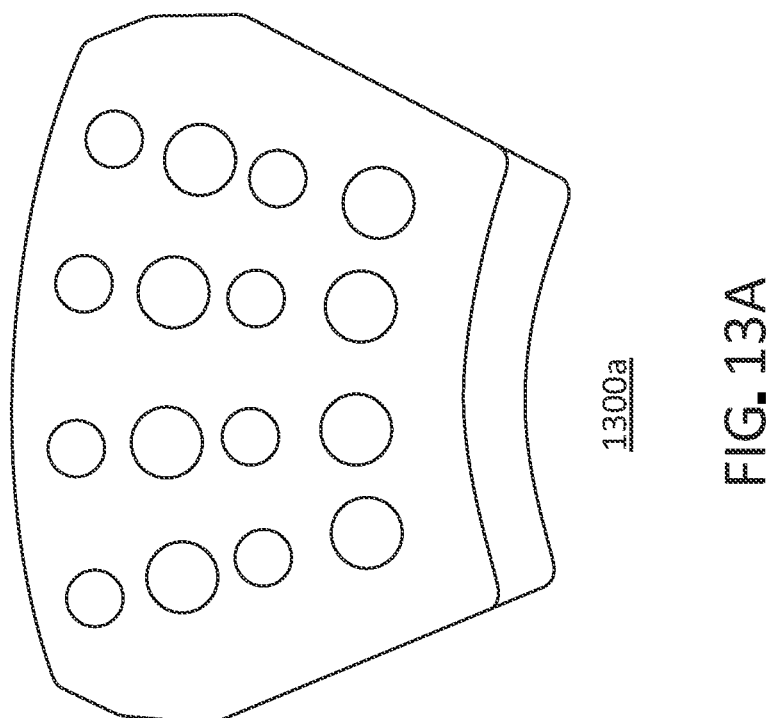
Figures 13C, 13D:
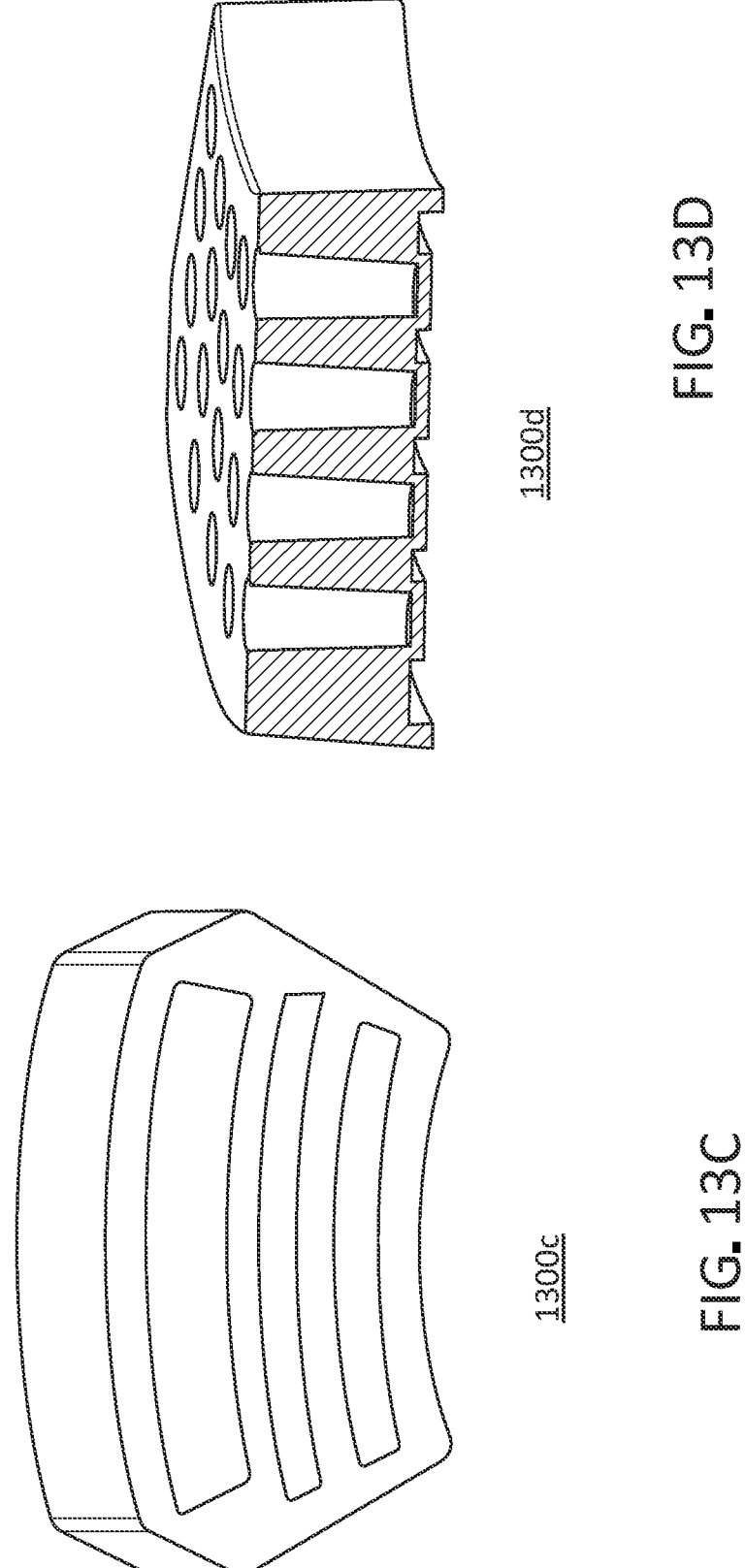
Figure 13F:
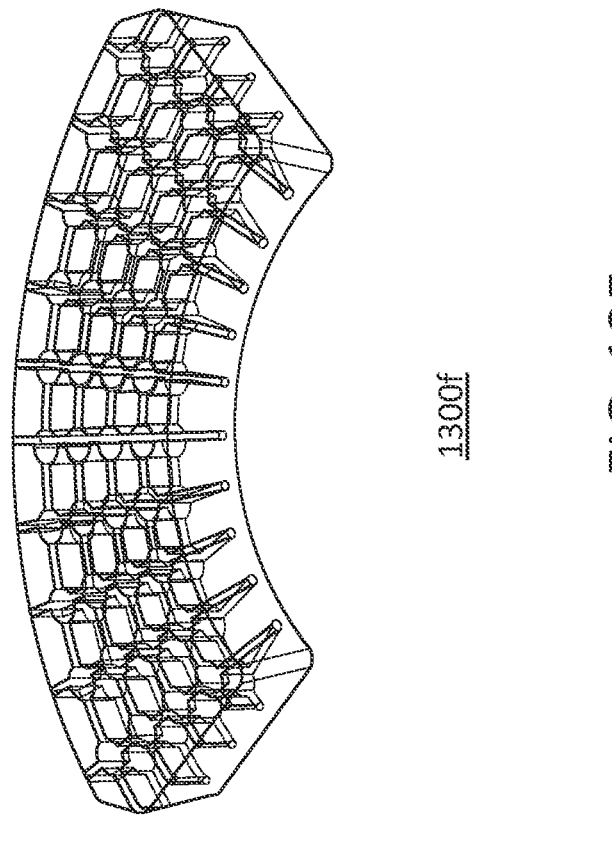
Figure 13E:
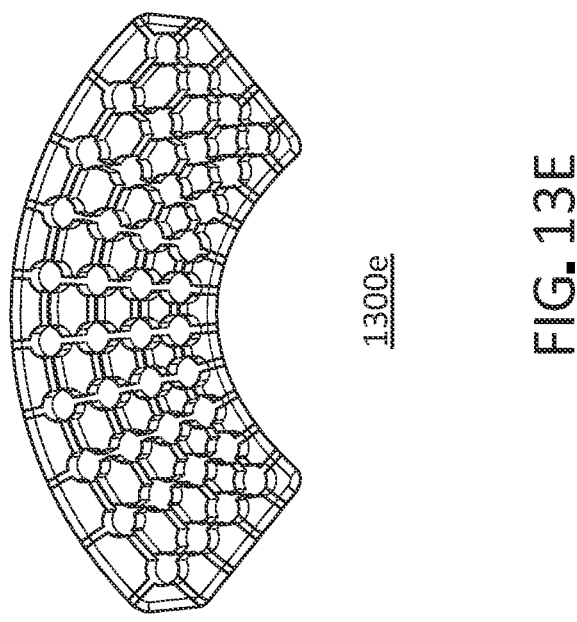
Figure 13H:
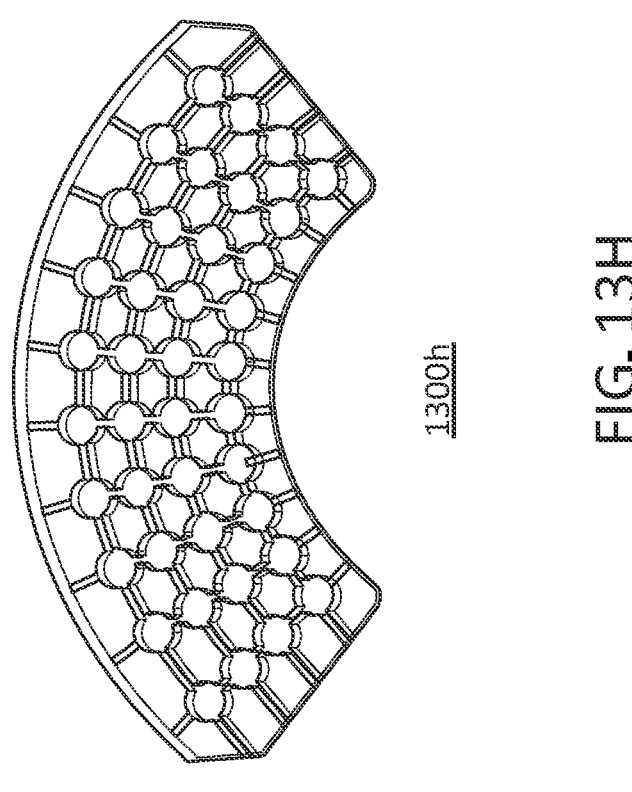
Figure 13G:
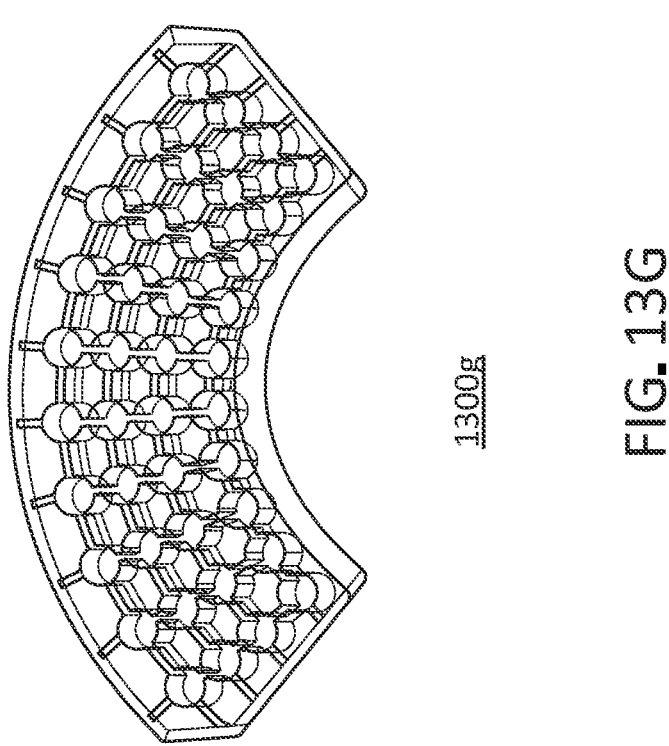
Figure 13J:
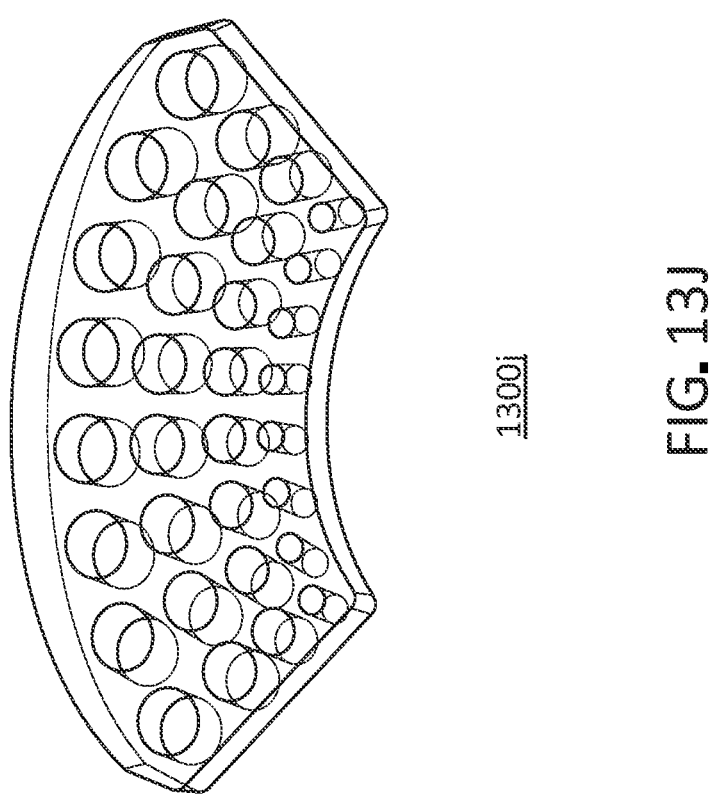
Figure 13I:
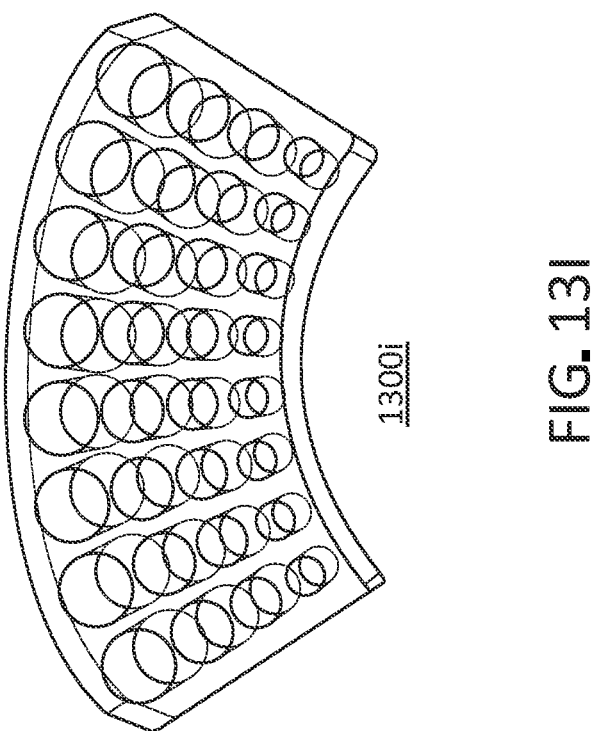
Figure 13L:
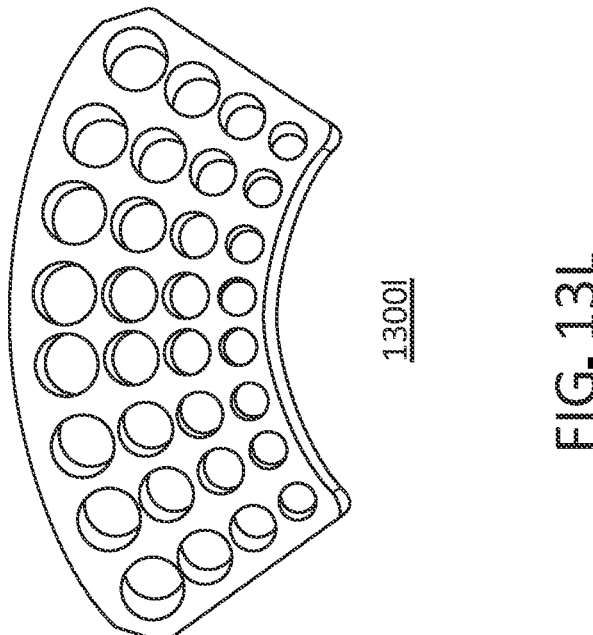
Figure 13K:
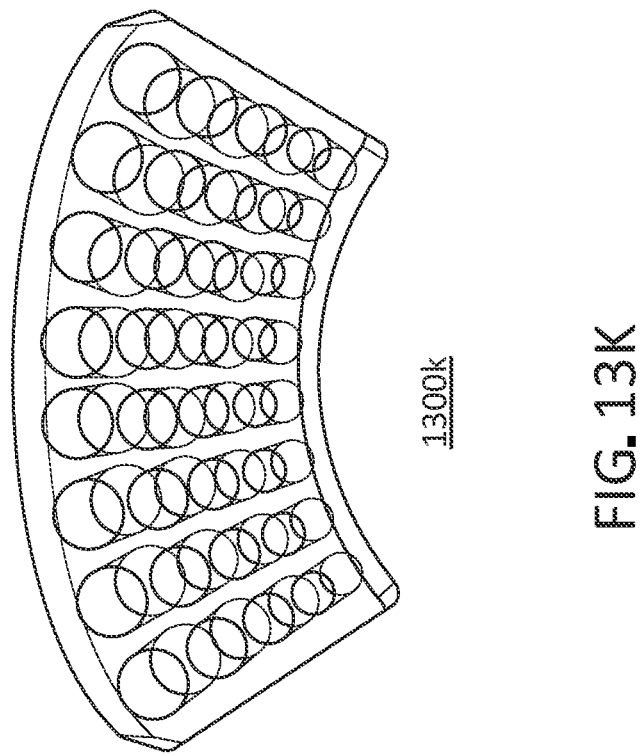
Figure 13N:
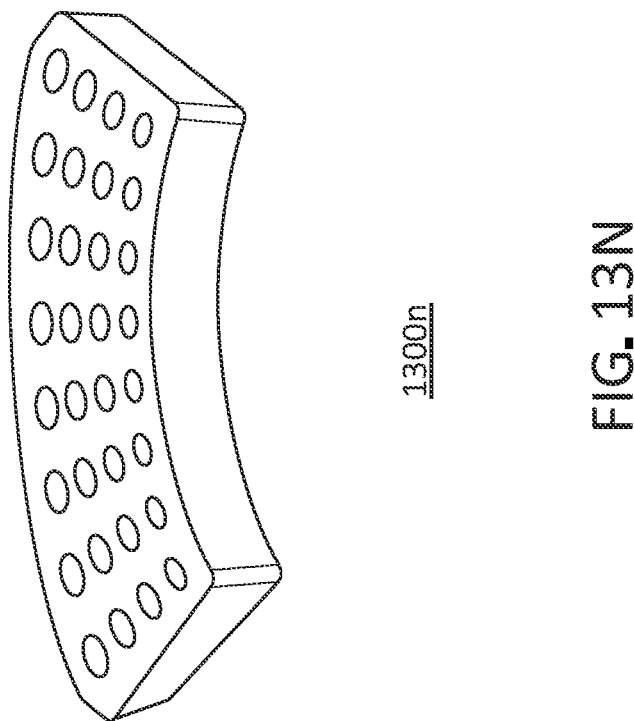
Figure 13M:
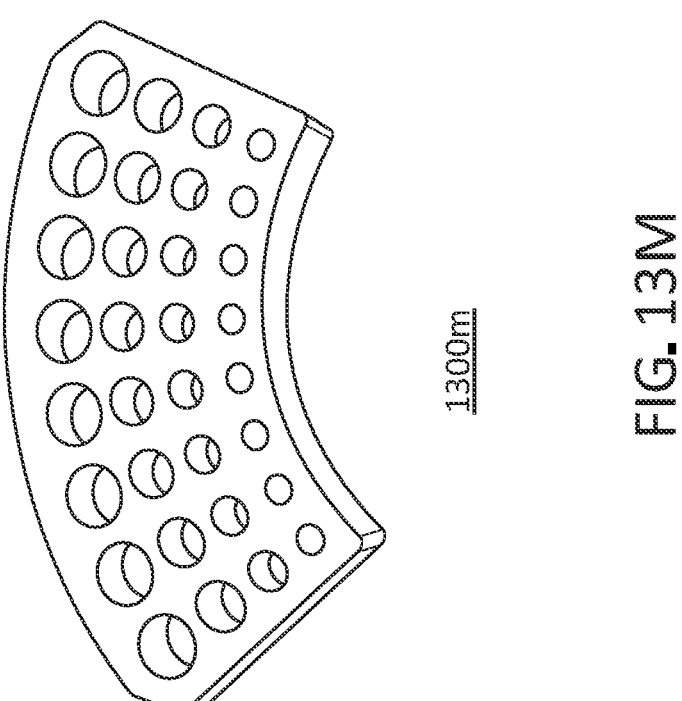
Figure 130:
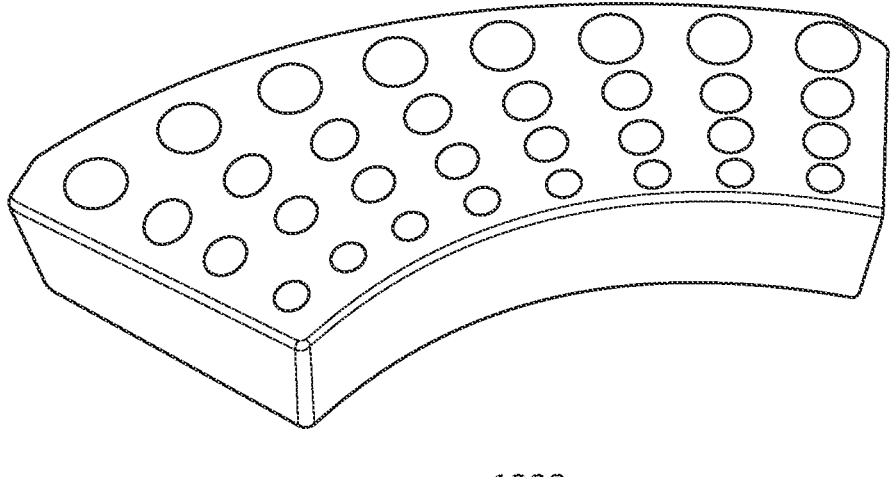

FIG. 13A, FIG. 13B, FIG. 13C, FIG. 13D, FIG. 13E, FIG. 13F, FIG. 13G, FIG. 13H, FIG. 13I, FIG. 13J, FIG. 13K, FIG. 13L, FIG. 13M, FIG. 13N, and FIG. 13O show photographs illustrating different exemplary chip components of multiwell plates provided herein. FIG. 13A and FIG. 13B illustrate exemplary chips of solid material and non-translucent well bottoms. FIG. 13B illustrates a cut view of an exemplary chip with assay wells sharing the same shapes and dimensions. FIG. 13C illustrates an exemplary chip with three pluralities of troughs (6 troughs total) that differ in their shapes, volumes and height, width and depth dimensions. FIG. 13E, FIG. 13F, FIG. 13G, FIG. 13H, FIG. 13J, and FIG. 13K illustrate chips made of clear or translucent material, including clear or translucent well bottoms, with multiple pluralities of assay wells sharing the same dimensions. FIG. 13I, FIG. 13J, and FIG. 13K illustrate chips made of clear or translucent material, including clear or translucent well bottoms, with multiple pluralities of assay wells of cylindrical shapes that differ in their diameters. FIG. 13L, FIG. 13M, and FIG. 13N illustrate exemplary chips having solid black walls and clear or translucent bottoms. FIG. 13O illustrates an exemplary chip having solid black walls and assay well bottoms covered by a film.

Figure 14:
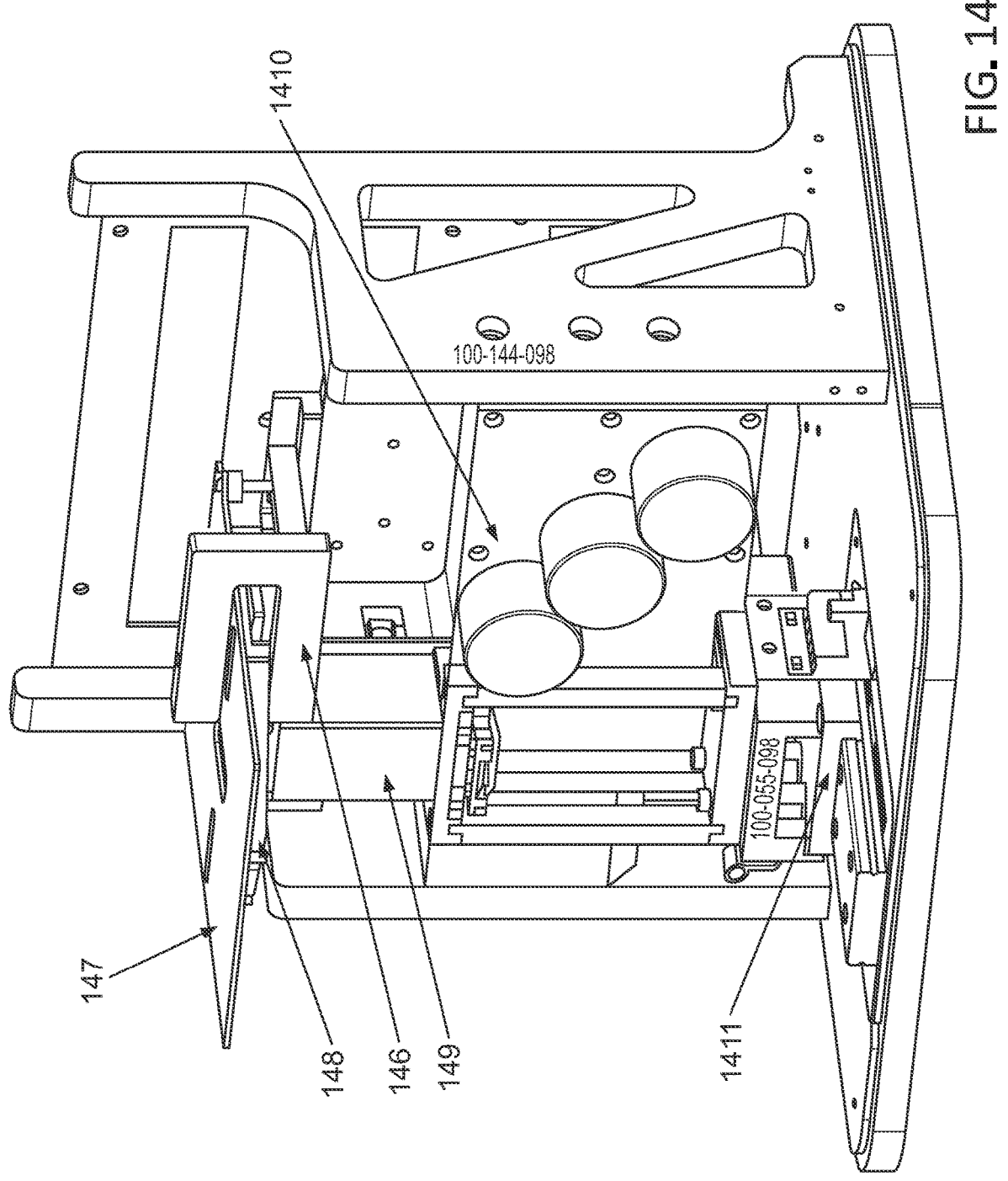

FIG. 14 shows a drawing of an exemplary Truvian assay measurement system (AMU) provided herein.

Figure 15:
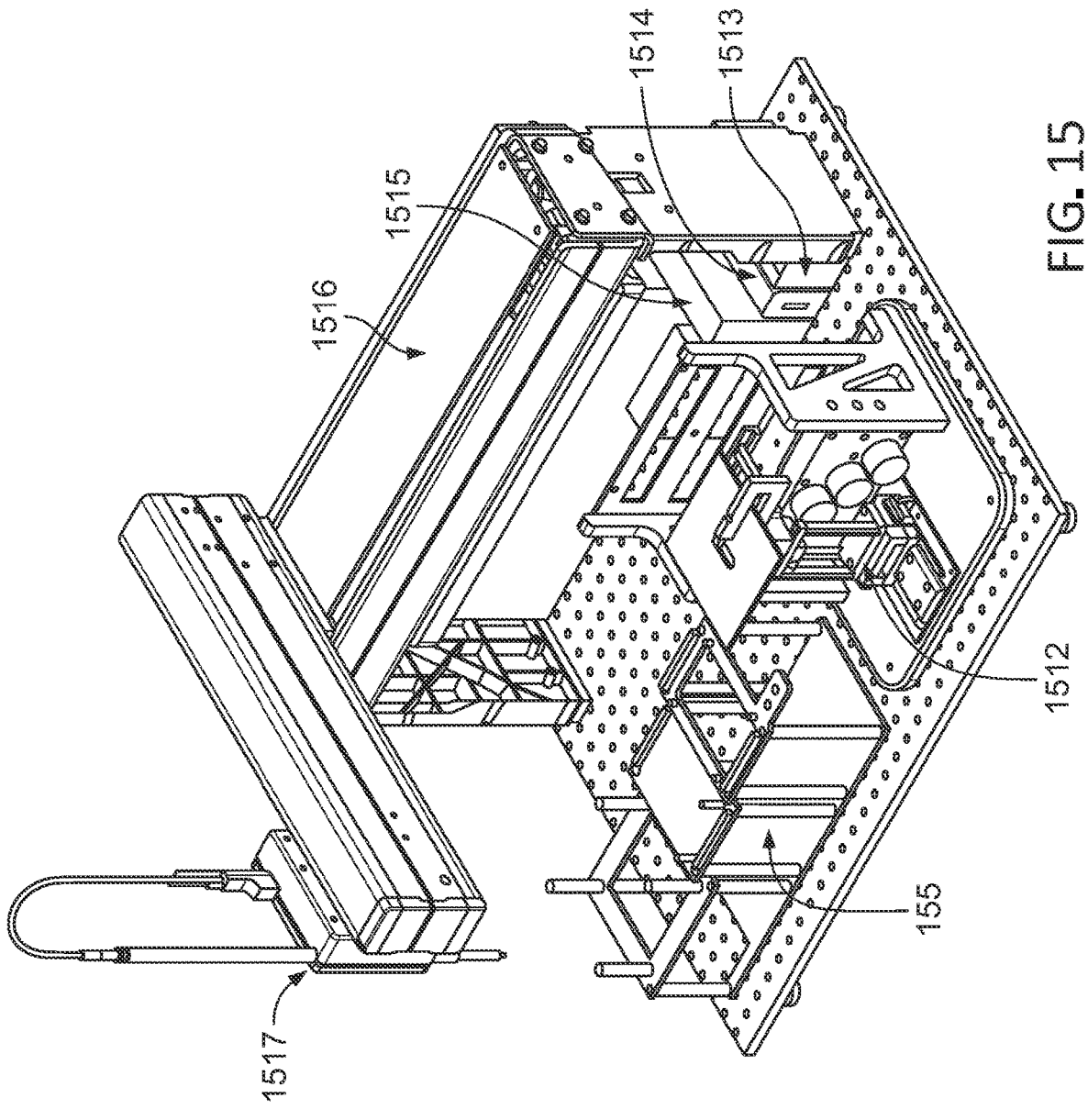

FIG. 15 shows a drawing of an exemplary Truvian assay station provided herein.

Figure 16A:
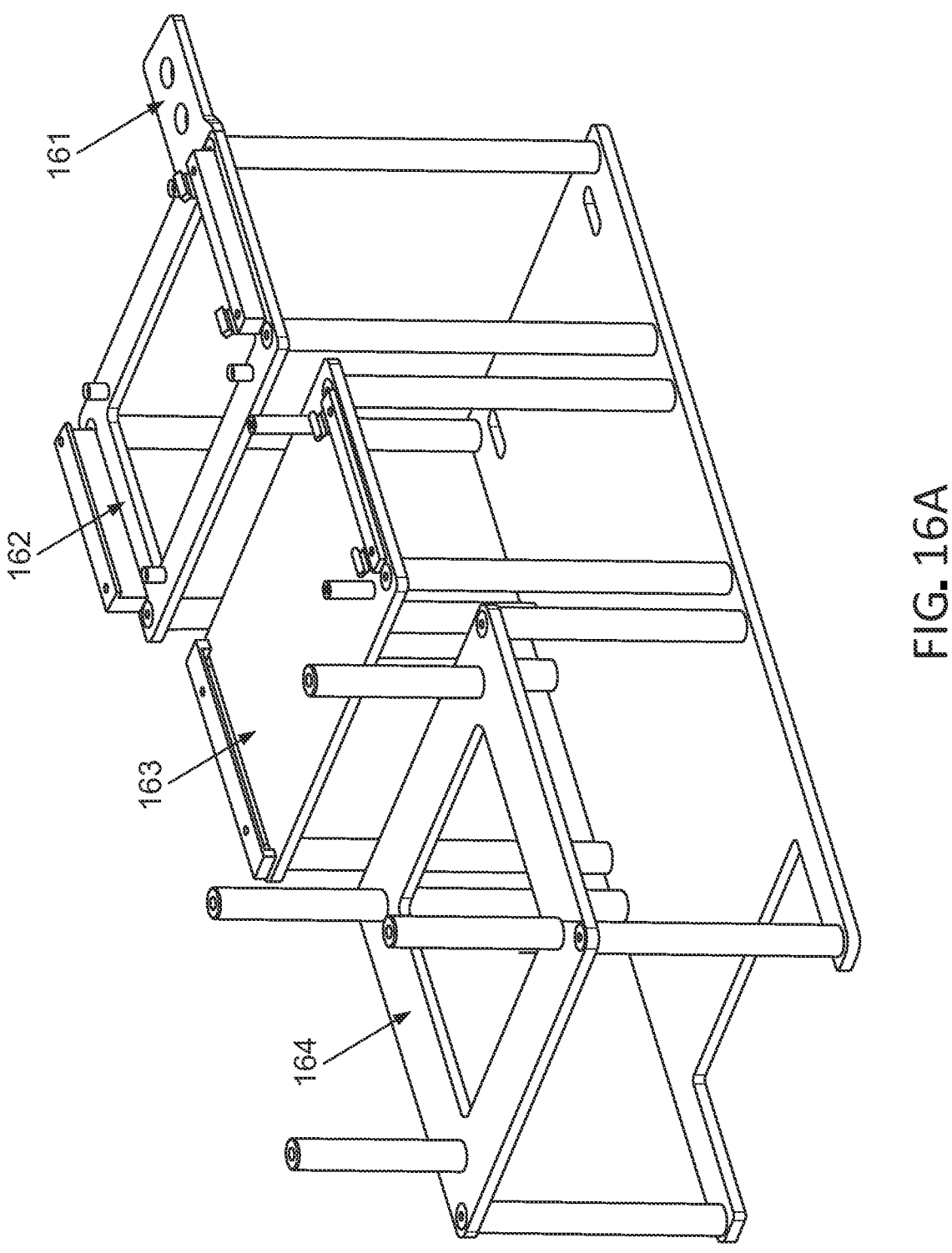
Figure 16B:
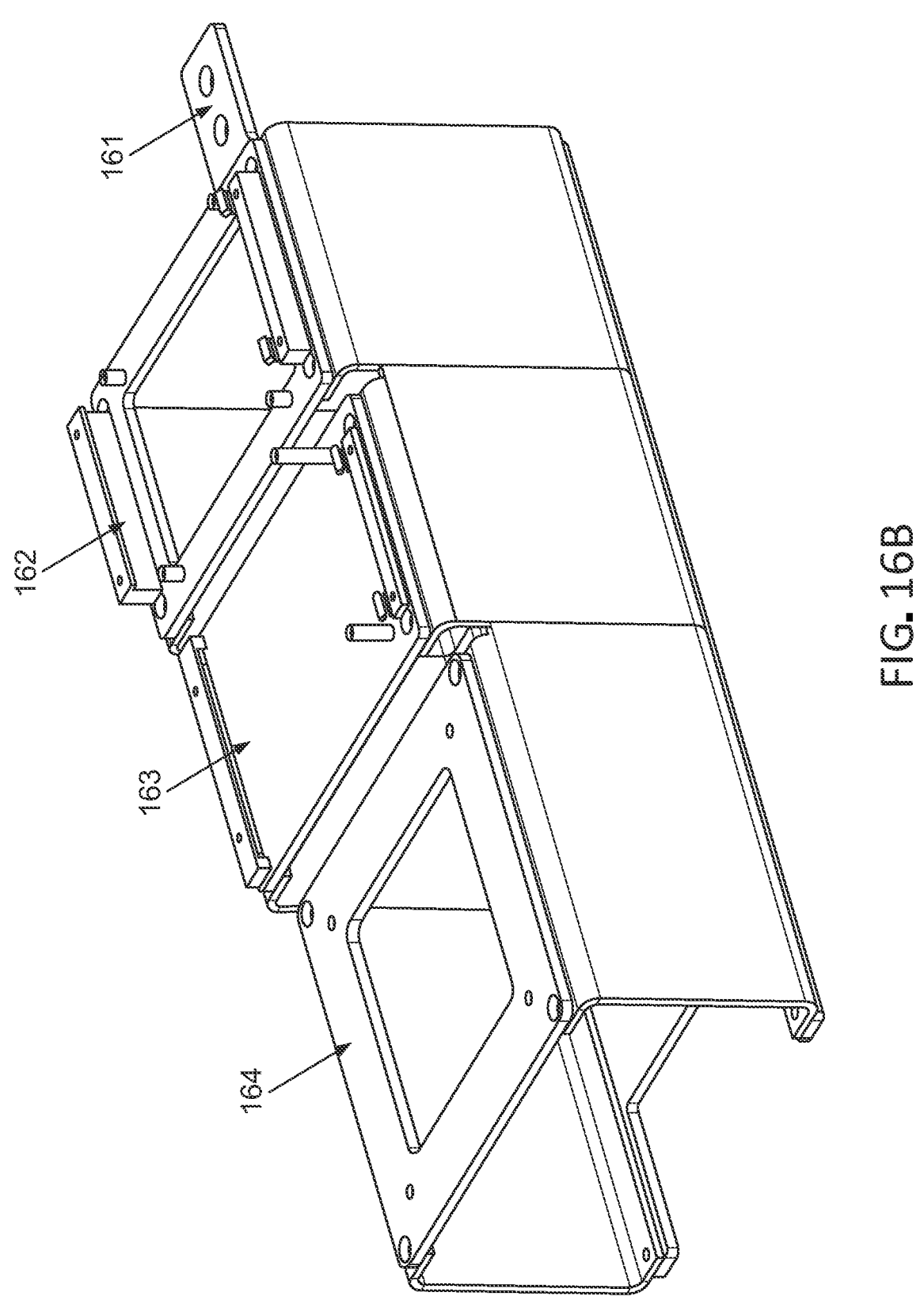

FIG. 16A and FIG. 16B show drawings of exemplary consumables mount components of a Truvian assay station.

Figure 17:
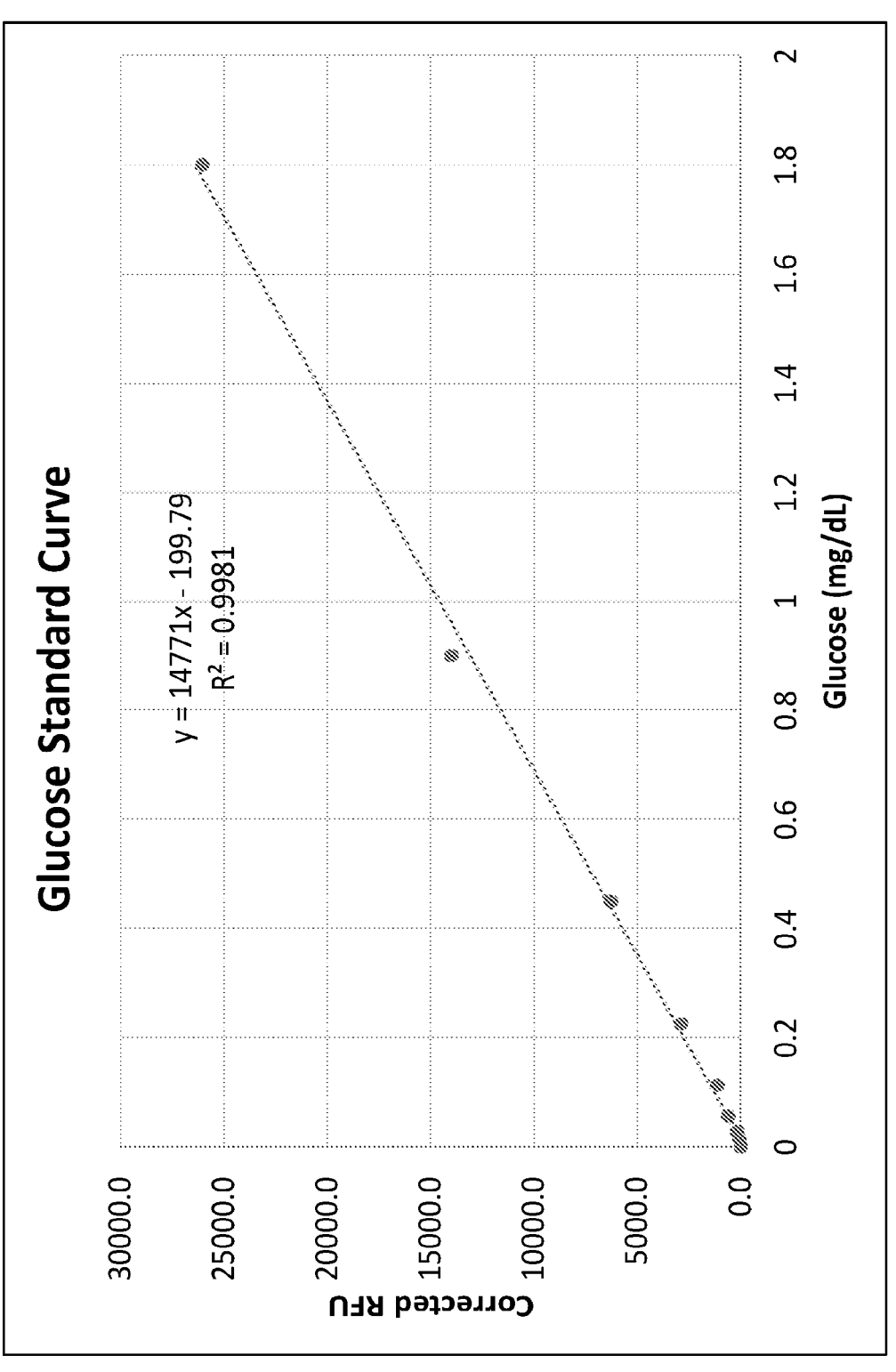

FIG. 17 shows a graph illustrating an exemplary glucose standard curve from a fluorescence-based assay performed in a multiwell plate component ("chip") provided herein.

Figure 18:
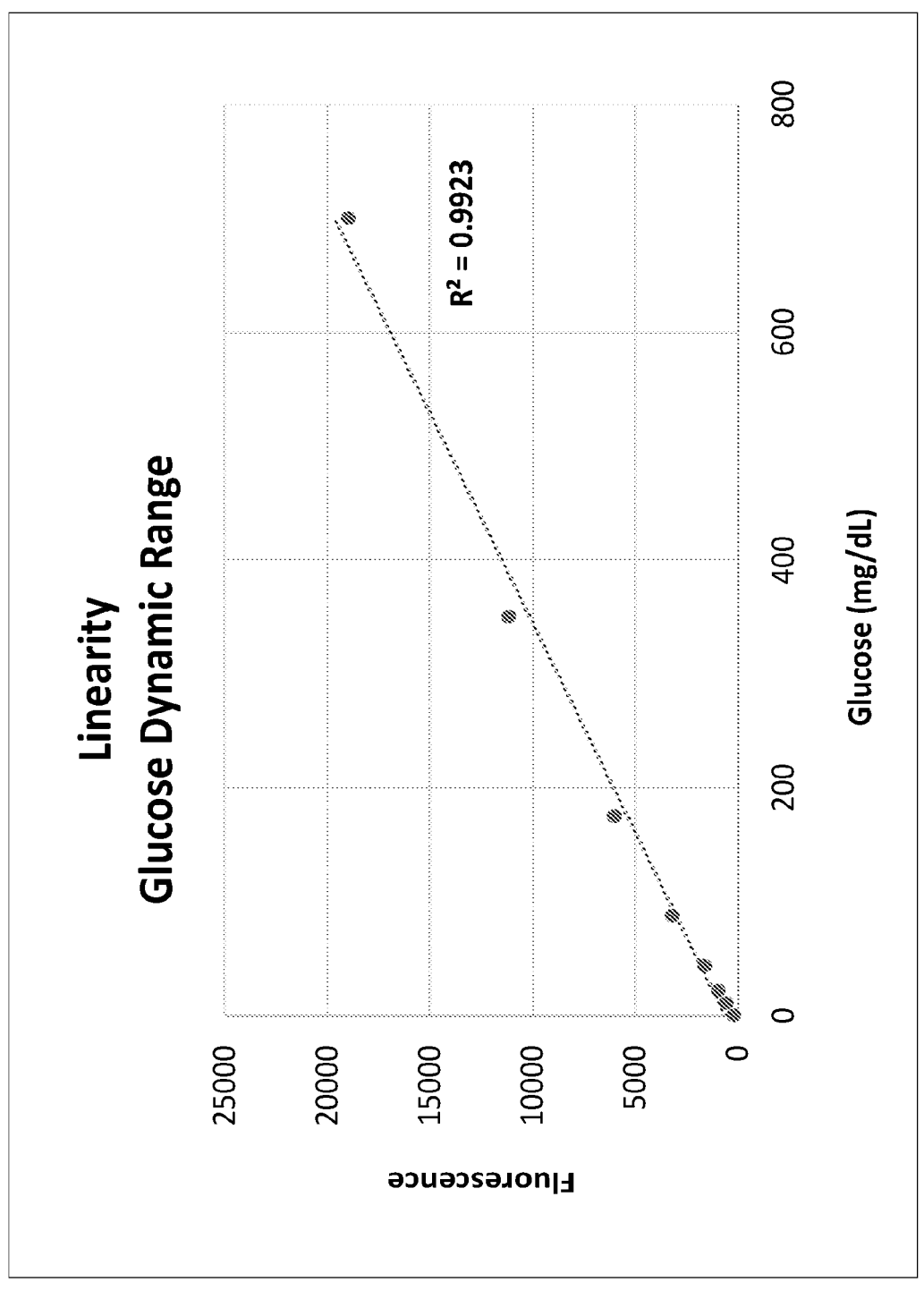

FIG. 18 shows a graph illustrating an exemplary glucose standard curve from a fluorescence-based assay performed in a traditional multiwell plate.

Figure 19:
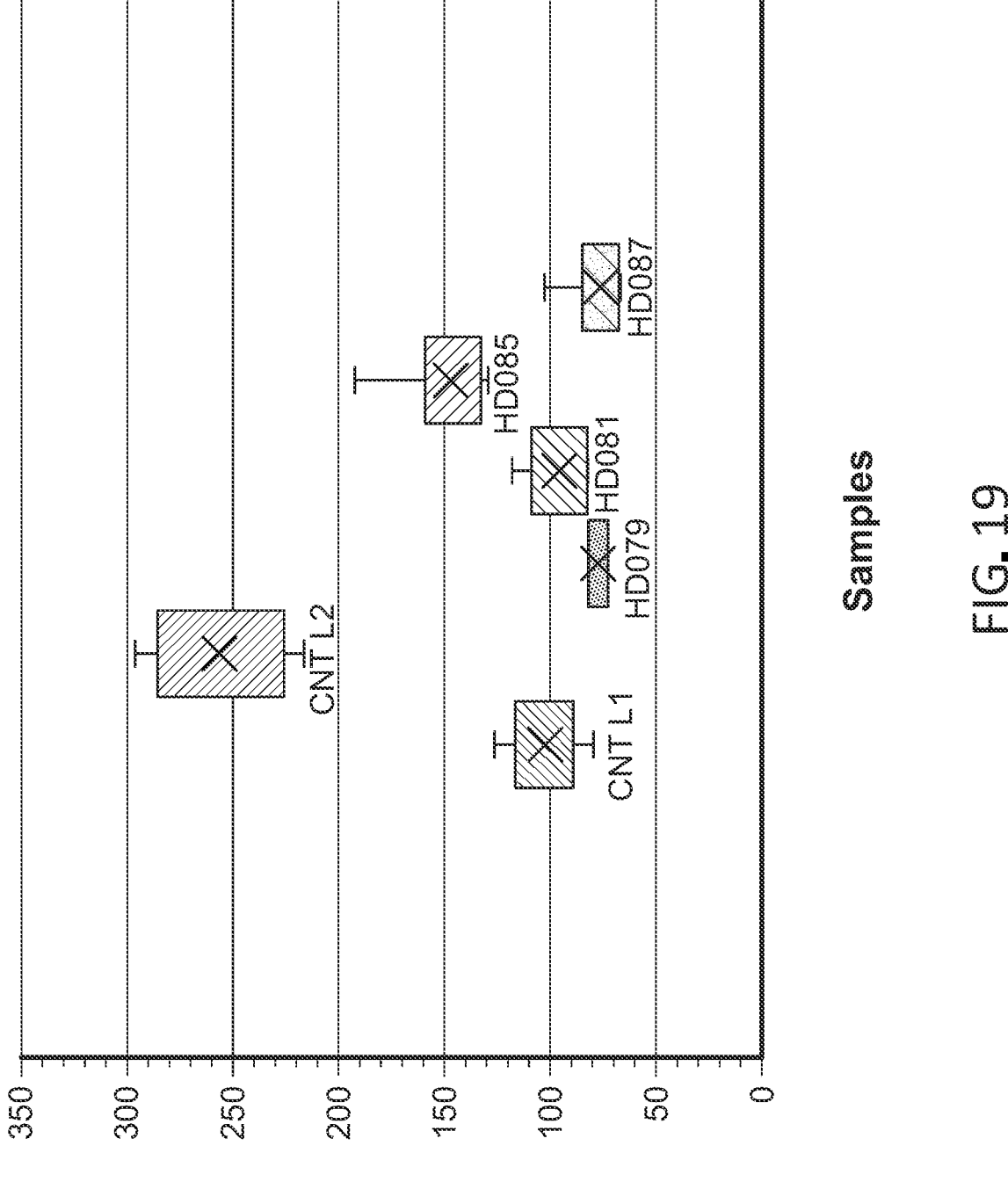

FIG. 19 shows a graph illustrating results from a glucose determination in donor blood samples using a traditional multiwell plate.

Figure 20:
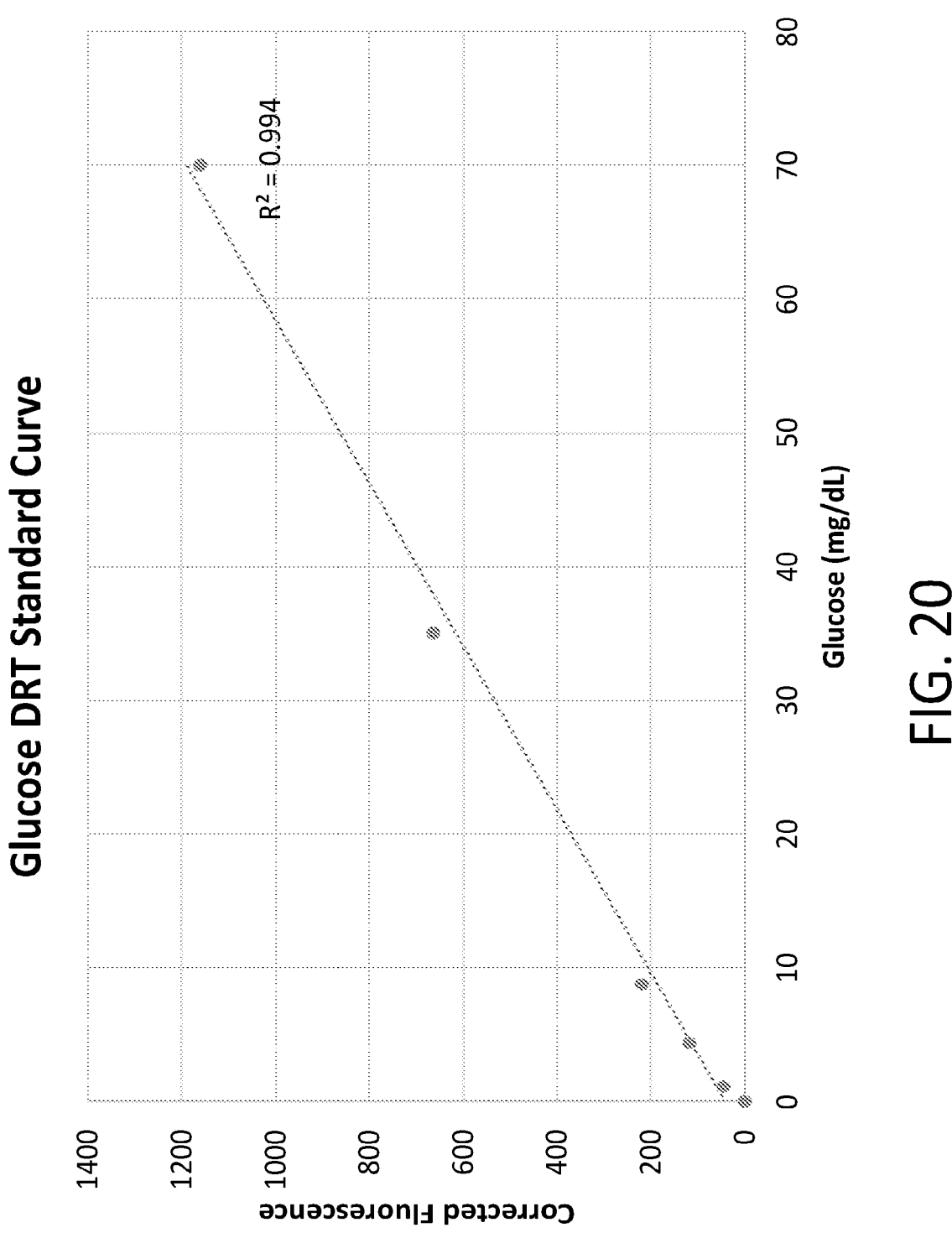

FIG. 20 shows a graph illustrating a glucose standard curve generated using a fluorescence-based glucose assay in combination with dried reagent technology (DRT) in a traditional multiwell plate.

Figure 21:
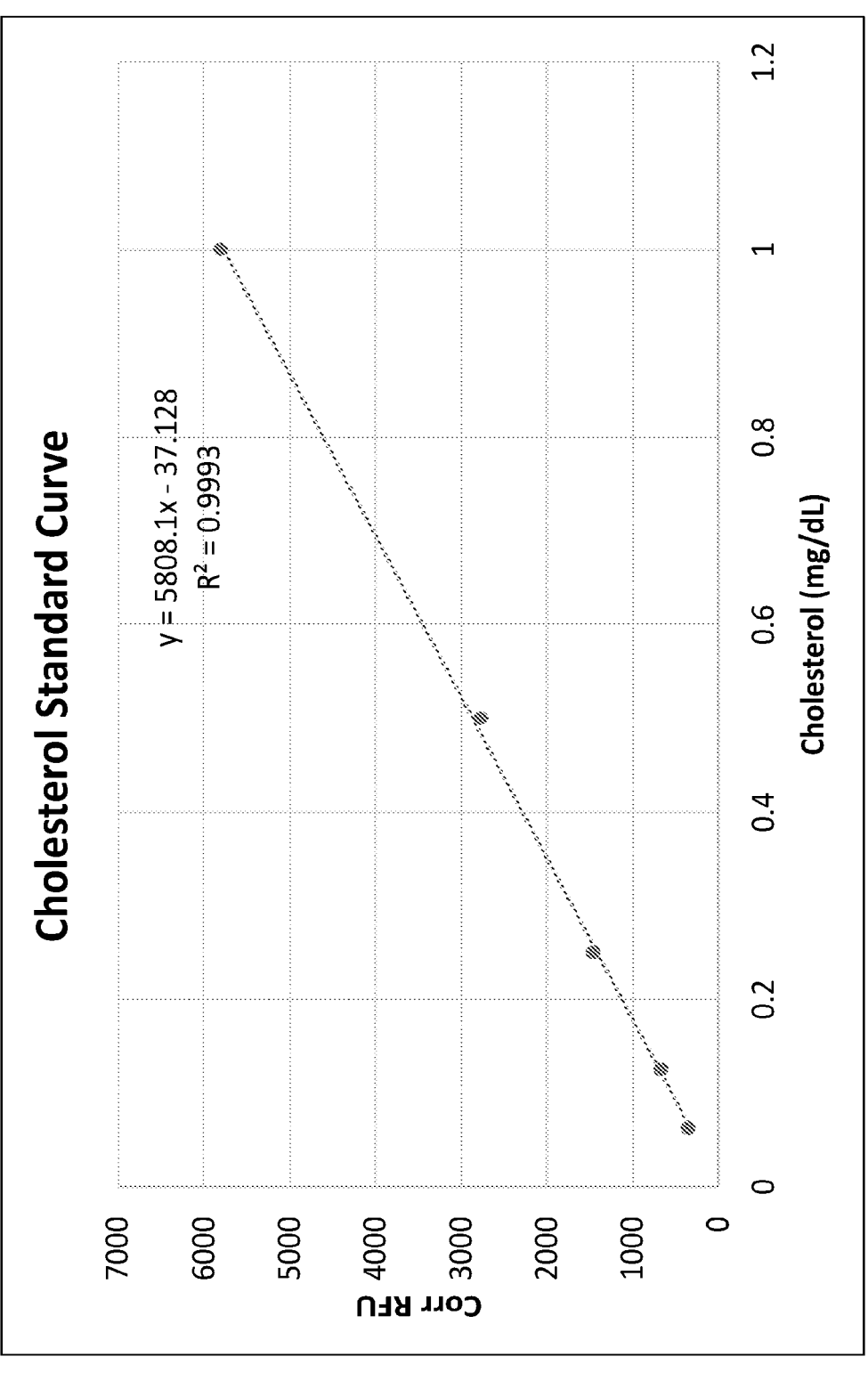

FIG. 21 shows a graph illustrating an exemplary cholesterol standard curve from a fluorescence-based assay performed in a Truvian cartridge component ("chip").

Figure 22:
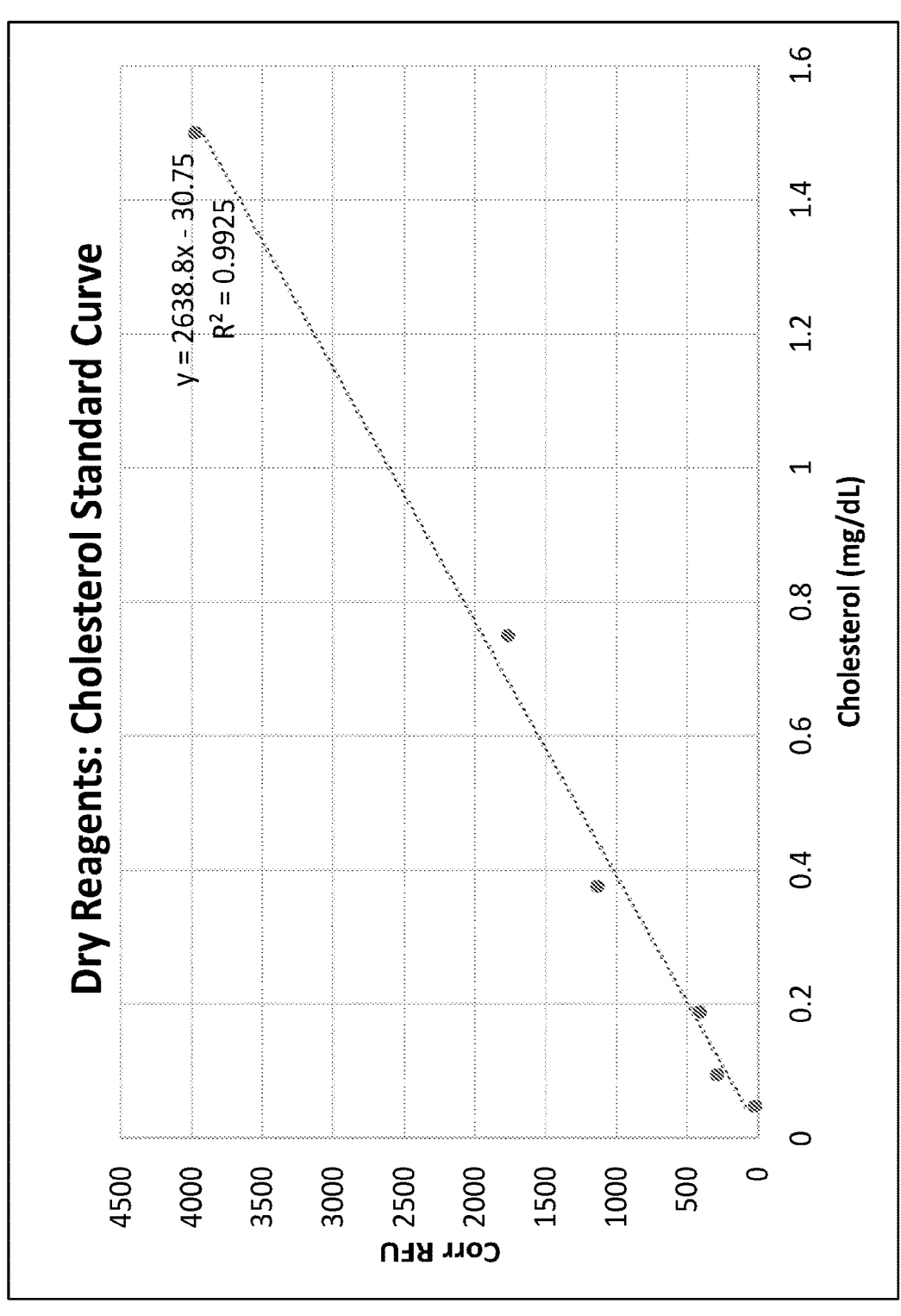

FIG. 22 shows a graph illustrating a cholesterol standard curve generated using a fluorescence-based cholesterol assay performed in a Truvian cartridge component ("chip") in combination with dried reagent technology (DRT).

Figure 23:
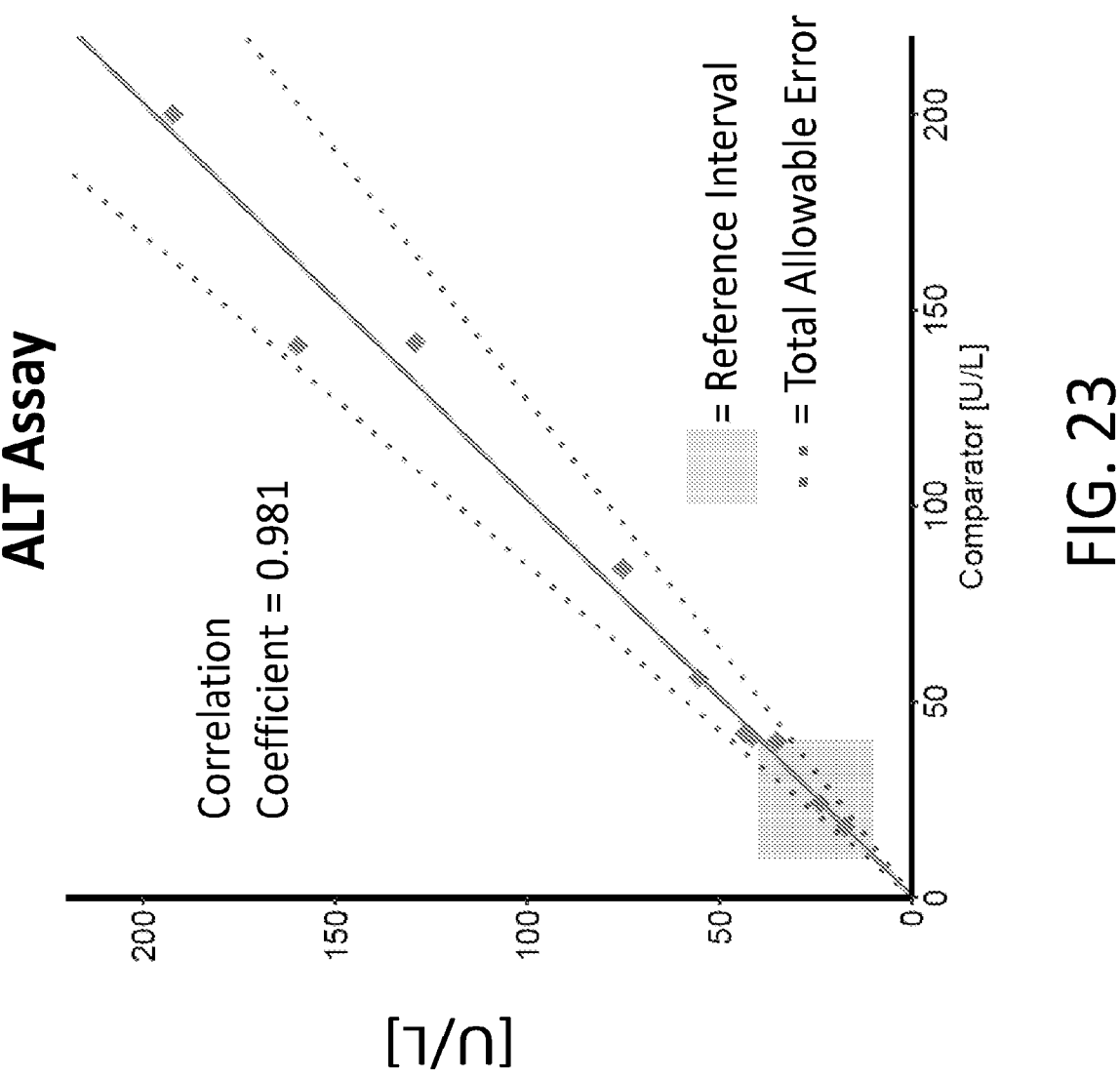

FIG. 23 shows a graph illustrating an exemplary assay standard curve from an absorbance-based assay alanine aminotransferase (ALT) assay performed in a traditional multiwell plate and a comparator assay.

Figure 24A:
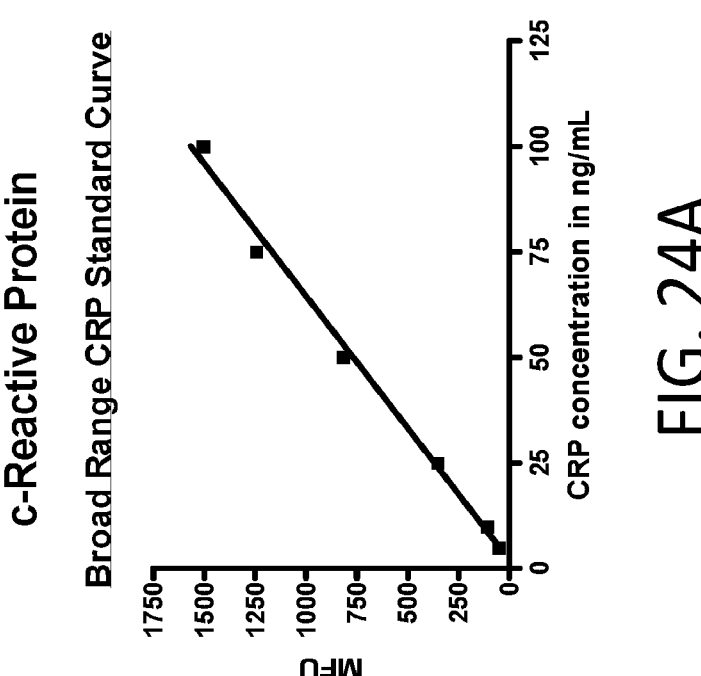
Figure 24B:
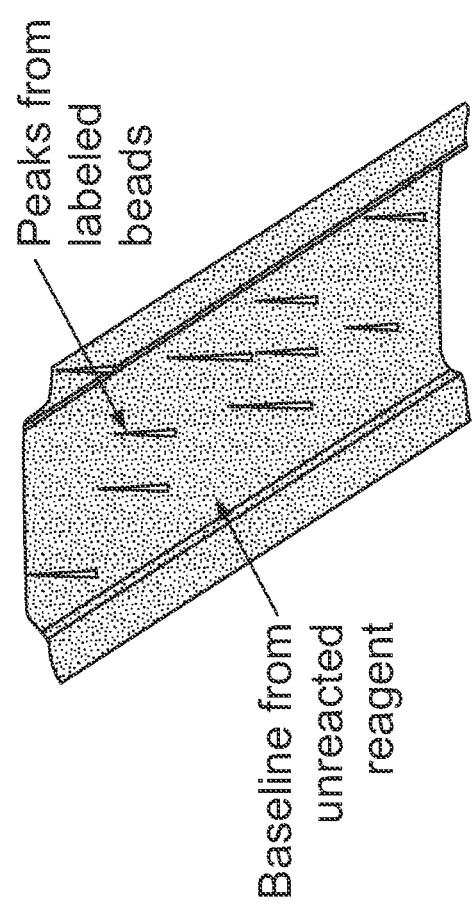

FIG. 24A and FIG. 24B illustrate results of a heterogeneous fluorescence-based immuno-assay for C-reactive protein (CRP) read out in a Truvian Assay Measurement Unit.

Figures 25A, 25B:
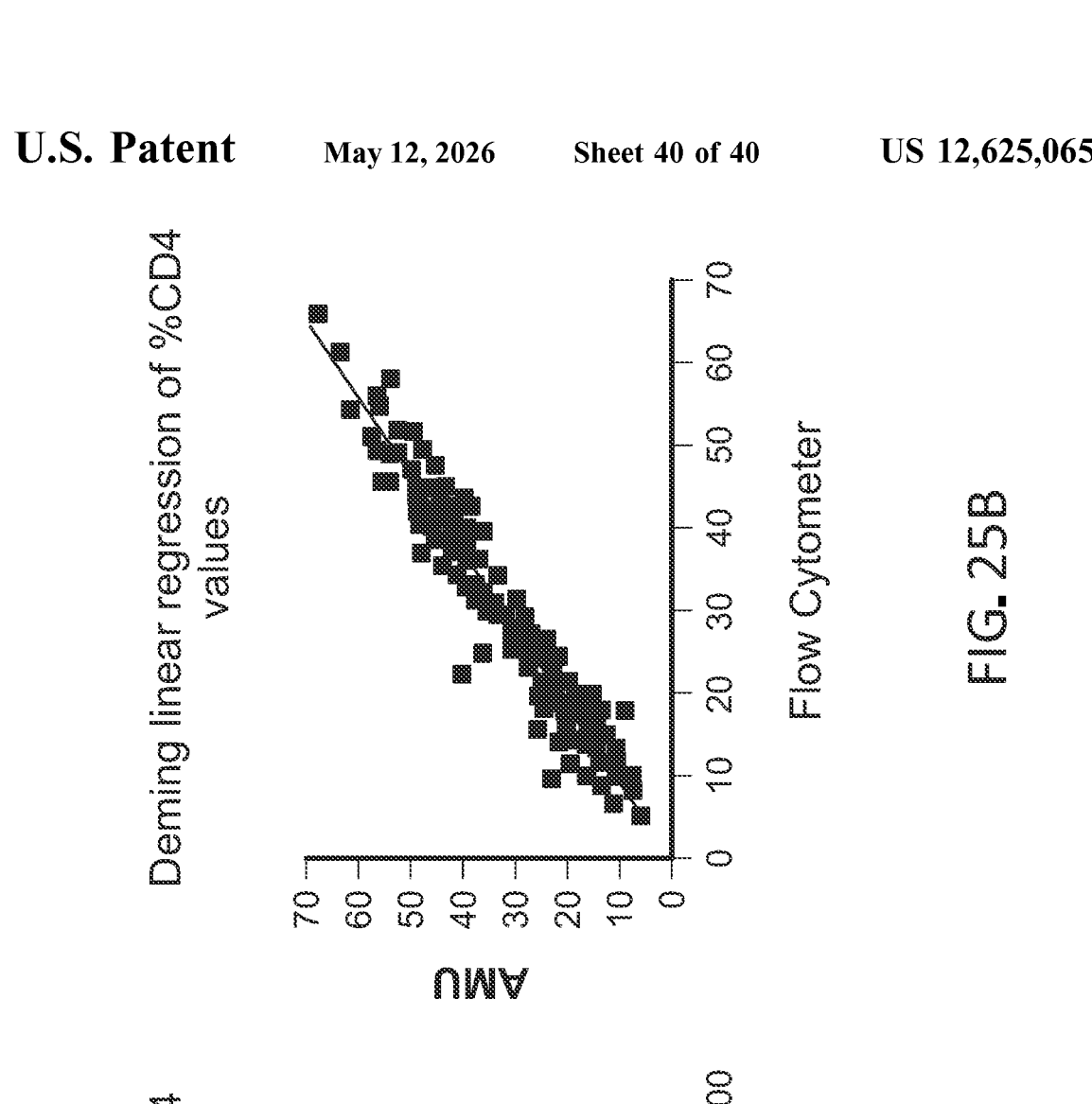

FIG. 25A and FIG. 25B illustrate results of a fluorescent cell-based immunoassay detecting CD4-positive cells in a Truvian Assay Measurement Unit, and of a FACS comparator assay.

5. DETAILED DESCRIPTION

The present disclosure is based, in part, on the realization that the field of DTC diagnostics can benefit from an assay platform that allows for reliable, low-cost testing of a very small volume of a consumer's biological sample (e.g., a blood sample of 25-100 µl). A desirable assay platform can, e.g., conduct a parallel and robust analysis of multiple analytes, e.g., analytes in a multianalyte set. A multianalyte set can, for example, be related to the consumer's health or general wellness. A multianalyte set can include, e.g., one or more analytes of different analyte classes, such as a small molecule analyte (e.g., <500 Da; cholesterol, glucose), a large molecule analytes (e.g., >10 kDa; cytokines, hemoglobin, DNA), or a cell (e.g., a bacterial or eukaryotic cell; mammalian cell; red blood cell or leukocyte).

Traditional diagnostic testing in a clinical setting typically involves the drawing of large sample volumes from a patient by invasive means and long waiting periods between sample collection and testing. Also, diagnostic test results are commonly communicated to patients through a healthcare professional, and are not directly accessible to the patient, e.g., through an internet or mobile interface in the absence of a physician. In biological samples, different analytes are often present at vastly different concentrations that can range from very high concentrations (e.g., in the range of up to 100 mg/dL; e.g., fasting blood glucose in a healthy subject) to very low concentrations (e.g., below 1 ng/ml; e.g., certain inflammatory cytokines in a healthy subject). To account for the differences in analyte chemistries and concentrations, in traditional clinical settings, different analytes are typically tested separately on an analyte-by-analyte basis, using specially designated instruments for individual analytes, and using relatively large reaction volumes (e.g., 1 ml). Independent analyte testing commonly requires the drawing of relatively large samples from patients (e.g., 10-15 ml of blood), typically by invasive means (e.g., a needle). Samples from multiple patients are traditionally collected long before any of the samples is tested for a given analyte to allow for the subsequent parallel testing of multiple samples for the same analyte. Such a traditional process commonly involves substantial waiting periods for the patient between sample collection, sample testing, and the communication of results. Moreover, such a traditional process also typically involves substantial sample handling, e.g., for purposes of sample storage between sample collection and sample testing, and to stabilize samples during storage (e.g., aliquotting and freezing of samples). Additionally, independent testing of different analytes is generally not coordinated in time. Thus, if sample stability is a problem with respect to any given analyte, variability and inaccuracies can be introduced into test results if the testing of different analytes in a panel or of different samples is not coordinated in time.

The present disclosure is based, in part, on the realization that in a DTC diagnostics setting it is desirable for an individual consumer to provide a small sample through relatively non-invasive means, to have that sample tested for multiple analytes of the consumer's choice without substantial delay, to obtain robust test results and for the consumer and other consumer-authorized third parties (e.g., wellness counselor) to have direct access to such test results and manage such test results without the need to interface with a healthcare professional.

The present disclosure is further based, in part, on the realization that the collection of robust, high-quality DTC diagnostics data can be facilitated i) at the assay technology level through synchronization of multianalyte testing of individual consumer samples, ii) at the apparatus level through seamless integration of sample collection and sample testing at the POCC, and iii) at the system level through standardized and quality-controlled collection of large diagnostic datasets based on a network of multianalyte detection systems provided herein. At the multianalyte assay level, the multiwell based assay technologies provided herein allow for the collection of high-quality data through synchronized testing of samples from individual consumers across flexible panels of biochemical and cell-based diagnostic tests. See, e.g., FIG. 1. At the apparatus level, the multianalyte detection systems provided herein allow for seamless integration of sample collection and sample testing at the POCC, thereby avoiding sample deterioration during sample storage. See, e.g., FIG. 2. At the system level, the low-cost and high-quality data collection and the ease of data monitoring and tracking enabled by the multianalyte systems provided herein is expected to incentivize growing numbers of consumers to engage in repeat-testing of growing numbers of diagnostic or wellness-related parameters of interest, and thereby to facilitate the collection of "big data" sets for data mining, e.g., by consumers or medical researchers. See, e.g., FIG. 3.

Provided herein are systems, devices and methods for performing robust, low-cost testing of a small sample volume (e.g., a 25-100 μl blood sample) for multiple analytes. The systems, devices and methods described herein generally involve analyzing two or more different analytes (e.g., a small molecule analyte, a protein analyte, and a cell) on a single multiwell plate using different assay formats (e.g., a heterogeneous assay and a solution assay) or different readouts (e.g., fluorescence and absorbance). The multiwell plates described herein typically comprise two or more different pluralities of wells on a single plate whereby each of the different pluralities of wells is configured to perform one or more different types of assays for one or more different analytes. For example two different pluralities of wells on the same multiwell plate can differ from one another with respect to one or more properties, for example, well geometry (e.g., cube or cylinder) or dimension (e.g., volume), color or transparency of a well's wall or floor (e.g., translucent or opaque), well surface property (e.g., high protein-binding or cell adhesion promoting), or with respect to any other property affecting the performance of an assay for an analyte (e.g., assay reagents).

The systems, devices and methods described herein allow for the highly coordinated performance of different assays on the same multiwell plate, including kinetic assays and endpoint assays. Different assay formats can be conducted in parallel in different pluralities of wells of the multiwell plate and different types of readouts can be obtained at one or more timepoints from different wells. The devices provided herein are configured to handle the multiwell plates provided herein and to read out different assays running in parallel in different pluralities of wells on a multiwell plate provided herein. In some embodiments of the methods provided herein, the sample of a single patient is analyzed in parallel for a plurality of analytes in a multiwell plate provided herein. The systems, devices and methods described herein enable "spatial multiplexing," i.e., the parallel performance of different analytical assays on the same blood sample in different wells of the same multiwell plate.

Traditional multiwell plates (e.g., Corning® 96 well, 384 well or 1536 well plates) are commonly designed to have a single plurality of identical reaction wells. For example, all reaction wells on a traditional multiwell plate typically share the same geometry, dimensions, surface properties, optical properties, or surface coating. Traditional uses of a multiwell plate (e.g., high-throughput screening of small molecule libraries against a molecular drug target, biomarker testing) tend to involve performing essentially the same test in many or all of the wells of a multiwell plate. In a clinical setting, traditional uses of multiwell plates commonly involve the testing of samples from different patients against the same assay in essentially every well of the multiwell plate (except, e.g., in certain control wells). In some traditional multianalyte assays multiple analytes can be detected in parallel (e.g., in the same well) using variations of the same assay readout (e.g., different fluorescence wavelengths; e.g., Bio Rad's Bio-Plex® platform). Such traditional multianalyte assays typically involve the use of traditional multiwell plates featuring identical well types or the detection of related analytes (e.g., multiple protein analytes, such as cytokines, or multiple cell types, such as different types of blood cells).

In DTC diagnostics applications, the use of traditional multiwell plates would likely mean that samples from multiple consumers have to be collected before an assay is run to effectively use the full capacity of the multiwell plate. Such multiwell plate use would be undesirable, e.g., in a DTC diagnostics system at a point of consumer contact, such as in a general store, due to resulting delays in testing, need for sample storage, and the like. By contrast, the systems, devices and methods provided herein allow for the instantaneous initiation of testing of a sample collected from a single consumer against a complete multianalyte panel, without the need to collect additional samples, e.g., from other consumers. The systems, devices and methods provided herein, allow for the parallel testing of a diverse set of analytes of different chemistries (e.g., small molecule, protein, cell) and concentration ranges (e.g., blood glucose and cytokine) on a single multiwell plate.

The present disclosure is further based, in part, on the realization that an important aspect of developing the field of DTC diagnostics is to develop new systems, devices and methods to perform POCC testing with improved accuracy and robustness. To further improve the accuracy and robustness of POCC testing, the systems, devices and methods provided herein can include one or more quality control, assay standardization, or artifact reduction features. For example, consumer samples can be tested for sample integrity prior to testing analytes of interest to a consumer. Also, device configurations and assay technologies can be selected to improve assay robustness and accuracy. Systems, devices and methods that can provide high-quality data, especially in a POCC setting, are expected to further grow consumer acceptance of and consumer interest in DTC diagnostics. Moreover, high-quality DTC diagnostics data can be instrumental in broadening the use of such data, e.g., for medical research or drug development purposes, or for epidemiological studies.

5.1 Multiwell Plates

In one aspect, provided herein is a multiwell plate comprising two or more different pluralities of wells. In some embodiments, the multiwell plate can facilitate the parallel performance of two or more different assay formats (e.g., a fluorescence and absorbance based format) or to facilitate the performance of different assays for two or more different analytes in a sample (e.g., a high-abundance and a low-abundance analyte). Each of the different pluralities of wells can differ with respect to one or more properties affecting the performance of an assay, e.g., a biochemical assay or a cell-based assay, such as an optical property, geometry or shape, dimension, surface property, or assay reagent content. Typically, the properties of each of the different pluralities of wells are selected to improve the performance of a specific assay format (e.g., homogeneous, heterogeneous, biochemical, cell-based, and the like), or of an assay of a given format for a specific analyte (e.g., a high-abundance and a low-abundance analyte).

In some embodiments, the two or more different pluralities of wells are located on two or more different subcomponents of a multiwell plate provided herein ("chips"). In some embodiments, one or more of the subcomponents are removably attached to a carrier component of the multiwell plate, e.g., using a magnet. See, e.g., FIG. 6A. In some embodiments, the carrier component comprises two or more subcomponents, wherein each subcomponent comprises one or more pluralities of wells. In some embodiments, different subcomponents comprise the same pluralities of wells. See, e.g., FIG. 7. In some embodiments, different subcomponents comprise different pluralities of wells. See, e.g., FIG. 9. In some embodiments, one or more subcomponents comprise different pluralities of wells. See, e.g., FIG. 9, FIG. 11A, FIG. 14B, or FIG. 14L.

Figure 5A:
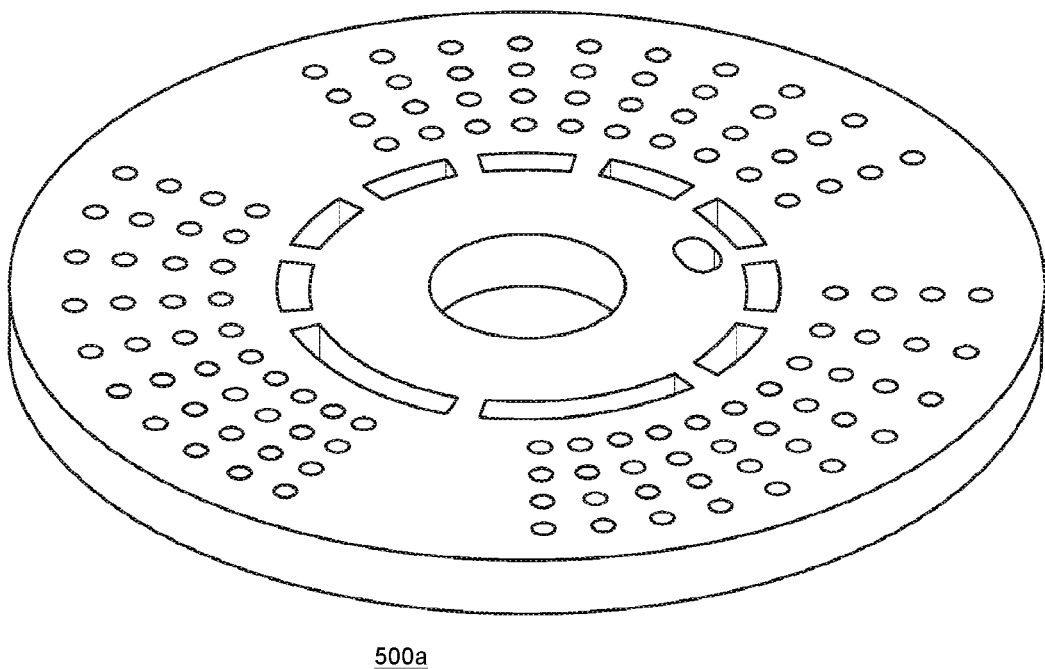
FIG. 5A and FIG. 5B show drawings illustrating exemplary one-piece multiwell plates provided herein ("cartridges").

In another aspect, provided herein is a circular multiwell plate comprising one or more pluralities of wells. See, e.g., FIG. 5A or FIG. 6A. In some embodiments, the circular multiwell plate comprises two or more different pluralities of wells. In some embodiments, the pluralities of wells on the multiwell plate are arranged in concentric circles around the center of the plate. In some embodiments, the pluralities of wells are organized in a spokes-like arrangement pointing from the center of the circular multiwell plate to the periphery. In some embodiments, the circular multiwell plate comprises one or more subcomponents ("chips") that each comprise one or more pluralities of wells and that are removably attached to a carrier component of the multiwell plate. See, e.g., FIG. 6A, FIG. 6B, or FIG. 6C. In some embodiments, one or more subcomponents comprise two or more different pluralities of well. See, e.g., FIG. 9. In some embodiments, two or more subcomponents ("chips") of a multiwell plate comprise different pluralities of well. See, e.g., FIG. 9.

As used herein, the term "wells," when used in connection with the two or more pluralities of wells of a multiwell plate provided herein, refers to wells for performing an analytical assay determine the concentration of an analyte of interest. In this context the term "wells" is used synonymously with "assay wells." Assay wells can include control wells, such as negative control wells that do not comprise an analyte, or other control wells that comprise known amounts of an analyte as a reference, e.g., to generate a standard curve. The pluralities of wells described herein do not include other well-like structures that may be present on a multiwell plate provided herein that are not used as assay wells. For example, the pluralities of wells do not include structures such as "moats" that may surround assay wells on a multiwell plate and that may facilitate the reduction of liquid evaporation from assay wells, e.g., to reduce edge effects in assays performed on a multiwell plate. See, e.g., US 2015/0343439 A1 (describing a moat structure surrounding a column of wells in a multiwell plate). The pluralities of wells do not include well-like structures, such as troughs, used to store bulk reagents, such as assay buffers, or samples on a well. The pluralities of wells do not include well-like structures, used to process assay reagents or samples on the multiwell plate, e.g., structures used to dilute reagents or samples prior to their addition to an assay well.

In some embodiments, the properties of the wells on a multiwell plate provided herein (e.g., well volume) and the assay selected to detect an analyte of interest (e.g., assay's lower limit of detection, sample dilution) in such wells are guided by Poisson statistics to ensure that a robust signal can be detected for the analyte taking into consideration the analyte's expected concentration in the analyzed sample. See, e.g., Alvarez J., (2007) Poisson-based detection limit and signal confidence intervals for a few total counts. Health Phys. 93(2), 120-126. For example, a high abundance analyte can be detected in a low-volume well using an assay having a high limit of detection to obtain an assay signal for the analyte in a sample that is at least 3σ-above background (e.g., the signal from a negative control well in which no analyte is present). A low abundance analyte can be detected, e.g., in a high-volume well using an assay having a low-limit of detection to obtain an assay signal for the analyte in a sample that is at least 3σ-above background.

In some embodiments, the properties of the different pluralities of wells on a multiwell plate provided herein are be selected, e.g., based on the expected analyte abundance in a sample (e.g., based on literature values), the format and detection limit of an analyte assay, and the analyte composition of a multianalyte panel to be assayed in a sample (e.g., as selected by a consumer). For example, a multiwell plate useful to assay a multianalyte panel comprising a low-abundance protein analyte (e.g., a cytokine), a high-abundance protein (e.g., albumin) and a low abundance cell (e.g., a T-cell) can comprise a different combination of wells with different properties compared to a multiwell plate useful to assay a multianalyte panel comprising a high-abundance small molecule analyte (e.g., blood glucose), a low-abundance protein (e.g., a cytokine) and a high-abundance cell (e.g., a red blood cell).

The different pluralities of wells on a multiwell plate provided herein can differ with respect to any property affecting the performance of an assay. The performance of an assay can be affected, e.g., with respect to the assay's sensitivity of analyte detection (e.g., lower limit of detection), robustness (e.g., Z-factor), signal intensity (e.g., absolute signal or relative to a positive or negative control), background signal (e.g., signal of a negative control well without analyte of interest), signal-to-noise ratio (S/N), signal variability (e.g., standard deviation of positive or negative control wells), reproducibility, temperature or light-sensitivity, sensitivity to interference from certain chemicals (e.g., fluorescent compounds, colored compounds, oxidizing or reducing compounds, detergents) or another factor.

In some embodiments, the property of a well affecting the performance of an assay comprises the well geometry (e.g., cube, rectangular cuboid or rectangular prism, sphere, cylinder, (inverted) pyramid, (inverted) cone, flat bottom, conical bottom, and the like), a well dimension (e.g., height, length, depth, or volume), an optical property of the well (e.g., light transparency or color), a surface property (e.g., high-binding (e.g., high protein-binding, high nucleic acid-binding), low-binding (e.g., low protein-binding, low nucleic acid-binding, beads in wells), cell-adhesion or cell-proliferation promoting, porous (e.g., glass filter or PVDF membrane) or non-permeable), temperature (e.g., room temperature, elevated or reduced temperature), or assay reagent content (e.g., assay reagents dried in a well or assay reagents in solution).

Exemplary assays that can be performed in the multiwell plates described herein and multiwell properties affecting such assays are described, e.g., in Taosheng Chen, A Practical Guide To Assay Development and High-Throughput Screening in Drug Discovery, CRC Press, 1st ed., 2009; Lisa K. Minor, Handbook of Assay Development in Drug Discovery, CRC Press, 1st ed., 2006; Ge Wu, Assay Development, Wiley, 1st ed., 2010; Uma Prabhakar, Validation of Cell-based Assays in the GLP Setting, Wiley, 1st ed., 2008; Masood Kahn and John Findlay, Ligand-Binding Assays, Wiledy, 1st ed., 2009; David Wild, Immunoassays, Elsevier Science; 4th ed., 2013, and Benjamin Blass, Basic Principles of Drug Discovery and Development, Academic Press, 1st ed., 2015, which are hereby incorporated herein by referenced in their entirety.

The two or more different pluralities of wells can arranged on a multiwell plate in a variety of different arrangements. In some embodiments, the two or more different pluralities of wells are arranged in columns and rows (e.g., forming a rectangle or a square), e.g., with each column or row comprising one of the different pluralities of wells. In some embodiments, the two or more different pluralities of wells are arranged in concentric circles or ovals around the center of the well. The different pluralities of wells arranged in rectangular or circular formation can be arranged on a multiwell plate having any shape, including a rectangular shape (e.g., a square) or a circular shape (e.g., a disk). In some embodiments, the different pluralities of wells can be arranged such that the wells of two or more different pluralities of wells alternate, e.g., in a circular arrangement, or a row or column (e.g., an A-B-A-B-A-B arrangement or A-B-C-A-B-C arrangement, of wells of two or three different pluralities of wells A, B, C). In some embodiments, the two or more different pluralities of wells can be arranged in a random order on a multiwell plate provided herein. In some embodiments, the arrangement of the two or more different pluralities of wells on the multiwell plate is encoded on a barcode (e.g., a two- or three dimensional barcode) on the multiwell plate.

The term "traditional multiwell plate," as used herein, refers to a multiwell plate comprising only a single plurality of essentially identical wells. Traditional multiwell plates include, e.g., traditional 96-well, 384-well, or 1536-well plates. The wells of different traditional multiwell plates can have different properties, such as different optical properties, shapes or different surface coatings. Different traditional multiwell plates can be optimized for different assay formats or different analytes. For example, traditional multiwell plates include plates wherein all wells have clear or translucent bottoms (e.g., Corning® 96 well plates, clear bottom; Corning® 96 well plates, UV-translucent; Greiner® Sensoplate™ glass bottom multiwell plates; Greiner polypropylene multiwell plates, including black, clear, green, red, yellow), all wells have opaque bottoms (e.g., Corning® 96 well plates, opaque (white or black)), all wells have non-binding (e.g., non protein or nucleotide-binding) surfaces (e.g., Corning® 96 well or 384 well plates, non-binding surface, Corning® Costar® ultra-low attachment multiwell plate), all wells have high-binding (e.g., high protein or nucleotide-binding) surfaces (e.g., Nunc-Immuno™ or MaxiSorp™ 96 well or 384 well plates; Greiner® high and medium-binding 96 well, 384 well, or 1536 well plates, Corning® Sulfhydryl-BIND™, Universal-BIND™, Carbo-BIND™, or DNA-BIND™ surface 96 well plates), all wells have filter bottoms (Corning® filter plates; glass fiber or PVDF membrane), all wells have coatings to promote cell attachment or cell proliferation (e.g., Corning® osteo assay surface 96 well plates; Corning® CellBIND® 384 well plates), all wells are sterile (e.g., Corning® osteo assay surface 96 well plates; Corning® CellBIND® 384 well plates), all wells have round bottoms (e.g., Corning® 384 well polypropylene plates), or all wells have flat bottoms (e.g., Greiner® high and medium binding 96 well, 384 well, or 1536 well plates with clear, black or white bottoms).

In some embodiments, a multiwell plate provided herein comprises a plurality of wells configured for an absorbance-based assay and a different plurality of wells configured for a fluorescence-based assay. Wells configured for an absorbance-based assay can comprise, e.g., a clear or translucent bottom. Wells configured for a fluorescence-based assay can comprise, e.g., opaque (e.g., solid black or white) bottoms.

In some embodiments, a multiwell plate comprises a plurality of wells configured for a heterogeneous assay (e.g., ELISA) and a different plurality of wells configured for a homogeneous assay (e.g., an enzymatic assay). Wells configured for a heterogeneous assay can, e.g., comprise a high-protein or high-nucleotide binding well surface. Wells configured for a homogeneous assay can comprise, e.g., a low-protein binding or low nucleotide-binding surface.

In some embodiments, a multiwell plate comprises a plurality of wells configured for a cell-based assay (e.g., adherent cell or suspension cell-based assay) and a different plurality of wells configured for a biochemical assay (e.g., enzyme-substrate turnover assay). Wells configured for a cell-based assay can, e.g., be sterile or comprise a surface promoting cell attachment, cell differentiation, or cell proliferation (e.g., fibronectin coating). Wells configured for a biochemical assay can comprise, e.g., low-protein binding or low nucleotide-binding surfaces.

In some embodiments, a multiwell plate comprises a plurality of wells configured for an assay analyzing a highly abundant analyte (e.g., blood glucose) and a different plurality of wells configured for an assay analyzing a low-abundance analyte (e.g., a cytokine). Wells configured for an assay analyzing a highly abundant analyte can, e.g., comprise a reagent (e.g., a dried reagent) for an assay having a high limit of detection. Wells configured for an assay analyzing a low-abundance analyte can, e.g., comprise a reagent (e.g., a dried reagent) for an assay having a low limit of detection.

In some embodiments, the multiwell plate comprises one or more pluralities of wells configured for an absorbance based assay and one or more different pluralities of wells configured for a fluorescence based assay. In some embodiments, one or more pluralities of wells configured for the absorbance based assay are arranged in a circle of wells on the periphery of a circular (e.g., disk shaped) multiwell plate. In some embodiments, the wells arranged on the periphery of a circular multiwell plate have a diameter of between 0.5 mm and 3.0 mm (e.g., 1.5 mm). In some embodiments, the wells arranged on the periphery of the circular multiwell plate comprise 24 wells. In some embodiments, the one or more pluralities of wells configured for an absorbance based assay comprise one or more pluralities of wells configured for a cell-based assay (e.g., RBC assay). In some embodiments, the one or more pluralities of wells configured for an absorbance based assay comprise one or more pluralities of wells configured for a biochemical assay. In some embodiments, the one or more pluralities of wells configured for a biochemical assay comprise one or more pluralities of wells configured for a homogeneous assay (e.g., protein detection, such as general protein absorbance (280 nm) or hemoglobin absorbance 540 nm-600 nm range (e.g., hemoglobin, oxyhemoglobin, carboxyhemoglobin, methemoglobin)). In some embodiments, the one or more pluralities of wells configured for a biochemical assay comprise one or more pluralities of wells configured for a heterogeneous assay (e.g., ELISA). In some embodiments, the one or more pluralities of wells configured for a fluorescence-based assay comprise one or more pluralities of wells configured for a fluorescence-based cellular assay. In some embodiments, the fluorescence-based cellular assay can assay suspension cells, cells adhered to beads, or cells adhered to a well bottom. In some embodiments, the one or more pluralities of wells configured for a fluorescence-based assay comprise one or more pluralities of wells configured for a fluorescence-based biochemical assay. In some embodiments, the one or more pluralities of wells configured for a fluorescence-based biochemical assay comprise one or more pluralities of wells configured for a homogeneous fluorescence-based biochemical assay (e.g., an enzymatic substrate-turnover assay). In some embodiments, the one or more pluralities of wells configured for a fluorescence-based biochemical assay comprise one or more pluralities of wells configured for a heterogeneous fluorescence-based biochemical assay (e.g., ELISA). In some embodiments, the heterogeneous fluorescence-based biochemical assay involves analyte binding to a bead surface or well surface.

In some embodiments, the multiwell plate comprises one or more pluralities of wells configured for a cell-based assay and one or more different pluralities of wells configured for a biochemical assay. In some embodiments, the one or more pluralities of wells configured for a cell-based assay comprise one or more pluralities of wells configured for a fluorescence-based cellular assay. In some embodiments, the fluorescence-based cellular assay can assay suspension cells or cells attached to the surface of a bead or well. In some embodiments, the one or more pluralities of wells configured for a cell-based assay comprise one or more pluralities of wells configured for an absorbance-based cellular assay.

In some embodiments, the one or more pluralities of wells configured for a biochemical assay comprise one or more pluralities of wells configured for a homogeneous biochemical assay. In some embodiments, the one or more pluralities of wells configured for a homogeneous biochemical assay comprise one or more pluralities of wells configured for a homogeneous fluorescence-based biochemical assay. In some embodiments, the one or more pluralities of wells configured for a homogeneous biochemical assay comprise one or more pluralities of wells configured for a homogeneous absorbance-based biochemical assay. In some embodiments, one or more pluralities of wells configured for a biochemical assay comprise one or more pluralities of wells configured for a heterogeneous biochemical assay. In some embodiments, the plurality of wells configured for a heterogeneous biochemical assays comprise one or more pluralities of wells configured for a fluorescence-based heterogeneous biochemical assay. In some embodiments, the one or more pluralities of wells configured for a heterogeneous biochemical assay comprise one or more pluralities of wells configured for an absorbance-based heterogeneous biochemical assay. In some embodiments, one or more of the pluralities of wells configured for an absorbance based assay are arranged in a circle of wells on the periphery of a circular (e.g., disk shaped) multiwell plate. In some embodiments, the wells arranged on the periphery of a circular multiwell plate have a diameter of between about 0.5 mm and 3.0 mm (e.g., 1.5 mm). In some embodiments, the wells arranged on the periphery of the circular multiwell plate comprise 24 wells.

In some embodiments, the multiwell plate comprises two or more different pluralities of wells configured to analyze two or more analytes selected from a small molecule analyte (e.g., a monosaccharide, fatty acid, salt, drug), a large molecule analyte (e.g., a protein, phospholipid, nucleic acid), and a cell (e.g., a red blood cell, a white blood cell).

In some embodiments, the multiwell plate comprises one or more pluralities of wells configured for an assay for detecting a cell (e.g., RBC, WBC, circulating cancer cell (CTC), bacterial cell), and one or more different pluralities of wells configured for an assay for detecting a large molecule analyte (e.g., a protein analyte). In some embodiments, the multiwell plate comprises one or more pluralities of wells configured for an assay for detecting a cell (e.g., a RBC, a WBC, a circulating cancer cell (CTC), a bacterial cell), one or more different pluralities of wells configured for an assay for detecting a large molecule analyte (e.g., a protein analyte), and one or more different pluralities of wells configured for an assay for detecting a small molecule analyte (e.g., glucose or cholesterol).

In some embodiments, the multiwell plate comprises one or more pluralities of wells configured for an assay for detecting a high abundance analyte (e.g., albumin, glucose or a RBC) and one or more different pluralities of wells configured for an assay for detecting a medium- or low-abundance analyte (e.g., tumor necrosis factor alpha (TNFα) or a CTC).

In some embodiments, the configuration of the two or more different pluralities of wells (e.g., the wells arrangement on the multiwell plate, some or all well properties) is encoded in a barcode (e.g., a two-dimensional or three-dimensional barcode) on the multiwell plate.

In some embodiments, two or more different pluralities of wells on a multiwell plate differ with respect to their reagent content. In some embodiments, the two or more different pluralities of wells differing with respect to their reagent content do not comprise control wells (e.g., negative control wells, such as wells lacking an assay reagent, or positive control wells, such as wells including a positive control analyte). In some embodiments, the two or more different pluralities of wells differ with respect to the content of 1 or more, 2 or more, 3 or more, 4 or more, 5 or more, 6 or more, 7 or more, 8 or more, 9 or more, 10 or more, 12 or more, 15 or more, 20 or more, 25 or more 30 or more, 40 or more, or 50 or more reagents (e.g., 1, 2, 3, 4, 5, 6, 7, 8, 9, 10, 50, 100, reagents, or the like).

In some embodiments, two or more different pluralities of wells on a multiwell plate differ with respect to at least one property other than their assay reagent content. In some embodiments, two or more different pluralities of wells on the multiwell plate differ with respect to at least one property other than an optical property (e.g., clear, translucent, or opaque bottom). In some embodiments, two or more different pluralities of wells on the multiwell plate differ with respect to at least one property other than a well dimension or well shape. In some embodiments, two or more different pluralities of wells on the multiwell plate differ with respect to a property other than a surface property (e.g., high or low protein binding).

In some embodiments, a well configured for a heterogeneous assay comprises one or more surfaces that are modified to promote binding of a biomolecule, e.g., a protein or nucleic acid, or of a cell (e.g., mammalian or bacterial cell), relative to an unmodified surface (e.g., an unmodified polystyrene or polypropylene surface). In some embodiments, high binding surfaces can bind>100 ng/cm$^2$, >200 ng/cm$^2$, >300 ng/cm$^2$, >400 ng/cm$^2$, >500 ng/cm$^2$, >600 ng/cm$^2$>700 ng/cm$^2$, >800 ng/cm$^2$, >900 ng/cm$^2$, or >1,000 ng/cm$^2$, e.g., of a protein, nucleic acid or other biomolecule (e.g., sugar, lipid, metabolite, or the like). In some embodiments, high-binding surfaces are chemically or physically modified. For example, a high-binding surface can comprise a chemical crosslinker (e.g., a UV crosslinker) that can react with a biomolecule (e.g., protein, nucleic acid, lipid, sugar, metabolite or the like) to form a covalent bond and immobilize the biomolecule on the surface. In some embodiments, the high-binding surface comprises a maleimide, hydrazide, nickel-chelate, biotin, or another small molecule reagent capable of binding a biomolecule covalently or non-covalently (e.g., a receptor ligand). In some embodiments, the high-binding surface is coated with a binding protein (e.g., protein A, protein G, streptavidin, antibody, biotin, collagen I, or the like) or capture probe (e.g., oligonucleotide capture probe or RNA aptamer) that can facilitate the immobilization of another binding protein (e.g., antibody), analyte (e.g., antigen), or cell (e.g., blood cell). In some embodiments, the modified surface is an inner surface of the well (e.g., well wall or well bottom surface). In some embodiments, the modified surface is the surface of a bead in the well (e.g., a well with a low-biomolecule binding surface). In some embodiments, a well configured for a heterogeneous assay comprises a bead that is modified to capture a biomolecule or reagent (e.g., streptavidin or antibody coated, biotinylated, comprising reactive maleimides or another chemical crosslinker). In some embodiments, a well configured for a heterogeneous assay comprises a bottom comprising a glass fiber filter membrane.

In some embodiments, a well configured for a homogeneous assay comprises well surfaces that are non-binding or low-binding surfaces, e.g., low protein-binding or low-nucleotide binding. In some embodiments, non-binding or low-binding surfaces are treated or modified to reduce the binding of a biomolecule (e.g., protein, nucleic acid, lipid, sugar, or the like). Non-binding surfaces can include, e.g., modified polymer surfaces, such as a non-ionic hydrophilic surface (polyethylene oxide-like). In some embodiments, non-binding or low-binding surfaces can bind<1 ng/cm$^2$, <2 ng/cm$^2$, <3 ng/cm$^2$, <4 ng/cm$^2$, <5 ng/cm$^2$, <6 ng/cm$^2$, <7 ng/cm$^2$, <9 ng/cm$^2$, <10 ng/cm$^2$, <15 ng/cm$^2$, <20 ng/cm$^2$, <25 ng/cm$^2$, <30 ng/cm$^2$, <40 ng/cm$^2$ or <50 ng/cm$^2$ of a biomolecule, such as a protein or nucleotide. In some embodiments, non-binding or low-binding surfaces can have reduced biomolecule binding, e.g., reduced protein or nucleic acid binding relative to an untreated polystyrene or untreated polypropylene surface (e.g., >50%, >60%, >70%, >80% or >90% reduced). In some embodiments, non-binding or low-binding surfaces can inhibit (e.g., slow down or reduce) the adhesion of a cell line (e.g., HEK293, HeLa, CHO, HCT199 cell line) or blood cell (e.g., RBC, WBC) relative to an untreated polystyrene or an untreated polypropylene surface. In some embodiments, a well configured for a homogeneous assay comprises untreated well surfaces, e.g., untreated polystyrene or untreated polypropylene surfaces, such as well surfaces that are not treated or modified to increase the binding of a protein (e.g., antibody), nucleic acid (e.g., oligonucleotide capture probe), or cell (e.g., RBC or WBC). In some embodiments, a well configured for a homogeneous assay comprises one or more soluble assay reagents (e.g., a soluble enzyme or a soluble enzyme substrate), e.g., as dried reagents or as reagents in solution (e.g., an assay buffer). In some embodiments, a well configured for a homogeneous assay comprises a bottom comprising a polyvinylidene fluoride (PVDF) membrane.

In some embodiments, a well configured for an absorbance assay comprises a translucent well bottom (e.g., a well bottom allowing transmission of light of a wavelength in an ultraviolet-visible spectrum, e.g., 200-850 nm, 300 nm-850 nm, or 400-800 nm). In some embodiments, the translucent well bottom is a glass, polystyrene or polypropylene bottom. In some embodiments, the translucent well bottom is clear. In some embodiments, the translucent well bottom is colored (e.g., yellow, red, blue) In some embodiments, a well configured for an absorbance assay has an elongated shape (e.g., cylindrical shape with greater depth than diameter), e.g., to extend the length of an optical path through the well for a given well volume. In some embodiments, a well configured for an absorbance assay comprises an enzyme substrate whose absorbance characteristics change upon enzyme-mediated substrate turnover.

In some embodiments, a well configured for a fluorescence based assay comprises a well bottom and well walls that transmit no, or reduced levels (e.g., less than 50%, less than 40%, less than 30%, less than 20%, less than 10%, less than 5%, less than 3%, or less than 1%) of light of a wavelength in the ultraviolet or visible spectrum (e.g., opaque, solid black or solid white materials). In some embodiments, a well configured for a fluorescence assay (e.g., a fluorescence intensity assay) comprises an enzyme substrate the fluorescence characteristics of which change upon an enzyme-mediated substrate turnover. In some embodiments, a well configured for a fluorescence assay (e.g., a (time-resolved) fluorescence resonance energy transfer assay (TR-FRET)) comprise a fluorescence donor and a fluorescence acceptor reagent, the average proximity of which changes as a result of an analyte detection event, which facilitates energy transfer from the donor to the acceptor reagent.

In some embodiments, a well configured for a cell-based assay (e.g., a cell enumeration assay), comprises a well bottom that is modified to facilitate cell attachment (e.g., collagen I or fibronectin coating). In some embodiments, a well configured for a cell-based assays comprises surfaces modified to prevent cell attachment. In some embodiments, a well configured for a cell-based assay is sterile (e.g., sterilized through irradiation; maintained in a sterile form, e.g., by covering sterile well with a lid, foil, membrane, or the like). In some embodiments, the bottom of a well configured for a cell-based assay comprises a membrane, e.g., a porous membrane (e.g., a PVDF membrane or glass fiber filter). The membrane pore sizes can be selected to allow for fluid and molecular exchange with the environment, while preventing cell loss (e.g., average pore sizes between about 0.2 m and about 0.45 μm in pore diameter).

In some embodiments, the two or more different pluralities of wells on a multiwell plate comprise 3 or more, 4 or more, 5 or more, 6 or more, 7 or more, 8 or more, 9 or more, or 10 or more different pluralities of wells.

In some embodiments, one or more of the different pluralities of wells comprise 2 or more, 3 or more, 4 or more, 5 or more, 6 or more, 7 or more, 8 or more, 9 or more, 10 or more, 15 or more, 20 or more, 25 or more, 30 or more, 35 or more, 40 or more, 45 or more, 50 or more, 60 or more, 70 or more, 80 or more, 90 or more, or 100 or more wells. In some embodiments, one or more of the different pluralities of wells comprise 24 wells.

In some embodiments, one or more of the different pluralities of wells comprise between 2 and 100 wells, between 4 and 90 wells, between 6 and 80 wells, between 8 and 70 wells, between 10 and 60 wells, between 15 and 50 wells, or between 20 and 40 wells.

In some embodiments, one or more of the different pluralities of wells comprise between 1 and 20 wells. In some embodiments, one or more of the different pluralities of wells comprise between 1 and 40 wells. In some embodiments, one or more of the different pluralities of wells comprise between 1 and 80 wells. In some embodiments, one or more of the different pluralities of wells comprise between 1 and 10 wells.

In some embodiments, a multiwell plate comprises a first plurality of wells comprising between 1 and 20 wells and a different second plurality of wells comprising between 1 and 40 wells. In some embodiments, the multiwell comprises an different third plurality of wells comprising between 1 and 80 wells. In some embodiments, the multiwell plate comprises a different fourth plurality of wells comprising between 1 and 10 wells.

In some embodiments, one or more or the different pluralities of wells comprise a volume of about 10 μl or less, about 9 μl or less, about 8 μl or less, about 7 μl or less, about 6 μl or less, about 5 μl or less, about 4 μl or less, about 3 μl or less, about 2 μl or less, or about 1 μl or less.

In some embodiments, one or more of the different pluralities of wells comprise a volume of between about 1 μl and about 20 μl, between about 2 μl and about 18 μl, between about 3 μl and about 16 μl, between about 4 μl and about 14 μl, between about 5 μl and about 12 μl, between about 6 μl and about 10 μl, or between 8 μl and about 10 μl.

In some embodiments, one or more of the different pluralities of wells comprise a volume of between 1.0 μl and 5.0 μl. In some embodiments, one or more of the different pluralities of wells comprise a volume of between 5.0 μl and 10.0 μl. In some embodiments, one or more of the different pluralities of wells comprise a volume of between 10.0 μl and 20.0 μl. In some embodiments, one or more of the different pluralities of wells comprise a volume of between 20.0 μl and 50.0 μl.

In some embodiments, a multiwell plate comprises a first plurality of wells comprising a volume of between 1.0 μl and 5.0 μl and a different second plurality of wells comprising a volume of between 5.0 μl and 10.0 μl. In some embodiments, the multiwell plate comprises a different third plurality wells comprising a volume of between 10.0 μl and 20 μl. In some embodiments, the multiwell plate comprises a different fourth plurality of wells comprising a volume of between 20.0 and 50.0 μl.

In some embodiments, one or more of the different pluralities of wells comprise a length of about 10 mm or less, about 9 mm or less, about 8 mm or less, about 7 mm or less, about 6 mm or less, about 5 mm or less, about 4 mm or less, about 3 mm or less, about 2 mm or less, or about 1 mm or less.

In some embodiments, one or more of the different pluralities of wells comprise a length of between about 1 mm and about 20 mm, between about 2 mm and about 18 mm, between about 3 mm and about 16 mm, between about 4 mm and about 14 mm, between about 5 mm and about 12 mm, between about 6 mm and about 10 mm, or between 8 mm and about 10 mm.

In some embodiments, one or more of the different pluralities of wells comprise a length of between 0.5 mm and 2.0 mm. In some embodiments, one or more of the different pluralities of wells comprise a length of between 2 mm and 5 mm. In some embodiments, one or more of the different pluralities of wells comprise a length of between 5.0 mm and 10 mm. In some embodiments, one or more of the different pluralities of wells comprise a length of between 10 mm and 20 mm.

In some embodiments, a multiwell plate comprises a first plurality wells comprising a length of between 0.5 mm and 2.0 mm and a different second plurality of wells comprising a length of between 2.0 mm and 5.0 mm. In some embodiments, the multiwell plate comprises a different third plurality of wells comprising a length of between 5.0 mm and 10.0 mm. In some embodiments, the multiwell plate comprises a different fourth plurality of wells comprising a length of between 10.0 and 20.0 mm.

In some embodiments, one or more of the different pluralities of wells comprise a depth (or width) of about 10 mm or less, about 9 mm or less, about 8 mm or less, about 7 mm or less, about 6 mm or less, about 5 mm or less, about 4 mm or less, about 3 mm or less, about 2 mm or less, or about 1 mm or less.

In some embodiments, one or more of the different pluralities of wells comprise a depth (or width) of between about 1 mm and about 20 mm, between about 2 mm and about 18 mm, between about 3 mm and about 16 mm, between about 4 mm and about 14 mm, between about 5 mm and about 12 mm, between about 6 mm and about 10 mm, or between 8 mm and about 10 mm.

In some embodiments, one or more of the different pluralities of wells comprise a depth (or width) of between 0.5 mm and 2.0 mm. In some embodiments, one or more of the different pluralities of different wells comprises a depth of between 2.0 mm and 5.0 mm. In some embodiments, one or more of the different pluralities of wells comprise a depth of between 5.0 mm and 10.0 mm. In some embodiments, one or more of the different pluralities of wells comprise a depth of between 10.0 mm and 30.0 mm.

In some embodiments, a multiwell plate comprises a first plurality of wells comprising a depth (or width) of between 0.5 mm and 2.0 mm and a different second plurality of wells comprising a depth of between 2.0 and 5.0 mm. In some embodiments, the multiwell plate comprises a different third plurality of wells comprising a depth of between 5.0 mm and 10.0 mm. In some embodiments, the multiwell plate comprises a different fourth plurality of wells comprising a depth of between 10.0 and 30.0 mm.

In some embodiments, one or more of the different pluralities of wells comprise a height of about 10 mm or less, about 9 mm or less, about 8 mm or less, about 7 mm or less, about 6 mm or less, about 5 mm or less, about 4 mm or less, about 3 mm or less, about 2 mm or less, or about 1 mm or less.

In some embodiments, one or more of the different pluralities of wells comprise a height of between about 1 mm and about 20 mm, between about 2 mm and about 18 mm, between about 3 mm and about 16 mm, between about 4 mm and about 14 mm, between about 5 mm and about 12 mm, between about 6 mm and about 10 mm, or between 8 mm and about 10 mm.

In some embodiments, one or more of the different pluralities of wells comprise a height of between 5.0 mm and 7.0 mm.

In some embodiments, a multiwell plate comprises a first plurality of wells comprising a height of between 5.0 mm and 7.0 mm and a different second plurality of wells comprising a height of between 5.0 mm and 7.0 mm (e.g., differing from the first plurality of wells with respect to a property other than height). In some embodiments, the multiwell plate comprises a different third plurality of wells comprising a height of between 5.0 mm and 7.0 mm. In some embodiments, the multiwell plate comprises a different fourth plurality of wells comprising a height of between 5.0 mm and 7.0 mm.

In some embodiments, one or more of the different pluralities of wells comprise a diameter of about 10 mm or less, about 9 mm or less, about 8 mm or less, about 7 mm or less, about 6 mm or less, about 5 mm or less, about 4 mm or less, about 3 mm or less, about 2 mm or less, or about 1 mm or less.

In some embodiments, one or more of the different pluralities of wells comprise a diameter of between about 1 mm and about 20 mm, between about 2 mm and about 18 mm, between about 3 mm and about 16 mm, between about 4 mm and about 14 mm, between about 5 mm and about 12 mm, between about 6 mm and about 10 mm, or between 8 mm and about 10 mm.

In some embodiments, one or more of the different pluralities of wells comprises a diameter of between 5.0 mm and 7.0 mm. In some embodiments, one or more of the different pluralities of wells comprise a diameter of between 2.0 mm and 4.0 mm. In some embodiments, one or more of the different pluralities of wells comprise a diameter of between 7.0 mm and 10.0 mm. In some embodiments, one or more of the different pluralities of wells comprise a diameter of between 0.5 mm and 2.5 mm.

In some embodiments, a multiwell plate comprises a first plurality of wells comprising a diameter of between 5.0 mm and 7.0 mm and a different second plurality of wells comprising a diameter of between 2.0 mm and 7.0 mm. In some embodiments, the multiwell plate comprises a different third plurality of wells comprising a diameter of between 7.0 mm and 10.0 mm. In some embodiments, the multiwell plate comprises a different fourth plurality of wells comprising a diameter of between 0.5 mm and 2.5 mm.

In some embodiments, one or more of the different pluralities of wells comprises a length of between 1.0 mm and 10.0 mm, a depth of between 1.0 mm and 10.0 mm, and a height of between 5.0 mm and 7.0 mm.

In some embodiments, one or more of the different pluralities of wells comprises a diameter of between 0.5 mm and 10.0 mm and a height of between 5.0 mm and 7.0 mm.

In some embodiments, a multiwell plate comprises a first plurality of wells comprising a length of between 0.5 mm and 5.0 mm, a depth of between 0.5 mm and 5.0 mm, and a height of between 5.0 mm and 7.0 mm, and a different second plurality of wells comprising a length of between 5.0 and 10.0 mm, a depth of between 5.0 mm and 10 mm, and a height of between 5.0 mm and 7.0 mm.

In some embodiments, a multiwell plate comprises a first plurality of wells comprising a length of between 0.5 mm and 5.0 mm, a depth of between 0.5 mm and 5.0 mm, and a height of between 5.0 mm and 7.0 mm, a different second plurality of wells comprising a length of between 5.0 mm and 10.0 mm, a depth of between 5.0 mm and 10 mm, and a height of 5.0 mm and 7.0 mm, and a different third plurality of wells comprising a length of between 10.0 mm and 15.0 mm, a depth of between 10.0 mm and 15.0 mm, and a height of between 5.0 mm and 7.0 mm.

In some embodiments, a multiwell plate comprises a plurality wells comprising a diameter of between 0.5 mm and 5.0 mm, and a height of between 5.0 and 7.0 mm, and a different plurality of wells comprising a diameter of between 5.0 and 10.0 mm, and a height of between 5.0 and 7.0 mm.

In some embodiments, a multiwell plate comprises a first plurality wells comprising a diameter of between 0.5 mm and 5.0 mm, and a height of between 5.0 mm and 7.0 mm and a different second plurality wells comprising a diameter of between 5.0 mm and 10.0 mm, and a height of between 5.0 mm and 7.0 mm, and, optionally, a different third plurality of wells comprising a diameter of between 10.0 mm and 15.0 mm, and a height of between 5.0 mm and 7.0 mm.

In some embodiments, one or more of the different pluralities of wells are cylinders, rectangular cuboids, cubes, (inverted) cones, or (inverted) pyramids.

In some embodiments, one or more of the different pluralities of wells on a multiwell plate are cylindrical wells. In some embodiments, one or more of the different pluralities of wells are rectangular cuboid wells or cube-shaped wells. In some embodiments, one or more of the different pluralities of wells are cubes. In some embodiments, one or more of the different pluralities of wells are sphere-shaped or cylindrical and one or more of the different pluralities of wells are rectangular cuboids or cube-shaped. In some embodiments, one or more of the different pluralities of wells are cylinders and one or more of the different pluralities of wells are rectangular cuboids. In some embodiments, one or more of the different pluralities of wells are cubes and one or more of the different pluralities of wells are rectangular cuboids. In some embodiments, a first plurality of wells are cylinders, a different second plurality of wells are rectangular cuboids, and a different third plurality of wells are cubes. In some embodiments, all of the different pluralities of wells are cylinders. In some embodiments, all of the different pluralities of wells are rectangular cuboids. In some embodiments, all of the different pluralities of wells are cubes.

The wells of a plurality of wells can all have identical properties, or differ from one another with respect to one or more properties (e.g., reagent content). In some embodiments, all wells of one or more pluralities of wells have essentially identical properties. In some embodiments, two or more wells of one or more pluralities of wells share one or more properties (e.g., geometry, dimension) and are different with respect to one or more properties (e.g., optical property of well bottom or reagent content). In some embodiments, two or more wells of one or more pluralities of wells share the same geometry (e.g., cube, sphere, and the like) and differ with respect to their dimension (e.g., length, depth, height, diameter, or volume).

In some embodiments, a multiwell plate comprises one or more additional wells in addition to the two or more pluralities of different wells. In some embodiments, the additional well is larger (e.g., greater length, depth, height, diameter, or volume) than each of the wells of the two or more pluralities of different wells. In some embodiments, the one or more additional wells are 2 or more, 3 or more, 4 or more, 5 or more, 6 or more, 7 or more, 8 or more, 9 or more, or 10 or more additional wells. In some embodiments, all additional wells have essentially identical properties. In some embodiments, two or more additional wells are different from each other with respect to one or more properties (e.g., different, geometry, dimension, surface property, optical property, reagent content and the like). In some embodiments, all additional wells are different from each other with respect to at least one property.

In some embodiments, the multiwell plate has a circular shape (e.g., disc shape) or an ellipsoid shape. In some embodiments, the multiwell plate has a square or rectangular shape.

In some embodiments, one or more additional wells are located in or near the center of a circular multiwell plate. In some embodiments, an additional well is centered around a focal point of an ellipsoid multiwell plate. In some embodiments, an additional well is centered around each of the two focal points of an ellipsoid multiwell plate. In some embodiment one or more additional wells are located at the periphery of a circular multiwell plate. In some embodiments, one or more additional wells are located in between the center and the periphery of a circular multiwell plate. In some embodiments, one or more additional wells are located at the center of a circular multiwell plate and one or more additional well are located at the periphery of the circular multiwell plate. In some embodiments, one or more additional wells are located at the center of a circular multiwell plate, one or more additional wells are located at the periphery of the circular multiwell plate, and one or more additional wells are located in between the center and the periphery of the circular multiwell plate.

In some embodiments, the one or more additional well comprises an assay solution or a component of an assay solution (e.g., a dried buffer or salt). Assay solutions can comprise an assay buffer (e.g., a phosphate-buffered saline (PBS) buffer or Tris(hydroxymethyl)aminomethane (Tris) buffer, e.g., comprising magnesium ions, or a coenzyme, such as nicotinamide adenine dinucleotide (phosphate) (NAD(P)H)), adenine di- or tri nucleotide (ADP, ATP), or the like), a dilution buffer (e.g., enzyme or substrate dilution buffer, such as PBS or Tris), a wash buffer (e.g., for an ELISA, comprising a detergent, such as polysorbate (Tween® 20), an assay stop solution (e.g., hydrochloric acid, sodium peroxide, ethylenediaminetetraacetic acid (EDTA), or the like), or a cell culture medium (e.g., Dulbecco's Modified Eagle Medium (DMEM)). In some embodiments, the one or more additional well comprises a diluents, such as water or an organic solvent (e.g., dimethylsulfoxide (DMSO), dimethylformamide (DMF), acetone, ethanol, isopropanol, or tert-butanol).

In some embodiments, the multiwell plate has a circular shape and one or more of the two or more pluralities of different wells are arranged in a linear arrangement reaching from an inner to an outer position of the circular multiwell plate (e.g., spoke-like arrangement). In some embodiments, one or more pluralities of the different wells are arranged in a circular arrangement around the center of the circular multiwell plate (e.g., arrangement as concentric circles). See, e.g., FIG. 1. In some embodiments, the circular arrangement can be an ellipsoid arrangement. In some embodiments, wells arranged on two or more concentric circles on a multiwell plate can be arranged in parallel, e.g., in a spoke-like configuration on one line with the center of the circular multiwell plate. In some embodiments, wells arranged on two or more concentric circles on a multiwell plate can be staggered (e.g., offset relative to one another). In some embodiments, different concentric circles of wells can comprise the same number of wells or different numbers of wells.

In some embodiments, the multiwell plate, comprises a total of 10 or more, 20 or more, 30 or more, 40 or more, 50 or more, 60 or more, 70 or more, 80 or more, 90 or more, 100 or more, 120 or more, 140 or more, 160 or more, 180 or more, 200 or more, 250 or more, 300 or more, 350 or more, 400 or more, 450 or more, 500 or more, 600 or more, 700 or more, 800 or more, 900 or more, 1,000 or more, 2,000 or more, 3,000 or more, 4,000 or more, 5,000 or more, 6,000 or more, 7,000 or more, 8,000 or more, 9,000 or more, or 10,000 or more wells.

In some embodiments, a circular plate comprises two or more different pluralities of wells arranged in concentric circles, wherein one or more pluralities of wells comprise a well at every 1 degree (total of 360 wells per circle), every 2 degrees (total of 180 wells per circle), every 3 degrees (total of 120 wells per circle), every 4 degrees (total of 90 wells per circle), every 5 degrees (total of 72 wells per circle), every 6 degrees (total of 60 wells per circle), every 9 degrees (total of 40 wells per circle), every 10 degrees (total of 36 wells per circle), every 12 degrees (total of 30 wells per circle), every 15 degrees (total of 24 wells per circle), or every 20 degrees (total of 18 wells per circle).

In some embodiments, a circular multiwell plate comprises two or more pluralities of wells arranged in concentric circles, wherein one or more plurality of wells comprise between 10 and 500 wells, between 10 and 50 wells, between 50 and 100 wells, between 100 and 150, between 150 and 200, between 250 and 300, between 350 and 400, or between 450 and 500 wells arranged on a circle.

In some embodiments, a circular multiwell plate comprises two or more pluralities of wells arranged in concentric circles, wherein each concentric circle comprises the same number of wells. In some embodiments, a circular multiwell plate comprises two or more pluralities of wells arranged in concentric circles, wherein two or more concentric circles comprise different numbers of wells.

In some embodiments, the multiwell plate comprises a length of about 20 cm or less, about 18 cm or less, about 16 cm or less, about 14 cm or less, about 12 cm or less, about 10 cm or less, about 9 cm or less, about 8 cm or less, about 7 cm or less, about 6 cm or less, about 5 cm or less, about 4 cm or less, about 1 cm or less, or about 0.5 cm or less.

In some embodiments, the multiwell plate comprises a depth of about 20 cm or less, about 18 cm or less, about 16 cm or less, about 14 cm or less, about 12 cm or less, about 10 cm or less, about 9 cm or less, about 8 cm or less, about 7 cm or less, about 6 cm or less, about 5 cm or less, about 4 cm or less, about 1 cm or less, or about 0.5 cm or less.

In some embodiments, the multiwell plate comprises a diameter of about 20 cm or less, about 18 cm or less, about 16 cm or less, about 14 cm or less, about 12 cm or less, about 10 cm or less, about 9 cm or less, about 8 cm or less, about 7 cm or less, about 6 cm or less, about 5 cm or less, about 4 cm or less, about 1 cm or less, or about 0.5 cm or less.

In some embodiments, the multiwell plate comprises a height of about 5 cm or less, about 4.5 cm or less, about 4 cm or less, about 3.5 cm or less, about 3.0 cm or less, about 2.5 cm or less, about 2.0 cm or less, about 1.5 cm or less, about 1.0 cm or less, about 0.5 cm or less, about 0.4 cm or less, about 0.3 cm or less, about 0.2 cm or less, or about 0.1 cm or less.

In some embodiments, one or more pluralities of wells comprises a height of between about 1 mm and about 20 mm, between about 2 mm and about 18 mm, between about 3 mm and about 16 mm, between about 4 mm and about 14 mm, between about 5 mm and about 12 mm, between about 6 mm and about 10 mm, or between 8 mm and about 10 mm.

In some embodiments, one or more of the different pluralities of wells comprise one or more reagents for a biochemical assay. In some embodiments, the biochemical assay comprises turnover of an enzyme substrate. In some embodiments, the biochemical assay comprises binding of a binding reagent (e.g., antibody) to an analyte of interest (e.g., insulin, cytokine, or the like). In some embodiments, reagents for a biochemical assay comprise an enzyme or an enzyme substrate. In some embodiments, the enzyme substrate is a fluorescent substrate (i.e., a substrate that can change its fluorescence properties as a result of enzyme-mediated turnover). In some embodiments, the enzyme substrate can change its absorbance characteristics in the ultraviolet (e.g., 200 nm-400 nm) or visible spectrum (e.g., 350 nm-850 nm) as a result of enzyme-mediated turnover. In some embodiments, the biochemical assay is a binding assay (e.g., sandwich-immune assay, ELISA, or the like). In some embodiments, the biochemical assay is a competition assay (e.g., immunoassay for a steroid hormone). In some embodiments, the biochemical assay is a homogeneous assay (e.g., (TR-)FRET assay, enzyme-substrate turnover assay, or the like). In some embodiments, the biochemical assay is as heterogeneous assay (e.g., ELISA). In some embodiments, the biochemical assay is a kinetic assay (e.g., continuous-read or intermittent-read). In some embodiments, the biochemical assay is an endpoint assay. In some embodiments, the biochemical assay reagent is coated on the surface of a plurality of wells (e.g., a capture or binding reagents, such as an antibody, streptavidin, protein A, protein G, aptamer, oligonucleotide capture probe, or the like). In some embodiments, the biochemical assay reagent is a dried reagent (e.g., to facilitate long-term storage). In some embodiments, the biochemical assay reagent is in solution (e.g., dissolved in an aqueous buffer or an organic solvent).

In some embodiments, one or more of the different pluralities of wells comprise one or more reagents for a cell-based assay. In some embodiments, the cell-based assay comprises binding of a binding reagent (e.g., a fluorescence-labeled antibody) to a cell-surface marker (e.g., CD20, CD45, or the like). In some embodiments, reagents for a cell-based assay comprise a labeled cell-specific binding reagent (e.g., a fluorescence-labeled anti-CD20 antibody) or a bead coated with a cell-specific binding reagent (e.g., an antibody directed to a cell-surface marker, e.g., anti-CD20 antibody). In some embodiments, reagents for a cell-based assay comprise a cell (e.g., mammalian, bacterial, yeast cell, or the like). In some embodiments, the cell is an adherent cell (e.g., a solid tumor-derived cell). In some embodiments, the cell is a suspension cell (e.g., red blood cell (RBC), white blood cell (WBC), circulating tumor cell (CTC), or the like). In some embodiments, the cell is a mammalian cell (e.g., a human, primate, hamster, mouse, rat and the like). In some embodiments, the cell is a yeast cell. In some embodiments, the cell is a bacterial cell (e.g., gram-positive or negative).

In some embodiments, the cell is a recombinant cell. In some embodiments, the cell-based assay is a reporter gene-assay. In some embodiments, the reporter-gene is luciferase. In some embodiments, the cell-based assay is a cell-enumeration assay. In some embodiments, the cell-based assay reagent is a dried reagent (e.g., to facilitate long-term storage). In some embodiments, the cell-based assay reagent is in solution (e.g., dissolved in an aqueous buffer, organic solvent or a tissue culture medium).

In some embodiments, one or more of the different pluralities of wells comprise one or more reagents for a homogeneous assay. In some embodiments, the homogeneous assay is a biochemical assay. In some embodiments, the homogeneous assays is a cell-based assay using suspension cells.

In some embodiments, one or more of the different pluralities of wells comprise one or more reagents for a heterogeneous assay. In some embodiments, the reagents for a heterogeneous assay comprise a bead or a well surface with an immobilized analyte-specific binding reagent (e.g., a covalently bound or physically adsorbed antibody, biotin, or other binding reagent) or a soluble analyte specific binding reagent (e.g., a fluorescence-labeled or enzyme-conjugated antibody, biotin, or other binding reagent).

In some embodiments, a first plurality of wells comprise one or more reagents for a cell-based fluorescence assay (e.g., WBC enumeration). In some embodiments a first plurality of wells comprise one or more reagents for a cell-based fluorescence assay and a different second plurality of wells comprise one or more reagents for a fluorescence based biochemical assay (e.g., for blood glucose). In some embodiments, the fluorescence based biochemical assay is a homogeneous assay (e.g., for blood glucose). In some embodiments, the fluorescence based biochemical assay is a heterogeneous assay (e.g., for insulin, a cytokine, or the like). In some embodiments a first plurality of wells comprise one or more reagents for a cell-based fluorescence assay, a different second plurality of wells comprise one or more reagents for a fluorescence based biochemical assay and a different third plurality of wells comprise one or more reagents for an absorbance based biochemical assay. In some embodiments, one or more reagents are dried reagents.

In some embodiments, a first plurality of wells comprise one or more reagents for an absorbance based cellular assay (e.g., RBC enumeration). In some embodiments a first plurality of wells comprise one or more reagents for an absorbance based cellular assay (e.g., RBC enumeration) and a different second plurality of wells comprise one or more reagents for a fluorescence based biochemical assay (e.g., for blood glucose). In some embodiments, the fluorescence based biochemical assay is a homogeneous assay (e.g., for blood glucose). In some embodiments, the fluorescence based biochemical assay is a heterogeneous assay (e.g., for insulin, a cytokine, or the like). In some embodiments a first plurality of wells comprise one or more reagents for an absorbance based cellular assay, a different second plurality of wells comprise one or more reagents for a heterogeneous fluorescence based biochemical assay and a different third plurality of wells comprise one or more reagents for a homogeneous fluorescence based biochemical assay. In some embodiments, one or more reagents are dried reagents.

In some embodiments, a first plurality of wells comprise one or more reagents for an absorbance based biochemical assay. In some embodiments a first plurality of wells comprise one or more reagents for an absorbance based biochemical assay and a different second plurality of wells comprise one or more reagents for a fluorescence based biochemical assay. In some embodiments, the fluorescence based biochemical assay is a homogeneous assay. In some embodiments, the fluorescence based biochemical assay is a heterogeneous assay. In some embodiments a first plurality of wells comprise one or more reagents for an absorbance based biochemical assay, a different second plurality of wells comprise one or more reagents for a heterogeneous fluorescence based biochemical assay and a different third plurality of wells comprise one or more reagents for a homogeneous fluorescence based biochemical assay. In some embodiments, one or more reagents are dried reagents.

In some embodiments, a first plurality of wells comprise one or more reagents for a fluorescence based biochemical assay. In some embodiments a first plurality of wells comprise one or more reagents for a fluorescence based biochemical assay and a different second plurality of wells comprise one or more reagents for an absorbance based biochemical assay. In some embodiments, the absorbance based biochemical assay is a homogeneous assay. In some embodiments, the absorbance based biochemical assay is a heterogeneous assay. In some embodiments a first plurality of wells comprise one or more reagents for a fluorescence based biochemical assay, a different second plurality of wells comprise one or more reagents for a heterogeneous absorbance based biochemical assay and a different third plurality of wells comprise one or more reagents for a homogeneous absorbance based biochemical assay. In some embodiments, one or more reagents are dried reagents.

In some embodiments, the multiwell plate comprises a length of about 100 mm or less, a depth of about 95 mm or less, and a height of about 5-10 mm or less.

In some embodiments, the multiwell plate comprises a diameter of about 100 mm or less and a height of about 5-10 cm or less.

In some embodiments, the multiwell plate has a circular shape (e.g., a disc shape) and two or more different pluralities of wells are arranged in one or more circles around the center of the circular multiwell plate. In some embodiments, the one or more circles are concentric circles. In some embodiments, the multiwell plate comprises two or more different pluralities of wells (e.g., 2 or more, 3 or more, 4 or more, 5 or more, 6 or more, 7 or more, 8 or more, 9 or more, 10 or more, 12 or more, 15 or more, 20 or more, 25 or more, 50 or more, 75 or more, or 100 or more different pluralities) arranged on two or more circles (e.g., 2 or more, 3 or more, 4 or more, 5 or more, 6 or more, 7 or more, 8 or more, 9 or more, 10 or more, 12 or more, 15 or more, 20 or more, 25 or more, 50 or more, 75 or more, or 100 or more circles, such as concentric circles). In some embodiments, the multiwell plate comprises at least one circle of wells (e.g., 1 or more, 2 or more, 3 or more, 4 or more, 5 or more, 6 or more, 7 or more, 8 or more, 9 or more, 10 or more, 12 or more, 15 or more, 20 or more, 25 or more, 50 or more, 75 or more, or 100 or more circles, such as concentric circles) comprising two or more different pluralities of wells. In some embodiments, each circle of wells on the multiwell plate consists essentially of one of the two or more different pluralities of wells on the multiwell plate. In some embodiments, each of the one or more circles of wells on the multiwell plate comprises the same number of wells (e.g., between 10 and 500 wells). In some embodiments, two or more circles of wells on the multiwell plate comprise different numbers of wells. In some embodiments, all wells of the multiwell plate have a cylindrical geometry. In some embodiments, one or more of the different pluralities of wells have a cylindrical geometry. In some embodiments, one or more of the different pluralities of wells have a cubic or rectangular cuboid geometry. In some embodiments, all of the different pluralities of wells have a cubic or rectangular cuboid geometry.

Figure 1:
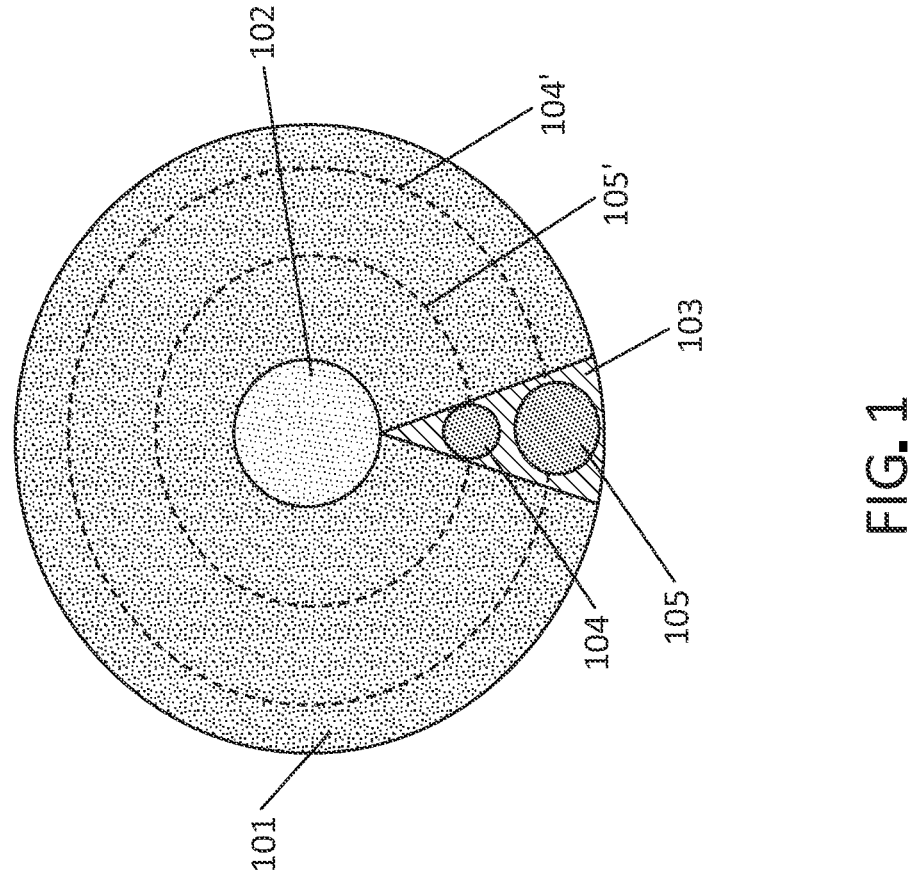
FIG. 1 shows a schematic illustrating an exemplary multiwell plate provided herein.

FIG. 1 illustrates exemplary multiwell plate 101. The circular multiwell plate 101 comprises a cylindrical central well 102 (e.g., for storing an assay buffer or a diluent). Two representative cylindrical wells 104 and 105 are shown in a 15 degree section 103 of the multiwell plate 101. Wells 104 and 105 differ at least with respect to their diameters. Wells 104 and 105 are representative wells of two different pluralities of wells that are arranged in concentric circles 104' and 105', which are centered around the central well of the multiwell plate. Only representative wells 104 and 105 are shown in FIG. 1 and the remaining wells of each of the two different pluralities of wells are indicated by concentric circles 104' and 105'. The plurality of wells represented by well 105 are positioned on the peripheral circle of wells (105') on multiwell plate 101 (i.e., on the outermost circle of wells). The plurality of wells represented by well 104 are positioned on an inner circle 104' of wells on multiwell plate 101 (i.e., a circle of wells positioned between the peripheral circle of wells 105' and the central well 102). Each of the two pluralities of wells represented by wells 104 and 105 on multiwell plate 101 comprises 24 wells (i.e., one well per 15 degree section of the circular plate). The diameter of representative well 105 is greater than the diameter of representative well 104. In some embodiments, the diameter of well 105 is 15 mm. In some embodiments, the plurality of wells represented by well 105 on the peripheral circle of wells is configured for an absorbance based assay (e.g., a biochemical or cell-based assay, a homogeneous or heterogeneous assay). In some embodiments, the plurality of wells represented by well 105 comprise a well bottom that is clear or translucent (i.e., a well bottom allowing for transmission of light of a wavelength in the ultraviolet or visible spectrum, e.g., 300-850 nm). In some embodiments, the plurality of wells represented by well 104 is configured for a fluorescence-based assay (e.g., a biochemical or cell-based assay, a homogeneous or heterogeneous assay). In some embodiments, the plurality of wells represented by well 104 comprises one or more dried assay reagents for a fluorescence based assay (e.g., fluorescent enzyme substrate or fluorescently-labeled binding protein, such as a fluorescently-labeled antibody). In some embodiments, the multiwell plate 101 can comprise one or more additional pluralities of wells that are not shown in FIG. 1 and that are different from the pluralities of wells represented by wells 104 or 105.

In some embodiments, a plurality of wells arranged on an inner circle on a circular multiwell plate comprise a smaller diameter or a smaller volume than a different plurality of wells arranged an outer circle on the multiwell plate (e.g., on the peripheral circle). In some embodiments, a plurality of wells arranged on an inner circle of wells on the multiwell plate comprise the same diameter or the same volume as a different plurality of wells arranged on an outer circle of wells on the multiwell plate. In some embodiments, a plurality of wells arranged on an inner circle of wells on the multiwell plate comprise a larger diameter or a larger volume compared to a different plurality of wells arranged on an outer circle of wells on the multiwell plate.

In some embodiments, a an inner circle of wells on a circular multiwell plate comprises fewer wells than an outer circle of wells on the multiwell plate (e.g., the peripheral circle). In some embodiments, an inner circle of wells on a circular multiwell plate comprises the same number of wells as an outer circle of wells on the multiwell plate. In some embodiments, an inner circle of wells on a circular multiwell plate comprises a smaller number of wells than an outer circle of wells on the multiwell plate.

In some embodiments a circular multiwell plate comprises a central well (e.g., comprising an assay buffer or diluent). The central well can have a cylindrical, cubic or other geometry. The size of the central well can be the same as or different from the size of any other well on the multiwell plate. In some embodiments, the central well comprises as larger diameter or volume than any other well on the multiwell plate. In some embodiments, the central well comprises one or more subdivisions, e.g., as reservoirs for two or more assay buffers, assay reagents, diluents, or the like (e.g., sample dilution buffer, substrate solution, stop solution).

In some embodiments, the diameter of wells on the peripheral circle of wells on a circular multiwell plate is 1.5 mm. In some embodiments, the peripheral circle of wells on a multiwell plate comprises 24 wells. In some embodiments, the wells on the peripheral circle of wells are configured for an absorbance assay (e.g., wells comprise a well bottom that is clear or allows for transmission of light of a visible or ultraviolet wavelength, e.g., 280 nm, 540 nm). In some embodiments, the multiwell plate further comprises a central well comprising a greater diameter or volume than the largest well of any one of the pluralities of wells on the multiwell plate. See, e.g., FIG. 1. In some embodiments, the bottoms of some or all wells of the multiwell plate are of a clear material (e.g., allowing transmission of light in 300-700 nm range). In some embodiments, the walls of some or all wells of the multiwell plate comprise a spectral absorbent plastic (e.g., a material that is opaque, solid black, or otherwise does not allows for transmission of light of a wavelength in the visible or ultraviolet range, e.g., 280 nm, 540 nm, 200 nm-850 nm). In some embodiments, the inner well surfaces of the bottoms of some or all wells of the multiwell plate comprise a hydrophilic, low protein binding, or non-cytotoxic coating. In some embodiments, the multiwell plate further comprises one or more different pluralities of wells configured for a fluorescence based assay (e.g., a cell-based fluorescence assay or a fluorescent based biochemical assay). In some embodiments, the multiwell plate further comprises one or more different pluralities of wells configured for a heterogeneous assay (e.g., a bead-based assay or an assay involving an inner well wall surface).

In some embodiments, a multiwell plate provided herein comprises a "clear" or "translucent" bottom in one or more wells. As used herein, the terms "clear" or "translucent" are used to describe a material that at least partially transmits light of a wavelength of interest in a ultraviolet or visible range, e.g., between 220 nm and 850 nm, between 300 nm-850 nm, between 400 nm-800 nm, or between 300 nm-700 nm. By contrast, a material referred to herein as "opaque" or "solid" (e.g., solid black or solid white) is a material that transmits essentially no light of a wavelength of interest in the ultraviolet or visible range. In some embodiments, a clear or translucent well or multiwell plate bottom transmits at least 1%, at least 3%, at least 5%, at least 10%, at least 20%, at least 30%, at least 40%, at least 50%, at least 60%, at least 70%, at least 80%, or at least 90% of light hitting the surface of the bottom in a device or system provided herein. In some embodiments, at least 1%, at least 3%, at least 5%, at least 10%, at least 15%, at least 20%, at least 25%, at least 30%, at least 40%, at least 50%, at least 60%, at least 70%, at least 80%, at least 90%, at least 95%, or 100% of wells of the multiwell plate comprise a clear or translucent bottom. In some embodiments, some or all of the wells on the peripheral circle of wells on a circular multiwell plate comprise a clear, or translucent bottom. In some embodiments, only wells on the peripheral circle of wells on a circular multiwell plate comprise a clear or translucent bottom.

Figure 2:
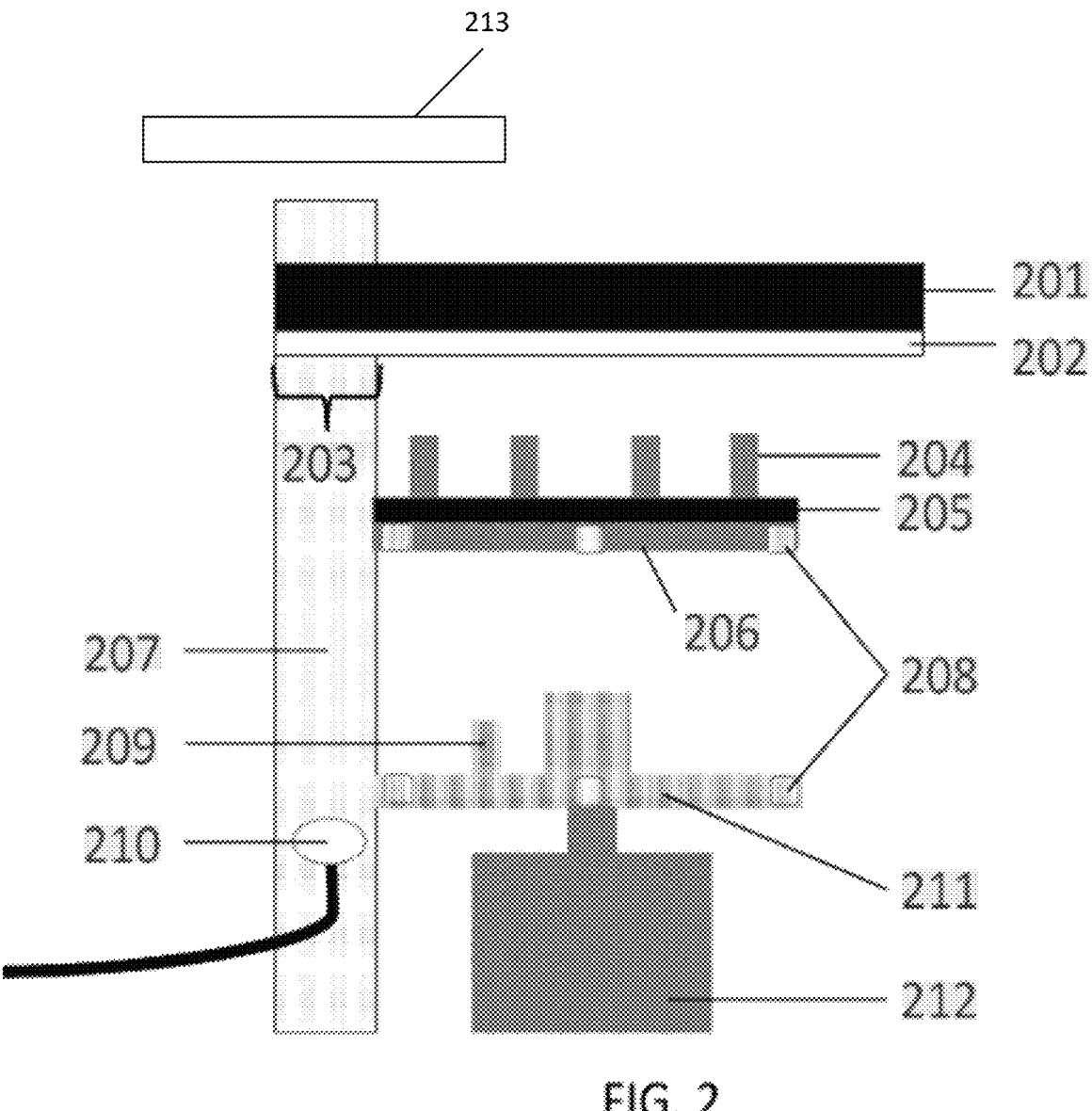
FIG. 2 shows a schematic illustrating an exemplary device ("Assay Measurement Unit" or assay station) provided herein.

In some embodiments, the entire bottom of the multiwell plate is made of a clear or translucent bottom. See, e.g., FIG. 2 (multiwell plate bottom 202). In some embodiments, the multiwell plate comprises a translucent material forming some or all of the well bottoms of the multiwell plate (e.g., FIG. 2, multiwell plate bottom 202) and further comprises well walls in some or all of the wells comprising an opaque material (e.g., black plastic; FIG. 2, multiwell plate walls 201). In some embodiments, the clear or translucent multiwell bottom and the opaque multiwell walls are welded together using ultrasonic welding. In some embodiments, the multiwell plate further comprises a coating on an inner surface of one or more wells that is hydrophilic (e.g., not cytotoxic or high-protein binding).

In some embodiments, a clear or translucent bottom of a multiwell plate can be covered, at least in parts, by an opaque material. In some embodiments, the opaque material is an opaque plastic film, metal foil (e.g., aluminum), or the like. In some embodiments, the clear or translucent bottom of the multiwell plate is covered, at least in parts, by placing the multiwell plate onto a plate holder. See, e.g., FIG. 2, plate holder 206.

In some embodiments, the multiwell plates provided herein can be packaged in a packaging material, e.g., in a pouch or in another container, such as a cardboard box. In some embodiments, the packaging is sterile. In some embodiments, the packaging is non-sterile. In some embodiments, a multiwell plate is packaged individually (e.g., in a sterile, sealed pouch). In some embodiments, two or more multiwell plates can be packaged together in the same package (e.g., 2, 3, 4, 5, 6, 7, 8, 9, 10, 12, 15, 20, 25, 50, 75, 100, or more multiwell plates per package). In some embodiments, two or more individually packaged multiwell plates (e.g., individually packaged in sterile pouch) can further be packaged together (e.g., in a cardboard box or a cartridge, e.g., sterile or non-sterile).

In some embodiments, the arrangement of two or more different pluralities of wells on a multiwell plate is fixed; individual wells or one or more of the different pluralities of wells cannot be separated or removed from the multiwell plate.

In some embodiments, one or more individual wells on a multiwell plate are removable. In some embodiments, a centrally located reagent well is removable from the multiwell plate. In some embodiments, one or more of the different pluralities of wells are removable from the multiwell plate.

In some embodiments, a multiwell plate can comprise a combination of two or more different pluralities of wells, wherein one or more of the different pluralities of wells are individually removable. In some embodiments, the one or more individually removable pluralities of wells comprise 2 or more, 3 or more, 4 or more, 5 or more, 6 or more, 7 or more, 8 or more, 9 or more, or 10 or more different pluralities of wells. In some embodiments, the one or more individually removable pluralities of wells are selected from 2 or more, 3 or more, 4 or more, 5 or more, 6 or more, 7 or more, 8 or more, 9 or more, 10 or more, 12 or more, 14 or more, 16 or more, 18 or more, 20 or more, 25 or more, 30 or more 35 or more, 40 or more, 45 or more, 50 or more, 60 or more, 70 or more, 80 or more, 90 or more, or 100 or more different pluralities of wells.

In some embodiments, the multiwell plates provided herein can comprise some or all reagents required in an assay (e.g., as dried assay reagents or in solution). Such multiwell plates with predispensed reagents can facilitate mix-and-read assay protocols that just require addition of a sample to a well to start an assay reaction.

In some embodiments, one or more of the different pluralities of wells comprise one or more assay reagents. In some embodiments, the one or more assay reagents are in solution. In some embodiments, the one or more assay reagents are provided in a dried form. In some embodiments, the dried assay reagent is coated onto a well surface. In some embodiments, the dried assay reagent comprises an enzyme, an enzyme substrate (e.g., a fluorescence substrate), a binding protein (e.g., an antibody, RNA aptamer, oligonucleotide capture probe), a carrier protein (e.g., bovine serum albumin (BSA)), a detection reagent, a detergent, a salt, a sugar, a cell (e.g., a mammalian cell or a bacterial cell), or the like.

In some embodiments, all assay reagents required to perform an assay are provided in a dried form in one or more of the different pluralities of wells. In some embodiments, only a sample volume, and, optionally, a buffer solution (e.g., suspension buffer or reaction buffer) need to be added to start an assay reaction to analyze an analyte of interest.

In some embodiments, the shelf-life of the reagents dried onto the surfaces of one or more of the different pluralities of wells is 1 week or more, 2 weeks or more, 3 weeks or more, 4 weeks or more, 6 weeks or more, 2 months or more 3 months or more, 4 months or more, 6 months or more 9 months or more, 12 months or more, 18 months or more, 24 months or more, 30 months or more 36 months or more, 42 months or more 48 months or more 54 months or more, or 60 months or more, at room temperature (e.g., about 24° C.), at about 30° C., at about 34° C., at about 38° C., at about 42° C., at about 45° C., or at about 50° C.

In some embodiments, the shelf life of the reagents dried onto the surfaces of one or more of the different pluralities of wells is determined by the performance of an assay performed in a well comprising the dried reagents. In some embodiments, the shelf life of dried reagents in a well is considered to be maintained, if the performance of an assay drops by 50% or less, 40% or less, 35% or less, 30% or less, 25% or less, 20% or less, 15% or less, 10% or less, 5% or less, 3% or less, 2% or less, or 1% or less within a given time period (e.g., within 1 week, 1 month, 3 months, 6 months, 1 year, 2 years, and the like). In some embodiments, the assay performance is determined, e.g., by the detection limit for an analyte of interest, the absolute signal obtained in a positive control reaction (e.g., a reaction with a known quantity of analyte present), the S/N ratio of a control reaction, the signal background level (e.g., signal in a negative control sample), or another measure of assay performance.

In some embodiments, the multiwell plates provided herein comprise a marker describing the design of the multiwell plate (e.g., the arrangement and properties of two or more pluralities of wells on the multiwell plate, including, e.g., the reagent content). In some embodiments, the marker describes the panel of analytes panel that can be tested using the multiwell plate. In some embodiments, the barcode encodes additional information, e.g., related to the multiwell plate (e.g., expiration date of assay reagents, batch number, or the like) or related to the consumer (e.g., identifying information). In some embodiments, the marker is a barcode (e.g., a one-dimensional or two-dimensional barcode), a Quick Response Code (QR code), a radio-frequency identification (RFID) tag, or the like. In some embodiments, the marker is located on the top of the multiwell plate (e.g., in a peripheral region or in between two wells). In some embodiments, the marker is located on a side of the multiwell plate. In some embodiments, the marker is located on the bottom of the multiwell plate (e.g., in an overhang region).

In some embodiments, the multiwell plates provided herein consist of a single component.

In some embodiments, the multiwell plates consist of a single circular component comprising 120 wells arranged in a spokes-like arrangement radiating out from the center of the multiwell plate to the periphery. In some embodiments, the 120 wells are arranged in groups of four wells per "spoke." In some embodiments, the 120 wells are arranged in groups of three pluralities of wells (e.g., 40 wells per group, 10"spokes per group). In some embodiments, the 120 wells share a cylindrical shape and share the same dimensions. In some embodiments, the multiwell plate has an outer diameter of 115 mm and a height of 6 mm. In some embodiments, the multiwell plate comprises two or more troughs arranged in a circle around the center of the multiwell plate. In some embodiments, the two or more troughs differ with respect to their dimensions. See, e.g., FIG. 5A.

Figure 5B:
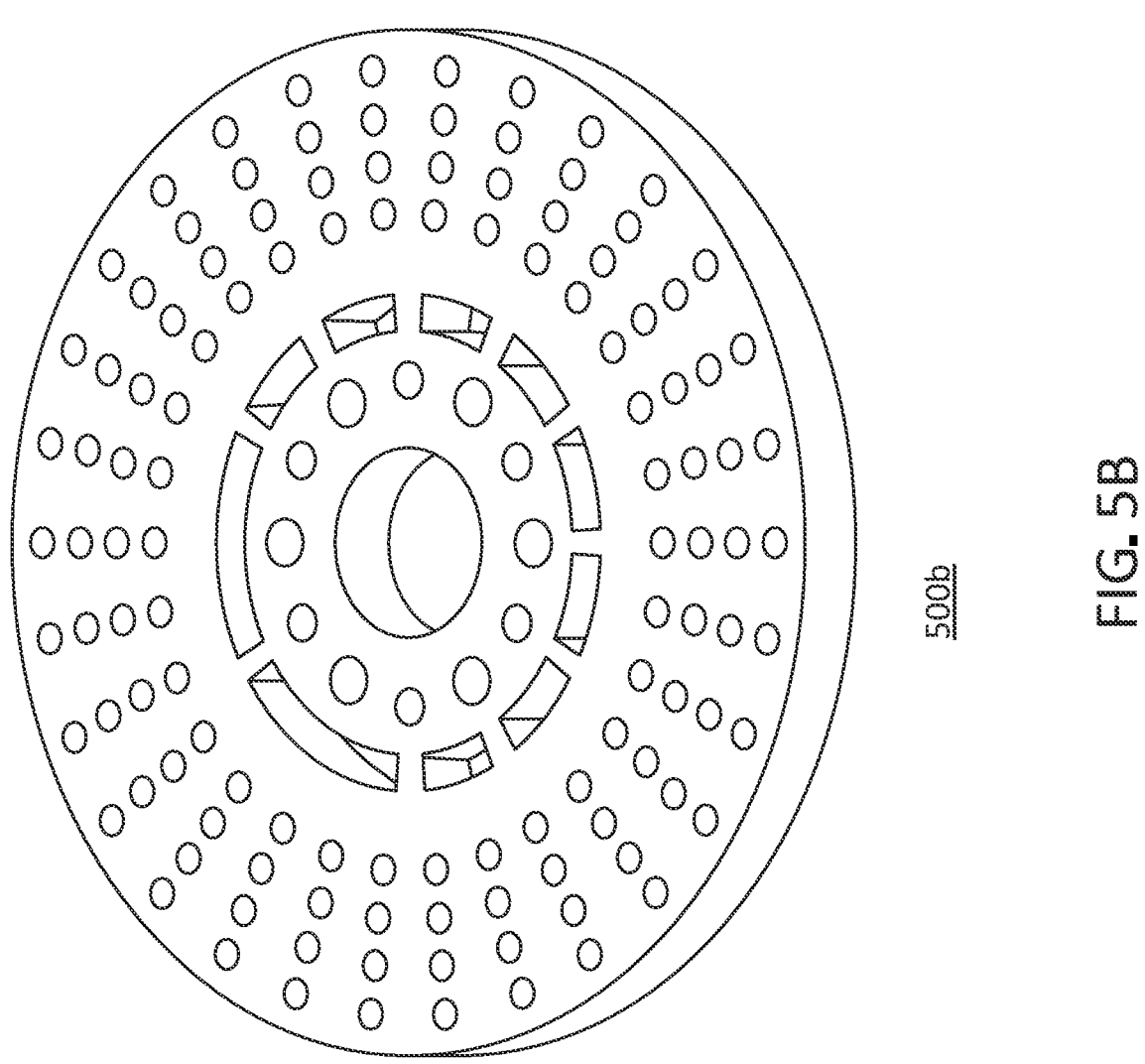

In some embodiments, the multiwell plates consist of a single circular component comprising 120 wells arranged in a spokes-like arrangement radiating out from the center of the multiwell plate to the periphery. In some embodiments, the 120 wells are arranged in groups of four wells per "spoke." In some embodiments, 30 "spokes" of 4 wells each are equidistantly distributed around the circular multiwell. In some embodiments, the 120 wells share a cylindrical shape and share the same dimensions. In some embodiments, the multiwell plate has an outer diameter of 115 mm and a height of 6 mm. In some embodiments, the multiwell plate comprises two or more troughs arranged in each of two or more circles around the center of the multiwell plate. In some embodiments, the shapes of the troughs differ in the different circles of troughs. In some embodiments, the dimensions of the troughs differ within the one or more circles of troughs. See, e.g., FIG. 5B.

In some embodiments, the multiwell plates provided herein comprise two or more components. In some embodiments, the multiwell plates provided herein comprise a carrier component that is configured to hold one or more "chip" components, and one or more chip components. In some embodiments, the chip components are be removably attached to a carrier.

In some embodiments, the multiwell plates comprise 2, 3, 4, 5, 6, 7, 8, 9, 10, or more chip components. In some embodiments the multiwell plates comprise between 10 and 100, between 20 and 100, between 30 and 100, between 40 an 100, between 50 and 100, between 60 and 100, between 70 and 100, between 80 and 100, or between 90 and 100 chip components.

In some component, each chip component can comprise one or more of the two or more two or more different pluralities of wells on the multiwell plate. In some embodiments, each chip on a carrier has the same one or more pluralities of wells. In some embodiments, two or more chips held on the same carrier are different pluralities of wells. The wells in the pluralities of wells on a chip component can have any property or combination of properties of a plurality of wells described herein.

As used herein, the term "chip" refers to a component of a multiwell plate provided herein that comprises one or more pluralities of wells of the two or more different pluralities of wells on the multiwell plate.

In some embodiments, the pluralities of wells on a chip component can comprises a total of 10 or more, 20 or more, 30 or more, 40 or more, 50 or more, 60 or more, 70 or more, 80 or more, 90 or more, 100 or more, 120 or more, 140 or more, 160 or more, 180 or more, 200 or more, 250 or more, 300 or more, 350 or more, 400 or more, 450 or more, 500 or more, 600 or more, 700 or more, 800 or more, 900 or more, 1,000 or more, 2,000 or more, 3,000 or more, 4,000 or more, 5,000 or more, 6,000 or more, 7,000 or more, 8,000 or more, 9,000 or more, or 10,000 or more wells.

In some embodiments, the carrier component comprises one or more plurality of the two or more different pluralities of wells on the multiwell plate.

In some embodiments, the carrier component does not comprise a plurality of the two or more different pluralities of wells on the multiwell plate.

The carrier component can include one or more well-like structures, or one or more pluralities of well-like structures, other than assay wells, such as moats or troughs. Such well-like structures can be useful, e.g., to store bulk reagents, such as assay buffers or stop reagents, or to process assay reagents or samples prior to addition to an assay well.

FIG. 6A illustrates an exemplary multiwell plate (also referred to as a "cartridge") comprising a carrier (619A) and six chips (618A). Each of the chips 618A comprises 20 wells that share a cylindrical shape and identical dimensions. The approximate dimensions of each chip are 32 mm×25 mm×8 mm. The multiwell plate has an outer diameter of 95 mm and is 11 mm tall. The carrier holds the chips with a magnet and pin connection.

FIG. 6B illustrates an exemplary multiwell plate comprising a carrier (619B) and three chips (618B). Each chip comprises 48 well. The 48 wells share a cylindrical shape and have different diameters. The approximate dimensions of each chip are 70 mm×30 mm×6 mm. The multiwell plate has an outer dimension of 115 mm and is 9 mm tall. The carrier holds the chips with a magnet and pin connection.

FIG. 6C illustrates an exemplary multiwell plate comprising a carrier (619C) and three chips (618B). The carrier 619C comprises 9 troughs that are useful, e.g., for mixing reagents or reconstituting bulk standards. Each chip comprises 48 well. The 48 wells share a cylindrical shape and have different diameters. The approximate dimensions of each chip are 70 mm×30 mm×6 mm. The multiwell plate has an outer dimension of 115 mm and is 9 mm tall. The carrier holds the chips with a magnet and pin connection.

FIG. 6D, FIG. 6E, FIG. 6F, and FIG. 6G illustrate exemplary carrier designs.

FIG. 7, FIG. 8, and FIG. 9 illustrate exemplary multiwell plates comprising a carrier holding 3 (FIG. 7), 5 (FIG. 8), or 6 (FIG. 9) chips. Different chips on a carrier can comprise pluralities of wells having the same dimensions within each chip and on different chips on the carrier (e.g., FIG. 7 and FIG. 8). The carrier shown in FIG. 7 comprises several pluralities of troughs and wells other than assay wells. FIG. 9 illustrates an embodiment in which a carrier holds different types of chips comprising different pluralities of wells. The carrier of FIG. 9 comprises four of the same type of chip, each comprising 16 wells sharing a cylindrical shape and identical dimensions. A fifth chip comprises at least two different pluralities of wells that share a cylindrical shape and differ in their diameters. A sixth chip does not include assay wells. The sixth chip of the multiwell plate of FIG. 9 comprises at least two different pluralities of troughs that differ in their dimensions.

FIG. 10, FIG. 11A, FIG. 11B, FIG. 12A and FIG. 12B illustrate additional embodiments of multiwell plates comprising a carrier configured to hold one or more chips.

FIG. 13A, FIG. 13B, FIG. 13C, FIG. 13D, FIG. 13E, FIG. 13F, FIG. 13G, FIG. 13H, FIG. 13I, FIG. 13J, FIG. 13K, FIG. 13L, FIG. 13M, FIG. 13N and FIG. 13O illustrate exemplary embodiments of chips that can be arranged in any combination on a carrier to generate a multiwell plate provided herein.

5.2 Kits

In another aspect, provided herein is a kit, comprising one or more multiwell plates provided herein, and, optionally, assay reagents for two or more different assays.

In some embodiments, the kit comprises one or more subcomponents of a multiwell plate, such as a carrier component or a chip component comprising a plurality of wells.

In some embodiments, a multiwell plate provided herein is packaged together with one or more assay buffers (e.g., enzyme or substrate dilution buffer, stop solution, cell culture media, or the like) or diluents (e.g., water, phosphate buffer, dimethylsulfoxide (DMSO), ethanol, isobutanol, or the like). In some embodiments, the volume of an assay buffer or diluent packaged together with the multiwell plate is between 10 µl and 10 ml, such as between 10 µl and 100 µl, between 100 µl and 500 µl, between 500 µl and 1 ml, between 1 ml and 2 ml, between 2 ml and 3 ml, between 3 ml and 4 ml, between 4 ml and 5 ml, between 5 ml and 6 ml, between 6 ml and 7 ml, between 7 ml and 8 ml, between 8 ml and 9 ml, or between 9 ml and 10 ml. In some embodiments, the one or more assay buffer or diluents comprise all liquid solutions needed in order to perform all assays (e.g., biochemical or cell-based assays) the multiwell plate is configured for. In some embodiments, the one or more assay buffers or diluents are packaged separately from the multiwell plate, e.g., in a separate vial, pod or other container. In some embodiments, the vial, pod or container comprises a sealed opening (e.g., an opening sealed with a membrane or foil) that can be pierced by a piercing device (e.g., a needle or blade) connected to a system provided herein. In some embodiments, the one or more assay buffers are packaged in one or more wells of the multiwell plate, e.g., in a reagent well located in the center of a circular multiwell plate. In some embodiments, a well comprising an assay buffer is covered by a lid, membrane or foil that seals the assay buffer within the well.

In some embodiments, a package comprising two or more multiwell plates comprises the same type of multiwell plate (e.g., same configuration of wells, same assay reagent content). For example, all multiwell plates in a package are configured to assay analytes of the same analyte panel, e.g., a pre-diabetes panel. Such packaging of identical plates can, e.g., be useful in a DTC diagnostics application where multiple consumers are testing their blood for the same panel of analytes (e.g., within a day). Stacks of identical plates can for example be housed in a cartridge connected to an integrated system provided herein. In some embodiments of the methods provided herein, a system operator can, e.g., transfer a package comprising identical multiwell plates from an off-system storage location (e.g., a warehouse) onto a system provided herein in preparation for daily operations of the system.

In some embodiments, the two or more multiwell plates that are packaged together comprise two or more different multiwell plates (e.g., different configuration of wells, different assay reagent content). In some embodiments, all of the multiwell plates in a package are different from each other. For example, each multiwell plate in a package can be configured to assay a different analyte panel, e.g., a pre-diabetes panel, a cholesterol lipid panel, a fertility panel, and a thyroid panel. Such packaging of different plates can, e.g., be useful in a DTC diagnostics application where a single consumer chooses to conduct a comprehensive analysis of a blood sample for multiple panels of analytes. For example, in connection with some methods provided herein, a consumer can choose, e.g., by interfacing with a terminal (e.g., a desktop computer, tablet, or mobile devise), to have a sample analyzed for one or more analyte panels. In some embodiments of the methods provided herein, a system operator can transfer a package comprising a specific combination of multiwell plates from an off-system storage location onto a system provided herein in preparation for testing a specific combination of analyte panels in response to a consumer's specific selection.

5.3 Assay Station

In another aspect, provided herein is an assay station configured to handle the multiwell plates described herein and configured to perform the methods described herein.

The disclosure provided herein is based, in part, on the realization that certain designs relating to the placement or installation of a multiwell plate provided herein are useful to facilitate the synchronized performance of multiple assays using different assay formats and readouts, e.g., in the same multiwell plate. For example, the device designs provided herein can facilitate the parallel performance of absorbance based assays, which require translucent well bottoms, and fluorescence-based assays, which generally benefit from having opaque assay well bottoms, in multiwell plates having the same clear or translucent bottoms in every well. See, e.g., FIG. 2, multiwell plate bottom 202. In other words, the device designs provided herein render it unnecessary to construct relatively complex multiwell plates combining different well bottom materials in different parts of a multiwell plate (e.g., translucent materials for bottoms of peripheral wells and opaque materials for the bottoms of more centrally positioned wells on a multiwell plate). Thus, certain device designs provided herein allow for the simplification of multiwell plate designs and can reduce the complexities and costs of multiwell plate production.

In some embodiments, the assay station comprises a plate holder configured to hold a multiwell plate described herein. In some embodiments, the plate holder comprises one or more magnets, vertical keys, key holes, or the like, that can engage with one or more complementary magnets, keyholes, vertical keys, or the like in a multiwell plate provided herein to align or move the multiwell plate relative to other components of the assay station (e.g., a light source or a detector). See, e.g., FIG. 2 (plate holder 206 comprising vertical keys 204 and magnets 208).

In some embodiments, the assay station comprises a motor, coupled to a seat or a platform.

In some, the plate holder comprises one or more vertical keys, key holes or magnets, which are configured to engage with corresponding key holes, vertical keys or magnets on a platform or seat in an assay station provided herein. In some embodiments, the platform is a seat coupled to a motor, e.g., in an assay station provided herein.

In some embodiments, the assay station comprises a multiwell plate-plate holder assembly provided herein.

In another aspect, provided herein is an assembly comprising a multiwell plate provided herein and a plate holder provided herein. In some embodiments, the multiwell plate in the assembly comprises a clear or translucent material forming the bottom of some or all of the wells of the multiwell plate. In some embodiments of the assembly, the multiwell plate is placed on top of the plate holder such that the plate holder covers some or all of the bottom of the multiwell plate (e.g., a bottom comprising clear or translucent material). In some embodiments, the plate holder covers at least 5%, at least 10%, at least 15%, at least 25%, at least 30%, at least 40%, at least 50%, at least 60%, at least 70%, at least 80%, at least 90%, or 100% of the multiwell plate bottom (e.g., as determined by surface area of the multiwell bottom, or by relative number of wells covered). In some embodiments, at least the peripheral circle of wells on a circular multiwell plate provided herein is not covered by the plate holder and forms an overhang. See, e.g., FIG. 2 (overhang 203). In some embodiments, the plate holder is made of a opaque material (e.g., an opaque metal or plastic). In some embodiments, the plate holder comprises an opaque film (e.g. a Lexan® spectral absorbent opaque film, or other solid opaque material) that covers, at least in parts, a surface of the plate holder such that the opaque film is positioned at the interface of the multiwell plate and the plate holder in the multiwell plate-plate holder assembly. In some embodiments of the assembly, the plate holder comprises one or more magnets. In some embodiments, the plate holder comprises one or more vertical keys. In some embodiments, the plate holder comprises one or more key holes. In some embodiments, the plate holder comprises one or more vertical keys or magnets and the multiwell plate comprises one or more complementary key holes or magnets, that are configured to engage each other in the multiwell plate-plate holder assembly to align the multiwell plate with the plate holder. In some embodiments of the assembly, the plate holder comprises one or more vertical keys, key holes or magnets, which are configured to engage with corresponding key holes, vertical keys or magnets on a platform or seat in an assay station provided herein. In some embodiments, the platform or seat is coupled to a motor, e.g., in a device or system provided herein.

FIG. 2 illustrates an exemplary multiwell plate-plate holder assembly and aspects of an assay station provided herein. A circular (e.g., disc shaped) multiwell plate provided herein comprises opaque well walls 201 and a clear or translucent multiwell bottom 202 that are welded together, e.g., by laser welding or ultrasonic welding. A plate holder 206 comprises magnets 208, vertical keys 204 and an opaque film 205. The vertical keys in the plate holder are configured to engage corresponding key holes in the multiwell plate (not shown) to align the multiwell plate and the plate holder in the multiwell plate-plate holder assembly. In the assembly, the plate holder does not cover the entire bottom 202 of the multiwell plate, which forms an overhang 203. A light source 210 for visible or ultraviolet light is positioned in the exemplary assay station of FIG. 2 such that light path 207 hits the overhang 203 portion of multiwell bottom 202 and light can pass through one or more wells on the peripheral circle of wells or adjacent inner circles of wells of the multiwell plate to be read out by a detector in the device (213). The plate holder is configured to engage with a vertical key 209 and magnets 208 in a seat 211 that is coupled to a motor 212 in the device. The motor can rotate the seat and engage the multiwell plate-plate holder assembly to move the overhang portion of the multiwell plate, and the wells therein, relative to the light source 210 and the light path 207. The dimensions of the seat 211, the plate holder 206, and their positions in the device relative to light source 210 are chosen to avoid interference with the light path 210.

In some embodiments, the assay station comprises an assembly of a circular multiwell plate and a plate holder provided herein, a seat or platform engaging the plate holder and coupled to a motor, and a light source. The multiwell plate-plate holder assembly can be placed on the seat, and the assembly and seat can be aligned through engagement of juxtaposed magnets, vertical keys and key holes in the plate holder and in the seat. In the multiwell plate-plate holder assembly, the plate holder does not cover the bottoms of one or more outer circles of wells in the multiwell plate (e.g., the peripheral circle and one or more adjacent inner circles), which creates an overhang. In the assay station, the light source is configured such that light from the light source can reach the parts of the multiwell bottom not covered by the plate holder (e.g., the bottom of a well in the peripheral circle of wells on a circular multiwell plate) and transmit light through a well on the peripheral or outer circles of the multiwell plate. In some embodiments, the light source is a source of ultraviolet or visible light.

In some embodiments, the assay station comprises a detector on the opposite side of the multiwell plate from the light source. The detector can read out light transmitted through a well of the multiwell plate. The motor coupled to the seat is configured to allow for rotation of the seat and of the multiwell plate-plate holder assembly. Driven by the motor, the assembly can rotate relative to the light source, such that light from the light source can reach the bottom of different wells in the circle of wells of the multiwell plate not covered by the plate holder.

In some embodiments, the assay station comprises a barcode reader configured to read a barcode on a multiwell plate (e.g., on top of the plate, on the side of a plate, or on the bottom of a plate, e.g., in the overhang region).

In some embodiments, the assay station comprises a detector capable of absorbance and fluorescence measurements. In some embodiments, the detector is capable of simultaneous bulk and event fluorescence measurements. Exemplary detection devices capable of simultaneous bulk and event fluorescence are described, e.g., in WO 2012/059786 A1.

In some embodiments, the assay station comprises a liquid handling device (e.g., a piezoelectric or acoustic liquid dispenser) capable of transferring a small volume (e.g., 1 nl-1 μl) of aqueous liquid from a reagent reservoir to into a well of the multiwell plate. In some embodiments, the reagent reservoir is located on the multiwell plate (e.g., a central well on a circular plate). In some embodiments, the assay station comprises one or more separate reagent reservoirs not located on a multiwell plate.

In some embodiments, the assay station comprises an assembly as illustrated in FIG. 2.

In some embodiments, the assay station comprises a liquid handling device configured to directly transfer small aliquots (e.g., 1 nl-1 μl) of an essentially undiluted consumer sample (e.g., blood sample) from a sample container to a multiwell plate provided herein.

In some embodiments, the assay station comprises a piercing device (e.g., needle, blade, or the like), to pierce a cover (e.g., plastic membrane or metal foil) on a multiwell plate (e.g., a cover on a central well) or on a separate reagent or sample container.

In some embodiments, the dimensions of the assay station are less than 1 m (width)×1 m (length)×1 m (height). In some embodiments, the dimensions of the apparatus are about 700 mm×600 mm×800 mm.

In some embodiments, the assay station comprises an assay measurement unit (AMU). In some embodiments, the AMU is a unit as illustrated in FIG. 14. The AMU of FIG. 14 is configured to hold a multiwell plate ("cartridge") 158. An R stage motor 1511 can be used to move an R stage in and out of the AMU to move the cartridge 158 to different read positions within the AMU or to move the cartridge 158 out to a loading position. The AMU comprises an absorbance optics module 156 and a fluorescence optics module 1510. A theta motor 159 can rotate a sample to allow for measurements at different positions on cartridge 158. The theta motor 159 can mix a sample in cartridge 158 by oscillating quickly. A heater unit 7 can be used to radiate heat onto cartridge 158. In some embodiments, the heater unit comprises a plate and a resistive heater unit laminated on top.

In some embodiments, the assay station comprises a system as illustrated in FIG. 15. The system comprises and AMU 1612, a consumables mount 165, a computer (e.g., Linux based) 1613, a spectrometer 1614, a light source 1615, a 3 axis robot (e.g., a Cavoro Omni Robot by Tecan, San Jose, CA) 1616 and an automatic pipette for the 3 axis robot (e.g., an air displacement pipette) 1617.

In some embodiments, the consumables mount 165 is a consumables mount as illustrated in the drawings of FIG. 16A and FIG. 16B. Such as consumables mount can comprise a tube holder 171, a pipette tip rack holder 172, a diluents tray holder 173, and a waste bag holder 174. The tube holder 171 can comprise an area to hold a single tube of a patient's sample (e.g., plasma or whole blood sample). The pipette tip rack holder 172 can comprise an area to hold a rack of pipette tips. The diluents tray holder 173 can comprise an area to hold, e.g., a traditional deepwell 96-well plate that can be filled, e.g., with a diluent and can be sealable. The waste bag holder 174 can comprise an area for holding a biohazard wastebag. In some embodiments, the consumables mount is attached to a baseplate of an assay station.

5.4 Sample Processing Station

In another aspect, provided herein is a sample processing station. In some embodiments, the sample processing station comprises a sample collection station, e.g., a station for collecting a consumer's blood sample, saliva, urine or other bodily fluid. In some embodiments, the sample processing station comprises a quality control station configured to perform a quality control test on the sample, e.g., to test for possible sample contamination or to confirm that the sample is a representative sample of a customer. In some embodiments, the sample processing station comprises a sample dilution station.

In some embodiments, the sample collection station comprises a sample collection device, such as a device for the collection of a blood sample (e.g., a TAP Touch Activated Phlebotomy™ device by Seventh Sense Biosystems or a HemoLink™ device by Tasso, Inc.). In some embodiments, the sample collection device is removable from the sample collection station. In some embodiments, the sample collection device comprises as sample container. In some embodiments, the sample collection device is disposable. In some embodiments, the sample collection device is sterile. In some embodiments, the sample collection device is configured to collect venous blood that is essentially free from contamination with interstitial fluid (e.g., <5% interstitial fluid is present in the venous blood). In some embodiments, the sample processing station comprises as device capable of measuring the sample volume (e.g., the sample volume in the sample container). In some embodiments, the sample processing station comprises an analytical device capable of measuring the level of contamination of a blood sample with extracellular fluid (e.g., a mass spectrometer, a gas chromatogram, an HPLC, a fluorescence or absorbance reader).

In some embodiments, the sample processing station comprises a sample dilution station. In some embodiments, the sample dilution station comprises a liquid handling device capable of preparing a dilution or dilution series of a small sample volume (e.g., 1-200 µl of a human blood sample). In some embodiments, the sample dilution station is comprises a sample dilution plate (e.g., a disposable traditional multiwell) and a multiwell plate provided herein. In some embodiments, the sample dilution station comprises a liquid handling device capable of transferring an aliquot of a sample or of a sample dilution from the sample dilution plate to a multiwell plate provided herein. In some embodiments, the liquid handling device is capable of preparing a sample dilution series directly in the multiwell plate provided herein.

In some embodiments, the sample processing station comprises a sample collection station, a sample dilution station, and, optionally, a quality control station (e.g., stations encased in the same housing or coupled to the same chassis).

In some embodiments, the sample processing station comprises a sample dilution station, and, optionally, a quality control station (e.g., stations encased in the same housing or coupled to the same chassis).

5.5 Multianalyte Detection Systems

The systems provided herein are useful, e.g., at a POCC site to perform robust, rapid, and low-cost analyses of multiple analytes of interest in a sample from a consumer.

In another aspect, provided herein is a multianalyte detection system comprising an optional consumer interface, an assay station (e.g., an assay station provided herein), a data processing unit and, optionally, a sample processing station. In some embodiments, the sample processing station comprises a sample dilution station and, optionally, a sample collection station. In some embodiments, the sample processing station comprises a sample quality control station. In some embodiments, the multianalyte system comprises a multiwell storage unit, e.g., to store one or more multiwell plates provided herein. In some embodiments, the multianalyte system does not comprise a consumer interface.

In some embodiments, the dimensions of the multianalyte detection system are less than 1 m (width)×1 m (length)×1 m (height). In some embodiments, the dimensions of the multianalyte detection system are less than 500 mm (width)×500 mm (length)×500 mm (height). In some embodiments, the dimensions of the multianalyte detection system are about 400 mm×400 mm×400 mm.

In some embodiments, the sample processing station is separate station from the assay station. In some embodiments, the sample processing station comprises (e.g., encased in the same housing or coupled to the same chassis) a sample collection station and a sample dilution station. In some embodiments, the multianalyte system comprises a sample collection station that is a separate station from the sample processing station.

In some embodiments, a sample processing station is coupled to an assay station by a chassis. In some embodiments, the sample processing station is coupled to the assay station by a conveyor belt. In some embodiments, the conveyor belt is configured to transfer a multiwell plate (e.g., a multiwell plate provided herein) from the sample processing station to the assay station. In some embodiments, the chassis is coupled to a robotic arm (e.g., Staubli) configured to transfer a multiwell plate from the sample processing station to the assay station.

In some embodiments, the system provided herein comprises a barcode reader (e.g., connected to the sample processing station or the assay station, or both) that is configured to read a marker (e.g., a barcode, QR code, or RFID tag) on a multiwell plate provided herein. In some embodiments, the barcode encodes the design of the multiwell plate (e.g., the arrangement and properties of two or more pluralities of different wells), or the analyte panel that can be tested using the multiwell plate. In some embodiments, the barcode encodes additional information related to the multiwell plate (e.g., expiration date, batch number, or the like) or related to sample or consumer identification (e.g., consumer identification number, sample tracking number, or the like).

In some embodiments, the system provided herein comprises a storage container for multiwell plates. In some embodiments, the storage container is a component of a sample processing station or of an assay station. In some embodiments, the storage container is a separate component that is connected, e.g., by a conveyor belt or a robotic arm, to a sample processing station or an assay station. In some embodiments, the storage container comprises a plurality of the same multiwell plates. In some embodiments, the storage container comprises two or more subdivisions, wherein each subdivision comprises a plurality of the same multiwell plates and wherein the multiwell plates in the two or more subdivisions are different from each other.

In some embodiments, the system comprises a consumer interface (e.g., a computer terminal or a touchscreen) coupled to the assay station, to the data processing station, and optionally the sample processing station. In some embodiments, the consumer interface is connected to the internet and the cloud. The consumer interface allows the consumer to select analytes of interest for analysis. In some embodiments, the consumer interface is useful to communicate the results of an analyte analysis to the consumer. In some embodiments, the consumer interface comprises a device for consumer identity verification, such as a fingerprint reader or a retinal scanner.

In some embodiments, the system comprises a data processing station (e.g., a processor) is coupled to the consumer interface, the assay station, and optionally the sample processing station. In some embodiments, the data processing station is coupled to the internet. The data processing station can receive the raw data from the assay station, processes the raw data to obtain analyte levels, and store the analyte levels in a database. In some embodiments, the data processing station can make the analysis results (e.g., analyte levels) accessible to the consumer (e.g., through the consumer interface, or through a personal consumer account accessible over the internet).

In some embodiments, the database is divided into two parts. The first part of the database comprises the personal identifying information of all consumers whose samples were analyzed in a system provided herein. The second part comprises all other information available in consumers' personal accounts, such as health related information, including the results from the analysis of analytes of interest to the consumer. Such a database design allows the sharing and analysis of anonymized consumer health data in the second part of the database, e.g., for medical research and drug discovery purposes.

In some embodiments, the multianalyte detection system is an integrated diagnostic apparatus. In some embodiments, the integrated diagnostic apparatus comprises, a consumer interface, a sample collection station, a sample processing station, an assay station, and a processor. In some embodiments, the components of the integrated diagnostic apparatus are directly or indirectly connected to the same chassis or encased or attached to the same housing. In some embodiments, the integrated diagnostic apparatus has a height of eight feet or less, a depth of three feet or less, and a width of five feet or less. In some embodiments, the integrated diagnostic apparatus is configured to communicate with a consumer and an external database.

Figure 3:
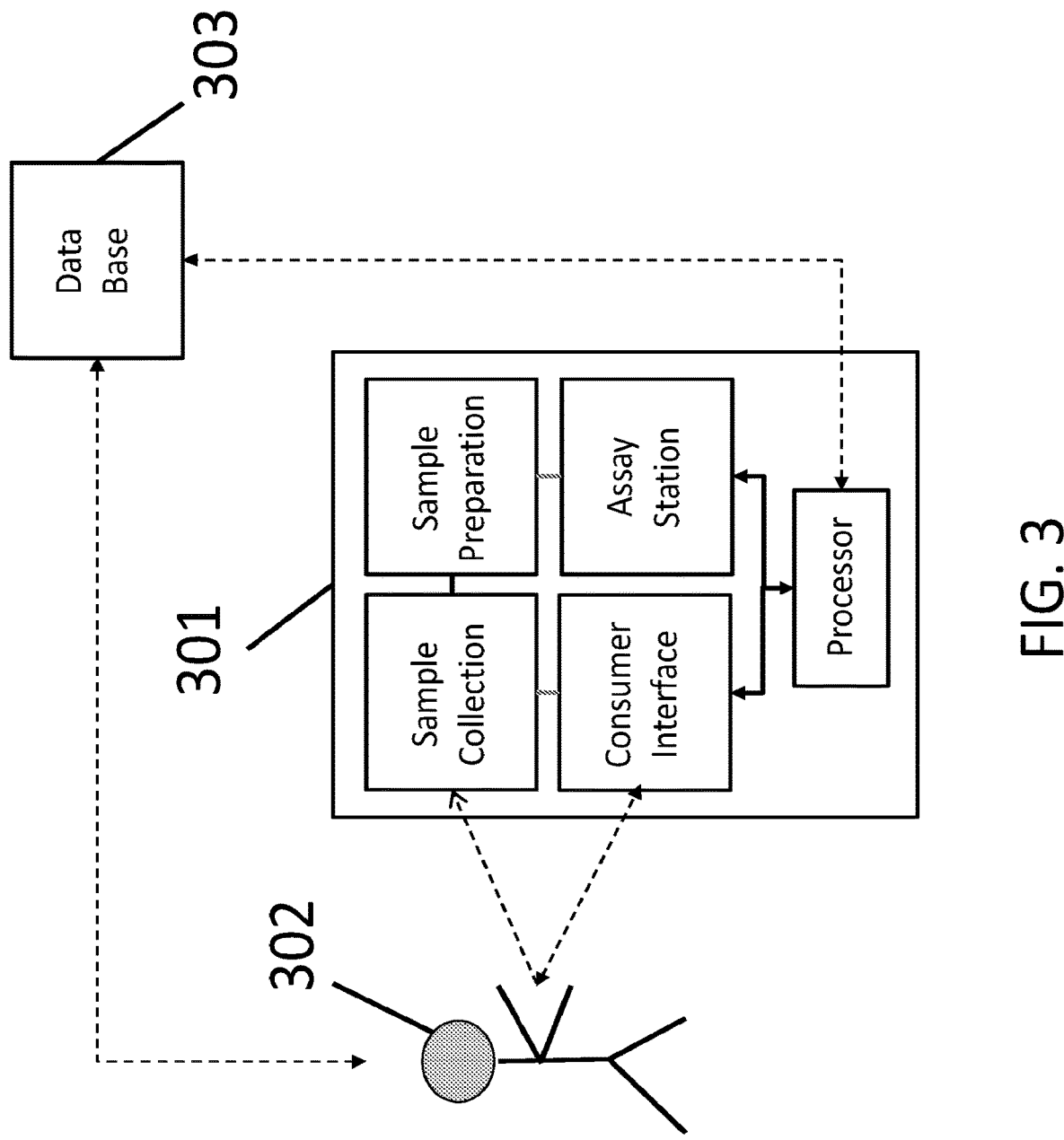
FIG. 3 shows a schematic illustrating an exemplary integrated diagnostic apparatus provided herein.

FIG. 3 shows a schematic illustrating an exemplary integrated diagnostic apparatus 301, in which a consumer interface, a sample collection station, a sample preparation station, an assay station and a processors are encased in the same housing. The integrated diagnostic apparatus 301 can communicate with a consumer 302 and an external database 303.

In some embodiments, the multianalyte detection system is a partially integrated diagnostic apparatus. A partially integrated diagnostic apparatus can integrate some components of a fully integrated system, while one or more other components are external to the apparatus. In some embodiments, the partially integrated diagnostic apparatus comprises a sample preparation station, an assay station, and, optionally, a sample collection station. In some embodiments, a consumer interface or a sample collection station are external to the partially integrated diagnostic apparatus.

In some embodiments, the multianalyte detection system comprises two or more integrated diagnostic apparatuses (e.g., fully or partially integrated). In some embodiments, the multianalyte detection system comprises 2 or more, 10 or more, 25 or more, 50 or more, 75 or more, 100 or more, 150 or more, 200 or more 250 or more, 300 or more, 350 or more, 400 or more, 450 or more, 500 or more, 600 or more, 700 or more, 800 or more, 900 or more, 1,000 or more, 2,000 or more, 3,000 or more, 4,000 or more, 5,000 or more, 6,000 or more, 7,000 or more, 8,000 or more 9,000 or more, 10,000 or more, 20 or more, 30,000 or more, 40,000 or more, 50,000 or more, 60,000 or more, 70,000 or more, 80,000 or more, 90,000 or more, or 100,000 or more integrated diagnostic apparatuses (e.g., fully or partially integrated). In some embodiments, the multianalyte detection system comprises between 1 and about 100,000, between about 10 and about 10,000, or between about 1,000 and about 10,000 integrated diagnostic apparatuses (e.g., fully or partially integrated).

Figure 4:
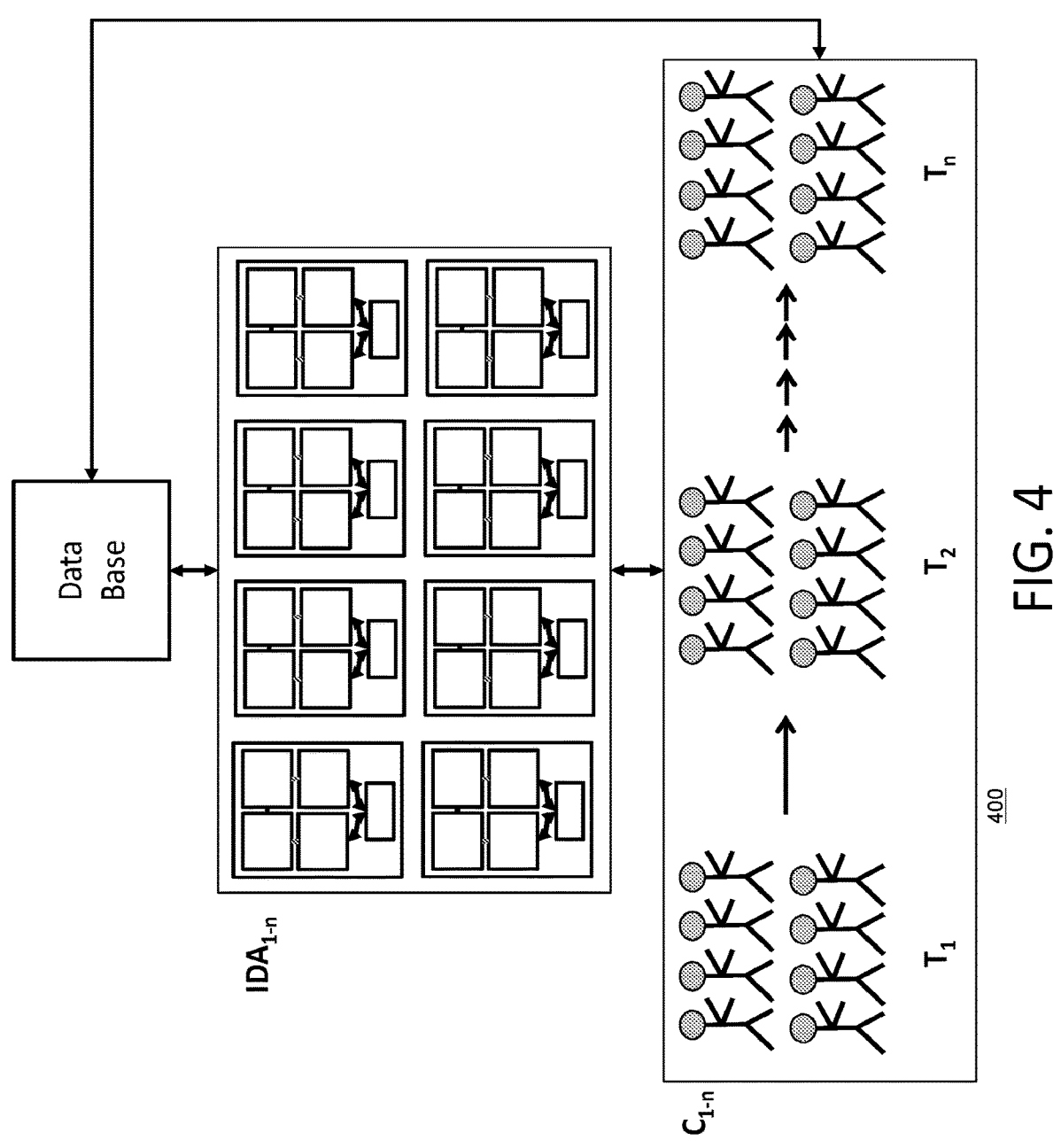
FIG. 4 shows a schematic illustrating an exemplary multianalyte detection system provided herein ($IDA_{1-n}$=plurality of n integrated diagnostic apparatuses provided herein; $C_{1-n}$=plurality of n consumers; $T_1$, $T_2$, $T_1$=plurality of timepoints $T_1$, $T_2$, and $T_n$).

FIG. 4 shows a schematic illustrating a multianalyte detection system comprising multiple integrated diagnostic apparatuses (IDA$_{1-n}$). Multiple consumers (C$_{1-n}$) can interact with the multiple diagnostic apparatuses at multiple timepoints (T$_1$, T$_2$, T$_n$) to collect longitudinal diagnostic datasets. A central database can collect and store diagnostic information collected from multiple IDAs, multiple consumers, and multiple timepoints. Individual consumers can communicate with the database to access the consumers' own diagnostic information. Consumers can, e.g., review results from an individual test, or analyze trends in diagnostic parameters over time. In some embodiments the consumer can obtain access to the anonymized aggregate data in the database, e.g., to compare the consumers' results to the results of other consumers in the database.

In some embodiments, a third party (e.g., a medical researcher or a healthcare professional) can obtain access to anonymized aggregate data in the database, e.g., for research purposes.

5.6 Illustrative Multianalyte Detection Systems

In some embodiments, the multianalyte detection systems provided herein are integrated apparatuses. In an integrated apparatus, some or all elements of the apparatus can, e.g., be located within or attached to the same housing, or some or all elements of the apparatus can be attached to the same chassis, either directly or indirectly (e.g., indirectly via another element that is directly attached to the chassis). In some embodiments, the integrated apparatus can take the form of a kiosk with the footprint, e.g., comparable to a vending machine, a photo booth, or the like. An integrated diagnostic apparatus for multianalyte detection provided herein typically integrates a consumer interface (e.g., to enable diagnostic test selection by the consumer), a sample collection and preparation station (e.g., to deposit a consumer's blood sample, process the sample, e.g., by dilution, and transfer the processed sample into a multiwell plate for testing), and an assay station to perform multianalyte testing. The integrated apparatus can operate either in a fully automated fashion, or be assisted by an operator (e.g., a skilled technician). In some embodiments, the integrated apparatus can communicate with components of a larger multianalyte detection system, e.g., a cloud-based database for data-storage or data communication to a consumer, healthcare professional, or medical researcher.

In some embodiments, the multianalyte detection system is an integrated diagnostic apparatus for multianalyte detection in a consumer sample, comprising a chassis; a consumer interface, optionally attached to the chassis, for the consumer to enter identifying information, select a multianalyte panel, or confirm the selection of a preselected multianalyte panel to be assayed in the consumer sample; a sample collection and preparation station attached to the chassis for a consumer to deposit the consumer sample and to analyze a sample characteristic (e.g., sample volume); an assay station attached to the chassis for assaying two or more analytes from the multianalyte panel, wherein the platform is configured for the placement of a multiwell plate (e.g., a traditional multiwell plate or a multiwell plate provided herein); a processor, and, optionally, a multiwell plate (e.g., a traditional multiwell plate or a multiwell plate provided herein), wherein the processor is in electrical (e.g., wireless or via an electrical cable) communication with the consumer interface to receive consumer identification information or multianalyte selection information, wherein the processor is optionally in electrical communication with the sample collection station to receive information confirming the presence of the sample or describing the sample characteristic; wherein the processor is optionally in electrical communication with the sample preparation station to receive a signal from the sample preparation station when the sample preparation is complete, and wherein the processor is in electrical communication with the assay station to receive the assay results.

In some embodiments, the processor controls the assay station and the assay station's communications with other elements of the integrated apparatus (e.g., the sample collection and sample preparation station) or with components of a larger multianalyte system outside the integrated diagnostic apparatus (e.g., a cloud-based database for data storage or communication).

In some embodiments, the consumer interface comprises a data entry device (e.g., keyboard or touchscreen); a display (e.g., computer screen), and, optionally, a consumer identification device (e.g., fingerprint reader, voice recognition device, retina scanner, image-based face-recognition device, or the like). In some embodiments, the consumer interface comprises a receiver device on the apparatus that is in direct (e.g., wireless) or indirect (e.g., via the internet) communication with a remote interface, such as a smart-phone, tablet or personal computer, configured to receive consumer information (e.g., identifying information or information related to multianalyte test selection).

In some embodiments, the integrated diagnostic apparatus comprises an operator interface (e.g., for a skilled technician), comprising a data entry device (e.g., keyboard, touchscreen, a voice recognition device), a display (e.g., computer screen), and, optionally, a barcode reader.

In some embodiments, the sample collection station comprises a sample collection device to receive the consumer sample (e.g., microneedle or vial holder); and, optionally, one or more sample verification devices to confirm the presence or integrity of the sample, a consumer's compliance with a sample deposition protocol during sample collection (e.g., sample volume; gravimetric or optical detector, e.g., a balance or camera), or a device for sample tracking (e.g., a barcode reader, RFID chip).

In some embodiments, the integrated diagnostic apparatus comprises a sample preparation station attached to the chassis to prepare the consumer sample for multianalyte detection, comprising a filtration unit or centrifugation unit, and, optionally, a sample dilution device (e.g., a liquid handling device or intermediate plate). In some embodiments, the sample preparation station comprises a sample quality control station, e.g., to assess sample contamination or sample variability (e.g., an image based system).

In some embodiments, the assay station comprises a light source (e.g., comprising source of narrow band light of 535 nm-555 nm); a detector (e.g., comprising a CMOS camera, an absorbance reader, a bulk fluorescence reader); a liquid handling device, and a platform configured for the placement of a multiwell plate (e.g., traditional or as provided herein). In some embodiments, the detector comprises three detection modules lined up next to one another. In some embodiments, the three detection modules comprise a fluorescence detection module, an absorbance reader, and a cell-enumeration module (e.g., CMOS). In some embodiments, the platform configured for the placement of a multiwell plate is movably mounted on rails that are attached to the chassis, wherein the rails are arranged underneath the detector in a parallel alignment with the line of detection modules in the detector to allow the platform to move underneath the detector from a position underneath a first detection module to a position underneath a second detection module. In some embodiments, the platform configured for the placement of a multiwell plate is rotatably mounted on the rails to allow for a multiwell plate placed on the platform (e.g., a circular multiwell plate provided herein) to rotate underneath each of the detection modules.

In some embodiments, the processor is configured to process the assay results to determine the levels of the two or more analytes assayed in the sample. In some embodiments, the processor is configured to communicate with an electronic device of the consumer (e.g., by text message, email, or the like) to inform the consumer of the analyte levels or the status of the analyte levels. In some embodiments, the electronic device of the consumer is a mobile device (e.g., consumer's smartphone) or a personal computer (e.g., in consumer's home). In some embodiments, the processor is configured to communicate with a database (e.g., in the cloud or locally, e.g., on a computer connected to the integrated diagnostic apparatus).

In some embodiments, the database comprises two parts, wherein the first part of the database comprises consumer identifying information and does not comprise information related to a consumer's medical records, and wherein the second part of the database comprises the consumer's medical records and does not comprise consumer identifying information.

In some embodiments, the dimensions of the integrated diagnostic apparatus are 400 mm×400 mm×400 mm.

In some embodiments, the sample collection device is configured to collect a sample (e.g., blood, saliva) from a consumer (e.g., disposable/sterile microneedle, disposable vial) in the sample collection station. In some embodiments, the sample collection station is configured to receive an aliquot of a sample collected from a consumer outside the sample collection station (e.g., a traditional blood collection tube for collection of venous blood, e.g., as provided by phlebotomist; aliquot of urine sample, and the like). In some embodiments, the sample collection station comprises a camera configured to record sample collection from the consumer in the sample collection station or the deposition of a sample collected outside the sample collection station. In some embodiments, the sample collection station comprises a device for measuring a sample volume.

In some embodiments, the assay station comprises a barcode reader configured to read a barcode on a multiwell plate placed on the platform in the assay station.

In some embodiments, the integrated diagnostic apparatus comprises a storage unit for two or more multiwell plates attached to the chassis (e.g., as a component of the assay station or attached to the assay station).

In some embodiments, the multiwell plate comprises a barcode. In some embodiments, the barcode encodes information related to the multiwell plate layout, analyte panels to be assayed using the multiwell plate, or multiwell plate manufacturing information. In some embodiments, the multiwell plate comprises reagents for two or more different analyte assays in two or more different pluralities of wells.

In some embodiments, the integrated diagnostic apparatus comprises a waste disposal unit attached to the chassis. In some embodiments, the waste disposal unit comprises a barcode reader configured to read the barcode of a multiwell plate in the waste disposal unit or a camera configured to detect a multiwell plate in the waste disposal unit.

In another aspect, provided herein is a multianalyte detection system comprising two or more integrated diagnostics apparatuses provided herein (e.g., 10 or more, 100 or more, 1,000 or more, 10,000 or more, or 100,000 or more). In some embodiments, the two or more integrated diagnostic apparatuses communicate with the same external database. See, e.g., FIG. 4.

5.7 Methods of Multianalyte Detection

The methods of multianalyte detection provided herein generally involve the use of multiwell plates described herein, or the use of devices or systems described herein. The methods can be applied, e.g., in a DTC diagnostics application at a POCC site (e.g., in a pharmacy or a store), or in a clinical setting (e.g., in a clinical laboratory, in a hospital).

In another aspect, provided herein is a method for multianalyte detection, comprising performing two or more different assays for two or more analytes of interest in a sample from a consumer in two or more different pluralities of wells of a multiwell plate to detect the two or more different analytes. In some embodiments, the method comprises verifying the consumer's identity. In some embodiments, the method comprises presenting the consumer with a selection of analytes of interest for testing in the two or more different assays. In some embodiments, the method comprises transferring the results of the two or more different assays to a data processing unit. In some embodiments, the method comprises presenting the results of the two or more different assays to the consumer. In some embodiments, the method comprises the sample from the consumer. In some embodiments, the method comprises performing a quality control test on the sample from the consumer, and, if the sample fails the quality control test, requesting an additional sample from the consumer, discarding the sample, not performing the two or more different assays, or not reporting the results of the two or more different assays to the consumer.

In some embodiments, selecting two or more analytes to be analyzed in the sample, comprises the consumer interacting with a consumer interface (e.g., a computer terminal, or a touchscreen), e.g., a consumer interface in a system provided herein. In some embodiments, selecting the two or more analytes comprises the consumer communicating the selection to a system operator (e.g., a medical technician), e.g., to the an operator of a system provided herein.

In some embodiments, the consumer interacting with a consumer interface comprises the consumer logging into a personal account. In some embodiments, the consumer's personal account can comprise personal information about the consumer. Such personal information can comprise, e.g., identifying information for the consumer (e.g., date and place of birth, residence address), payment information (e.g., credit card number), insurance information (e.g., health insurance), health information, genetic information (e.g., from a personal genomics service or from clinical testing), personal habits of the consumer (e.g., use of tobacco, alcohol, recreational drugs, nutraceuticals, prescription medication), and the like. Health information can comprise, e.g., information entered by the consumer (e.g., familial medical history), results from previous analyses of analytes, e.g., analyses performed on a system provided herein, information originating from a healthcare provider (e.g., imaging results). In some embodiments, the method comprises the consumer entering the information into the personal account. In some embodiments, the method comprises a third party (e.g., a healthcare provider or insurance company) entering information into the personal account. In some embodiments, the consumer can access the personal account at the POCC site. In some embodiments, the consumer can access the personal account over the internet, e.g., from his home.

In some embodiments, the consumer interface (e.g., computer terminal or touchscreen) is located at the POCC site (e.g., in a general store or pharmacy). In some embodiments, the consumer interface is internet-based. In some embodiments, the consumer interface is a mobile application, e.g., on a smart-phone or a tablet computer.

In some embodiments, the consumer interacting with a consumer interface comprises the consumer entering personal information. In some embodiments, the personal information entered by the consumer comprises identifying information, such as the consumer's name, date of birth, birthplace, residential address, driver license number, an answer to a security question, and or like. In some embodiments, the consumer interacting with a consumer interface comprises verifying the identity of the consumer. In some embodiments verifying the consumer's identity comprises analyzing the consumer's fingerprint or scanning the consumer's retina. In some embodiments, the consumer can enter the personal information at the POCC site. In some embodiments, the consumer can enter the information over the internet, e.g., from his home or on the go, using a mobile application (e.g., on a smartphone or tablet computer).

In some embodiments, verifying the consumer's identity comprises voice recognition. In some embodiments, verifying the consumer's identity comprises facial recognition technology.

In some embodiments, presenting the consumer with a selection of two or more analytes of interest for testing comprises displaying the selection to the consumer via a consumer interface, e.g., on a screen, such as a computer monitor, or the screen of a tablet or mobile device (e.g., smartphone). In some embodiments, the two or more analytes are presented independently from one another. In some embodiments, the two or more analytes are presented to the consumer as prearranged panel of analytes. Analytes can be classified and selected from different categories, such as healthcare related analytes (e.g., insulin, glucose), wellness related analytes (e.g., stress hormones), drug related analytes (e.g., opiods), or the like. Such classifications can be presented to the consumer via a consumer interface (e.g., on a computer screen or touch screen). In some embodiments, the consumer interface is configured to allow the consumer to select the two or more analytes from two or more different categories (e.g., independently or grouped into prearranged panels). In some embodiments, the consumer is configure to allow analyte selection from only a single category.

In some embodiments, the two or more different analytes comprise 2 or more, 3 or more, 4 or more, 5 or more, 6 or more, 7 or more, 8 or more, 9 or more, 10 or more, 12 or more, 15 or more, 20 or more, 25 or more, 30 or more, 35 or more, 40 or more, 45 or more, or 50 or more different analytes. In some embodiments, the two or more different analytes comprise analytes from 2 or more, 3 or more, 4 or more, 5 or more, 6 or more, 7 or more, 8 or more, 9 or more, 10 or more, 12 or more, 15 or more, 20 or more categories of analytes.

In some embodiments, the method comprises storing two or more multiwell plates in a multiwell plate storage unit connected to a multianalyte detection system described herein. In some embodiments, the method comprises transferring a set of prepackaged multiwell plates from a storage facility (e.g., a warehouse or a storage cabinet) onto a multianalyte system. In some embodiments, the method comprises transferring a single multiwell plate from the multiwell plate storage unit on the system to an assay station on the system.

In some embodiments, the method comprises reading a marker (e.g., one or two-dimensional barcode, QR code, or RFID tag) on a multiwell plate, e.g., using a barcode reader. In some embodiments, the marker is read in an assay station. In some embodiments, the marker is read in a sample processing station. In some embodiments, the marker is read on in a storage container for multiwell plates.

In some embodiments, the method comprises a step of collecting a sample from a consumer. In some embodiments, the sample is collected in a sample collection station in a system provided herein. In some embodiments, the sample is collected in a sample container.

In some embodiments, the sample container is a sterile container or pod. In some embodiments, the sample container is placed onto the multianalyte system by a skilled technician.

In some embodiments, the method comprises transferring the sample container from the sample collection station to a sample processing station. In some embodiments, the sample container is transferred from the sample collection station to the sample processing station using a conveyor belt or a robotic arm. In some embodiments, the sample container is transferred between the sample collection station and the sample processing station by an operator (e.g., a medical technician). In some embodiments, the sample processing station comprises a quality control station. In some embodiments, the sample processing station comprises a sample dilution station. In some embodiments, the sample processing station comprises a quality control station and a sample dilution station.

In some embodiments, the method further comprises optionally performing a quality control test on the sample, wherein, if the sample passes the quality control test, the sample is analyzed for analytes interest to the consumer, and, if the sample fails the quality control step, the sample is discarded, the analytes of interest are not analyzed, or the results of the analysis of the analytes of interest are not reported to the consumer. In some embodiments, the quality control test is performed prior to the analysis of analytes of interest to the consumer. In some embodiments, the quality control analysis is performed parallel to the analysis of analytes of interest to the consumer. In some embodiments, the quality control test comprises use of a multiwell plate provided herein. In some embodiments, the quality control test does not comprise use of a multiwell plate provided herein.

In some embodiments, the sample is a blood sample. In some embodiments, the blood sample is fingerprick blood. In some embodiments, the blood sample volume is between about 15 μl and about 150 μl, between about 20 μl and about 125 μl, between about 25 μl and about 100 μl, or between about 50 μl and about 70 μl. In some embodiments the blood sample volume is about 10 μl, about 15 μl, about 20 μl, about 25 μl, about 30 μl, about 35 μl, about 40 μl, about 45 μl, about 50 μl, about 55 μl, about 60 μl, about 65 μl, about 70 μl, about 75 μl, about 80 μl, about 85 μl, about 90 μl, about 95 μl, or about 100 μl. In some embodiments, the blood sample volume is between about 50 μl and about 100 μl. In some embodiments, the blood sample volume is about 55 μl. Devices and methods for collecting fingerprick blood are known in the art. Exemplary devices useful for collecting fingerprick blood can include, e.g., devices by Seventh Sense Biosystems (e.g., using TAP Touch-Activated Phlebotomy™ or HemoLink™ technology). In some embodiments, fingerprick blood collected from a consumer comprises less than 20%, less than 15%, less than 10%, less than 5%, less than 3%, less than 2%, or less than 1% interstitial fluid. In some embodiments, fingerprick blood collected from the consumer comprises at least 80%, at least 85%, at least 90%, at least 95%, at least 97%, at least 98%, or at least 99% venous blood. In some embodiments, interstitial fluid is not detectable in fingerprick blood collected from the consumer.

In some embodiments, the blood sample is obtained by venipuncture (e.g., using a needle). In some embodiments, the blood sample is collected by a phlebotomist. In some embodiments the blood sample is collected with an evacuated tube or a vacuum tube (e.g., Vacutainer® by Becton Dickinson & Co, Vacuette® by Greiner Bio-One GmbH). In some embodiments, the blood sample is between about 1 ml and about 50 ml, between about 5 ml and about 30 ml and between about 10 ml and about 20 ml. In some embodiments, the blood sample is about 15 ml. In some embodiments, the blood sample is an aliquot from a larger sample, e.g., an aliquot between about 1 μl and about 250 μl, between about 5 μl and about 200 μl, between about 10 μl and about 175 μl, between about 15 μl and about 150 μl, between about 20 μl and about 125 μl, between about 25 μl and about 100 μl, or between about 50 μl and about 70 μl. In some embodiments, the aliquot is between about 1 μl and about 10 μl. In some embodiments, the aliquot is between about 50 picoliter (50 μl) and about 100 nanoliter (100 nl).

In some embodiments, the quality control step comprises determining the ratio of venous blood and interstitial fluid in the fingerprick blood. In some embodiments, the fingerprick blood sample fails the quality control step if the sample comprises more than 1%, more than 3%, more than 5%, more than 10%, more than 20%, more than 25%, or more than 30% of interstitial fluid.

In some embodiments, the quality control step comprises comparing the level of a quality control analyte in two or more independent samples from a consumer. In some embodiments, the two or more independent samples from the consumer comprise two or more successive drops of fingerprick blood (e.g., 2, 3, 4, 5, 6, 7, 8, 9, or 10 successive drops). In some embodiments, the sample fails the quality control step if the average percent coefficient of variation (CV) of the quality control analyte for two or more independent samples from the consumer is more than 1%, more than 1.5%, more than 2%, more than 2.5%, more than 3%, more than 3.5%, more than 4%, more than 4.5%, more than 5%, more than 5.5%, more than 6%, more than 6.5%, more than 7%, more than 7.5%, more than 8%, more than 8.5%, more than 9%, more than 9.5, or more than 10%.

In some embodiments, the quality control test comprises determining the drop-to-drop variation of a component of fingerprick blood. In some embodiments, the component of fingerprick blood comprises hemoglobin concentration, total white blood cell (WBC) count, three-part WBC differential or platelet count. In some embodiments, the quality control test fails if the coefficient of variation (CV) in two or more successive drops of finger prick blood is greater than 1%, greater than 2%, greater than 3%, greater than 4%, greater than 5%, greater than 6%, greater than 7%, greater than 8%, greater than 9%, or greater than 10%. In some embodiments, the two or more successive drops of fingerprick blood are 2, 3, 4, 5, 6, 7, 8, 9, or 10 successive drops of fingerprick blood.

In some embodiments, the quality control step comprises comparing the level of a quality control analyte in a sample from the consumer to a reference level. In some embodiments, the reference level is the median, mean, or average level of the quality control analyte in a healthy consumer. In some embodiments, the reference level is the median, mean, or average level of the quality control analyte in a consumer sharing one or more disease conditions with the consumer whose sample is tested. In some embodiments, the reference level is the median, mean or average level of the quality control analyte of all consumers whose quality control analyte levels are recorded in a database (e.g., a database associated with a DTC diagnostics system or device). In some embodiments, the reference level is a historical median, mean, or average level of the quality control analyte previously recorded over a period of time for the consumer whose sample is tested. In some embodiments, the period of time is a period of at least 2 weeks, at least 1 month, at least 6 weeks, at least 2 months, at least 3 months, at least 6 months, at least 9 months, at least 12 months, at least 18 months, at least 2 years, or at least 3 years. In some embodiments, the sample fails the quality control step if the level of the quality control analyte in the sample from the consumer deviates from the reference level by at least 1.5, at least 2, at least 2.5, at least 3, at least 3.5, at least 4, at least 4.5, or at least 5 standard deviations of the mean, median, or average reference level. In some embodiments, the sample fails the quality control step if the level of the quality control analyte in the sample from the consumer is at least 10%, at least 20%, at least 30%, at least 40%, at least 50%, at least 60%, at least 70%, at least 80%, at least 90%, at least 100%, at least 200%, at least 300%, at least 400%, at least 500%, at least 600%, at least 700%, at least 800%, at least 900%, or at least 1,000% higher than the reference value. In some embodiments, the sample fails the quality control step if the level of the quality control analyte in the sample from the consumer is at least 10%, at least 20%, at least 30%, at least 40%, or at least 50% lower than the reference value.

The quality control analyte can be any analyte detectable in a sample from the consumer to be analyzed for the analytes of interest to the consumer. In some embodiments, the quality control analyte comprises, e.g., hemoglobin, WBC count, lymphocyte count, granulocyte count, platelet count, or one or more analytes of interest to the consumer.

In some embodiments, performing a quality control test on a sample comprises measuring the sample volume. In some embodiments, a sample passes the quality control test if the sample volume is equal to or exceeds a predetermined minimum sample volume. In some embodiments, the predetermined minimum sample volume is 1 µl, 2 µl, 3 µl, 4 µl, 5 µl, 6 µl, 7 µl, 8 µl, 9 µl, 10 µl, 12 µl, 15 µl, 20 µl, 25 µl, 30 µl, 35 µl, 40 µl, 45 µl, 50 µl, 75 µl or 100 µl.

In some embodiments, the method further comprises centrifuging the sample.

In some embodiments the method further comprises diluting the sample. In some embodiments, the sample is diluted in a multiwell plate provided herein. In some embodiments, the sample is diluted and transferred to a multiwell plate provided herein. In some embodiments, diluting the sample comprises preparing a serial dilution of the sample. In some embodiments, sample dilutions are prepared in a sample dilution station, e.g., a sample dilution station in a system provided herein. In some embodiments, the sample dilution station is a component of a sample processing station, e.g., a sample processing station in a system provided herein (e.g., the sample dilution station is encased in the same housing as the sample processing station). In some embodiments, sample dilutions are prepared, e.g., using a piezoelectric or an acoustic liquid handling device (e.g., Labcyte Echo®).

In some embodiments, diluting the sample comprises preparing a serial dilution of the sample. In some embodiments, the serial dilution comprises a serial 2-fold, 3-fold, 5-fold or 10-fold dilution, such as serial 2-point, 3-point, 4-point, 5-point, 6-point, 7-point, 8-point, 9-point, 10-point, 11-point or 12-point dilution. In some embodiments, the sample is not diluted serially, e.g., a sample dilution series can comprise a 1:3, 1:5, 1:10, 1:100, and a 1:500 dilution of sample. In some embodiments, the dilution factors or numbers of dilutions in a dilution series are dependent on which two or more analytes of interest to the consumer are selected.

In some embodiments, two or more different assays performed in two or more pluralities of different wells of the multiwell plate comprise 2, 3, 4, 5, 6, 7, 8, 9, 10, 11, 12, 13, 14, 15, 16, 17, 18, 19, 20, 21, 22, 23, 24, 25, 26, 27, 28, 29, or 30 different assays performed in 2, 3, 4, 5, 6, 7, 8, 9, 10, 11, 12, 13, 14, 15, 16, 17, 18, 19, 20, 21, 22, 23, 24, 25, 26, 27, 28, 29, or 30 pluralities of different wells of the multiwell plate.

In some embodiments, the method further comprises transferring a multiwell plate provided herein comprising sample or a sample dilution from a processing station or a sample dilution station, to an assay station, e.g., in a system provided herein. In some embodiments, the multiwell plate is transferred using, e.g., a conveyor belt or a robotic arm.

In some embodiments, the two or more different assays performed in the two or more pluralities of different wells of the multiwell plate comprise two or more different readout formats. Such readout formats comprise, e.g., without limitation, fluorescence, absorbance, microscopic imaging (e.g., high-content imaging), Raman, circular dichroism, surface plasmon resonance, and mass spectrometry. Fluorescence readouts can include, e.g., without limitation fluorescence intensity, time-resolved fluorescence, fluorescence correlation, fluorescence associated cell sorting. Absorbance readouts include, e.g., without limitation, absorbance in the visible, ultraviolet, or infra-red spectral ranges.

In some embodiments, the two or more different assays performed in the two or more pluralities of different wells of the multiwell plate comprise assays for two or more different analyte classes. Analyte classes can include, e.g., without limitation, small molecule analytes (e.g., <500 Da, glucose, free fatty acids, cholesterol, opiods), large molecule analytes (polypeptides or proteins, e.g., cytokines, insulin, hemoglobin, albumin), or cells (e.g., red blood cells, white blood cells, platelets).

In some embodiments, the two or more different assays performed in the two or more pluralities of different wells of the multiwell plate comprise two or more different assay technologies. Assay technologies can include, e.g., without limitation, homogeneous assay, heterogeneous assay (e.g., using beads or a surface, such as a well surface), mix-and-read assay, kinetic assay, endpoint assay, substrate-turnover assay, biochemical assay, cell-based assay.

In some embodiments, the two or more different assays performed in the two or more pluralities of different wells of the multiwell plate comprise two or more different assay technologies and two or more different assay readouts. In some embodiments, the two or more different assays performed in the two or more pluralities of different wells of the multiwell plate comprise assays for analytes of two or more analyte classes (e.g., a large molecule or small molecule analyte and a cell), using two or more different assay technologies (e.g., substrate-turnover and cell-based assay) and two or more different assay readouts (e.g., fluorescence and absorbance).

In some embodiments, the two or more different assays performed in the two or more pluralities of different wells of the multiwell plate comprise at least one absorbance assay and a fluorescent assay. In some embodiments, the two or more different assays comprise at least one absorbance assay for a protein analyte (e.g., absorbance at 280 nm, 540 nm, 592 nm) and one fluorescent substrate turnover assay for a small molecule metabolite (e.g., glucose). In some embodiments, the absorbance assay is an endpoint assay (e.g., readout once (end) or twice (beginning and end)) and the fluorescent assay is a kinetic assay (read out continuously or repeatedly throughout the assay reaction period).

In some embodiments, the two or more different assays performed in the two or more pluralities of different wells of the multiwell plate comprise at least one absorbance assay and two fluorescent assays. In some embodiments, the two or more different assays comprise at least one absorbance assay for a protein analyte (e.g., absorbance at 280 nm, or 540 nm), one fluorescent substrate turnover assay for a small molecule metabolite (e.g., glucose) and one fluorescent assay for a cell (e.g., a white blood cell). In some embodiments, the absorbance assay is an endpoint assay (e.g., readout once (end) or twice (beginning and end)), one fluorescent assay is a kinetic assay (read out continuously or repeatedly throughout the assay reaction period) and one fluorescent assay is an endpoint assay.

In some embodiments, the two or more different assays performed in the two or more pluralities of different wells of the multiwell plate comprise similar lower limits of detection (e.g., smallest analyte concentration that can be reliably detected, e.g., resulting in an assay signal of >26 above background). In some embodiments, the two or more different assays performed in the two or more different wells of the multiwell plate comprise lower limits of detection that are at least 10-fold, at least 1,000-fold, at least 10,000-fold, at least 100,000-fold, or at least 1,000,000-fold different from each other (e.g., the lower limit of detection is about 1 nM for a first assay and about 1 mM for a second assay). In some embodiments, at least one of the two or more assays comprises a lower limit of detection between 0.1 nM and 10 nM. In some embodiments, at least one of the two or more assays comprises a lower limit of detection between 10 nM and 1 µM. In some embodiments, at least one of the two or more assays comprises a lower limit of detection between 1 µM and 100 µM. In some embodiments, at least one of the two or more assays comprises a lower limit of detection between 100 µM and 10 mM. In some embodiments, at least one of the two or more assays comprises a lower limit of detection between 0.1 nM and 10 nM and at least one of the two or more assays comprises a lower limit of detection between 10 nM and 1 µM. In some embodiments, at least one of the two or more assays comprises a lower limit of detection between 0.1 nM and 10 nM and at least one of the two or more assays comprises a lower limit of detection between 1 µM and 100 µM. In some embodiments, at least one of the two or more assays comprises a lower limit of detection between 0.1 nM and 10 nM and at least one of the two or more assays comprises a lower limit of detection between 100 µM and 10 mM. In some embodiments, at least one of the two or more assays comprises a lower limit of detection between 0.1 nM and 10 nM, at least one of the two or more assays comprises a lower limit of detection between 10 nM and 1 µM, and at least one of the two or more assays comprises a lower limit of detection between 1 µM and 100 µM. In some embodiments, at least one of the two or more assays comprises a lower limit of detection between 0.1 nM and 10 nM, at least one of the two or more assays comprises a lower limit of detection between 10 nM and 1 µM, at least one of the two or more assays comprises a lower limit of detection between 1 µM and 100 µM, and at least one of the two or more assays comprises a lower limit of detection between 100 µM and 10 mM.

In some embodiments, the two or more different assay performed in the two or more pluralities of different wells of the multiwell plate comprise an assay described, e.g., in Taosheng Chen, A Practical Guide To Assay Development and High-Throughput Screening in Drug Discovery, CRC Press, 1$^{st}$ ed., 2009; Lisa K. Minor, Handbook of Assay Development in Drug Discovery, CRC Press, 1$^{st}$ ed., 2006; Ge Wu, Assay Development, Wiley, 1$^{st}$ ed., 2010; Uma Prabhakar, Validation of Cell-based Assays in the GLP Setting, Wiley, 1$^{st}$ ed., 2008; Masood Kahn and John Findlay, Ligand-Binding Assays, Wiledy, 1$^{st}$ ed., 2009; David Wild, Immunoassays, Elsevier Science; 4$^{th}$ ed., 2013, and Benjamin Blass, Basic Principles of Drug Discovery and Development, Academic Press, 1$^{st}$ ed., 2015.

In some embodiments, one or more assay performed on a multiwell plate provided herein comprises adding sample (e.g., an aliquot of a sample dilution) to a well comprising a dried assay reagent (e.g., a reaction buffer component, an enzyme, an enzyme substrate, an antibody, a cell). In some embodiments, one or more assays performed on the multiwell plate comprise adding a reaction buffer to a well of the multiwell plate comprising a dried reagent, e.g., to resuspend the dried reagent. In some embodiments, the reaction buffer is transferred to the well comprising the dried reagent from a reagent well on the multiwell plate (e.g., a reagent well located in the center of a circular plate). In some embodiments, all assays performed on the multiwell plate comprise adding reaction buffer or sample to a well comprising a dried reagent.

In some embodiments, one or more assay performed on a multiwell plate provided herein comprises assaying a positive or negative control sample on the same multiwell plate on which the sample from the consumer is assayed. In some embodiments, a positive control sample comprises an analyte reference curve (e.g., a serial dilution of an analyte).

In some embodiments, the two or more different assays performed in the two or more pluralities of different wells of the multiwell plate meet minimum assay performance standards. In some embodiments, the Z-factor for each of the two or more different assays (e.g., 2, 3, 4, 5, 6, 7, 8, 9, 10, or more different assays) is >0.5, >0.6, >0.7, >0.8, or >0.9. A method for determining the Z-factor of an assay is described, e.g., in Zhang J H, et al. (1999). "A simple statistical parameter for use in evaluation and validation of high throughput screening assays". Journal of Biomolecular Screening 4: 67-73. In some embodiments, the CV values of positive and negative control wells on the multiwell plate for each of the two or more different assays are <10%, <9%, <8%, <7%, <6%, <5%, <4%, <3%, <2%, or <1%.

In some embodiments, one or more control samples are tested for one or more of the two or more different assays performed in a multiwell plate provided herein. Control samples typically comprise known concentrations of an analyte of interest. In some embodiments, control samples are tested along with a sample of interest at two or more concentrations. Control samples can comprise, e.g., a "high analyte" control resulting in a signal near the high end of a dynamic signal range of an assay, a "low analyte" control resulting in a signal near the lowest limit of detection of an assay, a "medium analyte" control resulting in a signal near the midpoint of the dynamic range of an assay, or combinations thereof. In some embodiments, control samples comprise a dilution series, such as an 8-point or 12-point dilution series that covers the dynamic range of an assay. In some embodiments, full dilutions series are run at regular, intervals to calibrate an assay station or system provided herein (e.g., once per day, once per week, once per month, or the like). In some embodiments, selected control samples, e.g., a high, mid or low analyte control, can be included on a multiwell plate for one or more analytes of interest, or for all analytes of interest, when testing a sample from a consumer, e.g., to validate or quality control a given assay.

In some embodiments, the two or more different assays performed in the two or more pluralities of different wells of the multiwell plate are performed in parallel. In some embodiments, the two or more different assays have overlapping reaction times (e.g., the assay started last is started prior to termination of the assay terminated first). In some embodiments, the two or more different assays do not have overlapping reaction times (e.g., at least one assay is completed before at least one other assay performed on the same multiwell plate is started). In some embodiments, the two or more different assays are started within a period of less than 10 min, less than 5 min, less than 3 min, less than 2 min, or less than 1 min of each other. In some embodiments, the two or more different assays are terminated within less than 10 min, less than 5 min, less than 3 min, less than 2 min, or less than 1 min of each other. In some embodiments, the two or more different assays are completed within less than 12 h, less than 9 h, less than 6 h, less than 3 h, less than 1.5 h, less than 1.0 h. less than 45 min, less than 30 min, less than 10 min, or less than 5 min.

The reaction times of two or more different assays performed in two or more pluralities of different wells of a multiwell plate provided herein can be independently selected. In some embodiments, the two or more different assays have the same reaction times. In some embodiments, the two or more different assays have different reaction times.

The two or more different assays performed in two or more pluralities of different wells of the multiwell plate can be started or terminated independently of each other. In some embodiments, one or more assay (e.g., a "mix-and-read" assay) is started by adding sample (e.g., diluted sample) into a well of the multiwell plate comprising assay reagents (e.g., dried assay reagents). In some embodiments, all assays performed on the multiwell plate are started by adding sample into a well of the multiwell plate comprising assay reagents (e.g., dried assay reagents). In some embodiments, one or more assay performed on the multiwell plate is started by adding one or more assay reagents to a well of the multiwell plate comprising sample and, optionally, one or more assay reagents.

In some embodiments, the methods provided herein further comprise repeating a method provided herein two or more times over a period of time. In some embodiments, the analysis is repeated 2 or more times, 3 or more times, 5 or more times, 10 or more times, 15 or more times, 20 or more times, 25 or more times, 50 or more times, or 100 or more times over a period of 1 week, 2 weeks, 1 month, 6 weeks, 2 months, 3 months, 6 months, 9 months, 1 year, 18 months, 2 years, 30 months, 3 years, 4 years, 5 years, or more. In some embodiments, the analysis is repeated with the same two or more analytes. In some embodiments, the analysis is repeated with a subset of the same two or more analytes.

In some embodiments, the methods provided herein further comprise reporting assay results to the consumer. In some embodiments, the results are reported at the POCC site (e.g., in a general store or a pharmacy), e.g., at a computer terminal. In some embodiments, the results are made available to the consumer through the consumer's personal account (e.g., a consumer can log on to the personal account and view the results). In some embodiments, the results can be accessed by the consumer via the internet, e.g., on the consumer's personal computer or through a smartphone or tablet computer application.

In some embodiments, reporting assay results to the consumer comprises providing a comparison of results obtained on a certain day with historical results to facilitate the tracking of results over time. In some embodiments, reporting assay results to the consumer comprises providing comparative data to the consumer to put the consumer's assay results (e.g., analyte levels) into perspective relative to the results of other consumers, e.g., of the same age, from the same geographic region, or sharing similar habits with the consumer.

In some embodiments, reporting assay results to the consumer comprises providing a recommendation to the consumer (e.g., provided by a computer algorithm). In some embodiments, the recommendation comprises options for a medical treatment (e.g., a referral to a doctor), dietary changes (e.g., foods, recipes), product recommendations (e.g., nutraceuticals, vitamins, etc.) behavioral changes (e.g., exercise, smoking cessation).

In some embodiments, the methods provided herein comprise storing assay results of all consumers obtained with a method provided herein in a database (e.g., as anonymized data).

In some embodiments, the methods provided herein do not comprise a sample storage step, e.g., such as a freeze-thaw step.

In some embodiments, the methods provided herein comprise a seamless integration of sample collection from the patient (e.g., fingerprick) to sample preparation (e.g., centrifugation, bulk sample dilution, dispensing of sample into multiwell plate), sample testing (e.g., start of biochemical or cell-based assays in multiwell plate) and the reporting of test results to the consumer. In some embodiments, sample preparation begins within 60 min, within 45 min, within 30 min, within 20 min, within 15 min, within 10 min, within 5 min, within 3 min, or within 1 min following sample collection. In some embodiments, sample testing in a multiwell plate (e.g., a traditional plate or a multiwell plate provided herein) begins within 60 min, within 45 min, within 30 min, within 20 min, within 15 min, within 10 min, within 5 min, within 3 min, or within 1 min following sample collection. In some embodiments, sample testing begins within 60 min, within 45 min, within 30 min, within 20 min, within 15 min, within 10 min, or within 5 min following sample collection. In some embodiments, sample testing is completed within 12 hrs, within 10 hrs, within 8 hrs, within 6 hrs, within 4 hrs, within 3 hrs, within 2 hrs, within 90 min, within 60 minutes, within 45 min, within 30 min, or within 20 min following sample collection. In some embodiments, test results are communicated to the customer (e.g., by email) or accessible in a database within 12 hrs, within 10 hrs, within 8 hrs, within 6 hrs, within 4 hrs, within 3 hrs, within 2 hrs, within 90 min, within 60 minutes, within 45 min, within 30 min, or within 20 min from sample collection.

5.8 Samples

In some embodiments, the sample is a biological sample obtained from a consumer. In some embodiments, the biological sample is a liquid sample. In some embodiments, the liquid sample is a blood sample (e.g., whole blood, plasma, or serum), a urine sample, or any other body fluid (e.g., amniotic fluid, bile, breast milk, cerebrospinal fluid, gastric acid, lymph, mucus (e.g., nasal drainage or phlegm), pericardial fluid, peritoneal fluid, pleural fluid, pus, rheum, saliva, semen, sputum, synovial fluid, sweat, tears, vaginal secretion, vomit, and the like).

The sample can be obtained non-invasively or invasively. Invasive sample collection can comprise, e.g., sample collection using an intravenous or hypodermic needle. In some embodiments, the sample can be obtained by fingerprick using a fingerprick device. Fingerprick devices that can be used in the methods provided herein comprise, without limitation, a TAP Touch Activated Phlebotomy™ device by Seventh Sense Biosystems or a HemoLink™ device by Tasso, Inc.

In some embodiments, the consumer is a healthy human. In some embodiments, the healthy human is a member of a normal control group in a clinical trial.

In some embodiments, the consumer has certain habits or traits, such as smoking, diet (e.g., western diet, Mediterranean diet, and the like), work-related (workaholic, night-shifts), exercise (e.g., frequent, infrequent, cardio, muscle mass, and the like), genetic predisposition (e.g., to depression, diabetes, and the like).

In some embodiments, the consumer is a human patient having a disease, disorder, or other condition (e.g., a metabolic disease, a genetic disorder, an inflammatory disease, an autoimmune disease, a neurodegenerative disorder, a psychiatric disorder and the like).

In some embodiments, the sample is a human blood sample. In some embodiments, the human blood sample is obtained using a fingerprick device.

5.9 Analytes

Analytes, or clinical parameters, that can be analyzed using the multiwell plates, systems, or methods described therein can comprise analytes or clinical parameters related to a consumer's disease condition, a consumer's general health status, wellness or life-style, a consumer's genotype, or combinations thereof.

The analytes described herein can include any molecular or cellular component of a biological sample. In some embodiments, analytes include a protein (e.g., PSA), a nucleotide (e.g., an mRNA expression level or DNA sequence), a sugar (e.g., glucose, or a posttranslational protein modification), a lipid (e.g., triglycerides) or lipid particle (e.g., LDL, HDL, VLDL, and the like), a metabolite (e.g., lactate, pyruvate), a metal ion or mineral (e.g., $Na^+$, $Fe^{2+}$), a vitamin (e.g., ascorbic acid), a cell (e.g., white blood cell, platelet, virus, pathogen cell, such as a bacterium or a eukaryotic pathogen), or combinations thereof. Analytes can be analyzed qualitatively (e.g., presence or absence) or quantitatively (e.g., analyte concentration or number of analytes per volume). Analyte concentrations can be expressed in absolute terms (e.g., analyte concentration in a sample) or relatively (e.g., percent of a population).

In some embodiments, a consumer's disease condition can comprise, e.g., without limitation, a metabolic disorder (e.g. diabetes, obesity, metabolic syndrome, and the like), a liver disease (e.g., cirrhosis), a kidney disease (e.g., acute or chronic kidney disease, kidney cancer), a pancreas disease (e.g., acute pancreatitis, chronic pancreatitis, hereditary pancreatitis, pancreas cancer), an inflammatory disorder (e.g., rheumatoid arthritis, inflammatory bowel disease), a cardiovascular disorder (e.g., angina, myocardial infarction, stroke, atherosclerosis), an immune or autoimmune disorder (e.g., lupus erythematosus, celiac disease), a cancer (e.g., multiple myeloma, lymphoma, leukemia, prostate cancer, breast cancer, and the like), an infectious disease (e.g., Lyme Disease, HIV, sexually transmitted diseases (STDs), and the like), an endocrine disorder (e.g., Cushing's Syndrome, Growth Hormone Deficiency), a blood disorder (e.g., anemia, a bleeding disorder, such as hemophilia, or blood cancer), a psychiatric or behavioral disorder or condition (e.g., attention deficit disorder), and others.

In some embodiments, analytes or clinical parameters relating to a consumer's disease condition can comprise, e.g., without limitation, adenovirus DNA, alanine aminotransferase (ALT/SGPT), albumin, alkaline phosphatase (ALP), alpha-1-acid glycoprotein, alpha-1-antitrypsin (e.g., total), alpha-fetoprotein (AFP), amphetamines, amylase, red blood cell (RBC) antibody, antinuclear antibodies (ANA), apolipoprotein (e.g., apo A-1, apo B), aspartate aminotransferase (AST/SGOT), B-cell count, beta-2 microglobulin, bilirubin (e.g., direct or total), blood urea nitrogen (BUN), borrelia antibody, brain natriuretic peptide (BNP), calcitonin, calcium (e.g., blood, urine), cancer antigens (e.g., CA 125, CA 15-3, CA 27.29, CA 19-9), carbon dioxide, carcinoembryonic antigen (CEA), cardiolipin antibody (ACA, e.g., IgG), complete blood count (CBC), CD4 or CD8 counts (e.g., absolute counts or ratios), *Chlamydia tachomatis*, chloride (e.g., blood, urine), cholesterol, cholinesterase, complement component 3 or 4 antigens, cortisol (e.g., total), C-peptide, C-reactive protein (CRP, e.g., CRP—High Sensitivity (hsCRP)), creatine kinase, creatinine (e.g., bood or urine), cyclic citrullinated peptide (CCP) antibody, IgG, cystatin C, cytomegalovirus (CMV) antibody (e.g., IgG or IgM), D-dimer, deamidated gliadin peptide (DGP) antibody (e.g., IgA or IgG), dehydroepiandrosterone sulfate (DHEA-S), deoxypyridinoline crosslinks (DPD) (collagen crosslinks, e.g., urine), double-stranded DNA (dsDNA) antibody (e.g., IgG), *E. coli* Shiga-like toxin, EBV early D Antigen (EA-D), EBV nuclear antibody, EBV viral capsid antigen (VCA), EBV viral capsid antigen (VCA), endomysial antibody (EMA, e.g., IgM or IgG), erythrocyte sedimentation rate (ESR/Sed Rate), extractable nuclear antigen antibodies (ENA panel) (RNP, Smith, SSA, SSB, SCO-70, JO-1), ferritin, fibrinogen, gastrin, glucose, growth hormone (HGH), *Helicobacter pylori* (*H. pylori*), IgG, hematocrit (HCT), hemoglobin (HGB), hemoglobin A1c (HbA1c), hepatitis A (HAV) antibody (e.g., IgM, total), hepatitis B (HBV) core antibody (e.g., IgM, total), hepatitis B (HBV) surface antibody (HBsAb; e.g., total), hepatitis B (HBV), DNA, hepatitis C (HCV) antibody, hepatitis C (HCV) genotype, hepatitis C (HCV), RNA, HER-2/neu, herpes simplex 1 (HSV1; e.g., IgG), herpes simplex 2 (HSV2; e.g., IgG), high-density lipoprotein (HDL), human immunodeficiency virus 1 (HIV-1; e.g., RNA), HIV-1/HIV-2 (e.g., antigen or antibody), homocysteine, immunoglobulins (e.g., IgA, IgG, IgM, IgE, IgG, IgM), IGF-1 (insulin-like growth factor 1), insulin, iron, iron binding capacity (IBC; e.g., total (TIBC)), lactate dehydrogenase, lead, lipase, low-density lipoprotein (LDL), lymphocyte enumeration, magnesium, measles, mumps, and rubella (MMR) immunity, microalbumin (e.g., urine), myoglobin, *Neisseria* gonorrhea (e.g., DNA), natural killer cells (NKC; e.g., total count), ova & parasites, parathyroid hormone (PTH), partial thromboplastin time (PTT), phosphorus, inorganic, platelets, potassium (e.g., blood, urine), prealbumin, prostate specific antigen (PSA, e.g., free or total), protein (e.g., total, e.g.; blood or urine), prothrombin pime (PT/INR), red blood cell count (RBC), reticulocyte count (RC), rheumatoid factor (e.g., total), rubella (Measles) antibody (e.g., IgG or IgM), sex hormone-binding globulin (SHBG), sodium (e.g., blood or urine), streptolysin O antibody (ASO; e.g., titer), T-cell (e.g., total count), triiodothyronine, thyroglobulin, thyroglobulin antibodies (TAA), thyroid peroxidase (TPO) antibody, thyroid stimulating hormone (TSH), thyroxine binding globulin (TBG), thyroxine (e.g., free T4 or total T4), tissue transglutaminase (tTG) antibody (e.g., IgA or IgG), *toxoplasma* (e.g., IgG or IgM), transferrin, triglycerides, triiodothyronine (e.g., free T3 or total T3), troponin I (tCNI), tuberculosis, uric acid, Varicella-zoster (VZV) antibody, and white blood cell count (WBC).

In some embodiments, a consumer's general health status, wellness or life-style can comprise or be affected by, e.g., without limitation, allergies/hypersensitivities, blood pressure, body weight (e.g., body-mass-index), diet (e.g., Western diet, Mediterranean diet, processed foods, home-cooked meals), drinking habits (e.g., frequency, quantity, or type of alcohol consumption), drug use (e.g., prescription drugs, recreational drugs, doping), environmental factors (e.g., pollution, climate), exercise habits (e.g., frequency, intensity, type of exercise), fertility, pregnancy, rest period (e.g., day or night-time, duration, frequency), smoking habits, stress levels (e.g., chronic, acute), vacation schedule, work schedule, and other factors.

In some embodiments, analytes or clinical parameters relating to a subject's general health status, wellness or life-style can comprise, e.g., without limitation, ACTH (corticotropin), alpha-fetoprotein (AFP; e.g., maternal), amphetamine, androstenedione, anti-mullerian hormone (AMH), apolipoprotein (e.g., apo A-1, apo B), barbiturates (e.g., urine), benzodiazepines (e.g., urine), cortisol (e.g., total), cyclosporine A, ecstasy (MDMA), estradiol, estriol (e.g., unconjugated), estrone, ethanol, folate (folic acid), follicle stimulating hormone (FSH), gamma-glutamyltransferase (GGT), glucose, hCG—chorionic gonadotropin (e.g., blood or urine, qualitative or quantitative), insulin, lithium, low-density lipoprotein (LDL), marijuana (THC), methadone (dolophine), methamphetamines, opiates, phencyclidine (PCP), progesterone, prolactin, propoxyphene, testosterone (e.g., free or total), tricyclic antidepressants (e.g., urine), vitamin B-12, vitamin D 25-OH.

In some embodiments, a subject's genotype can comprise genes related to a subject's health or disease conditions (e.g., life expectancy, disease susceptibility), or other physical or mental traits (e.g., energy level, athletic abilities, intelligence). In some embodiments, a subject's genotype can comprise genes related to a subject's ancestry (e.g., family ties, geographic origins)

In some embodiments, the analytes, or clinical parameters, that can be analyzed using the multiwell plates, systems, or methods described therein can comprise a biomarker (e.g., biomarker level in a patient) analyzed in connection with a pharmaceutical treatment of a patient, e.g., a small molecule drug or biotherapeutic (e.g., an antibody or other recombinant protein) treatment. In some embodiments, the biomarker is analyzed in the course of a clinical trial, e.g., to analyze the efficacy of an clinical drug candidate in a patient, to analyze a patient's compliance with the treatment regimen, or to select a patient who may benefit from the treatment. In some embodiments, the biomarker is analyzed in connection with a marketed therapy, such as a small molecule drug approved by the United States Food and Drug Administration, e.g., as a companion diagnostic.

Some analytes or clinical parameters analyzed using the methods, systems or devices described herein can relate to more than one categories including disease condition, general health status, wellness or life-style, and genotype. For example, a subject's blood glucose levels can relate to the subject's life-style (e.g., diet), the subject's disease condition (e.g., diabetes), or the subject's genotype (e.g., mutations in members of the insulin signaling pathway, such as the insulin receptor).

In some embodiments, the multiwell plates, systems and methods described herein can be used to analyze panels of multiple analytes. In some embodiments, the panels of multiple analytes are analyzed in parallel, e.g., one the same multiwell plate. In some embodiments, a panel of multiple analytes can comprise analyte subpanels, wherein each analyte subpanel can comprise two or more analytes. In some embodiments, the analytes of a subpanel can be analyzed in parallel, e.g., on the same multiwell plate. In some embodiments, assay reagents for the detection of more than one analyte are provided in different wells of a multiwell plate described herein. In some embodiments, assays detecting more than one analyte using more than one assay format are run in parallel, e.g., on the same multiwell plate, in a method described herein. In some embodiments, a subject's analyte levels are determined or communicated to the subject for more than one analyte by a system described herein.

Multiple analytes relating to a subject's disease condition, a subject's general health status, wellness or life-style, and a subject's genotype can be grouped together in an analyte panel or subpanel, or the multiple analytes can be distributed across multiple analyte panels or subpanels.

In some embodiments, multiple analytes relating to a subject's disease condition are grouped together in an analyte panel or subpanel. In some embodiments, multiple analytes relating to a subject's general health status, wellness or life-style are grouped together in an analyte panel or subpanel. In some embodiments, multiple analytes relating to a subject's genotype are grouped together in an analyte panel or subpanel.

In some embodiments, multiple analytes relating to a subject's disease condition are distributed across multiple analyte panels or subpanels. In some embodiments, multiple analytes relating to a subject's general health status, wellness or life-style are distributed across multiple analyte panels or subpanels. In some embodiments, multiple analytes relating to a subject's genotype are distributed across multiple analyte panels or subpanels.

In some embodiments, one or more analytes relating to a subject's disease condition are grouped together with one or more analytes relating to the subject's general health status, wellness or life-style in an analyte panel or subpanel. In some embodiments, one or more analytes relating to a subject's general health status, wellness or life-style are grouped together with one or more analytes relating to the subject's genotype in an analyte panel or subpanel. In some embodiments, one or more analytes relating to a subject's genotype are grouped together with one or more analytes relating to the subject's disease condition in an analyte panel or subpanel. In some embodiments, one or more analytes relating to a subject's disease condition are grouped together in an analyte panel or subpanel with one or more analytes relating to the subject's general health status, wellness or life-style and with one or more analytes relating to the subject's genotype.

In some embodiments, panels comprising analytes of interest comprise a pre-diabetes panel, a cholesterol/lipid analyte panel, a complete metabolic panel, a cardiac marker panel, a fertility panel, a vitamin panel, a nutrition panel, an electrolyte panel, a minerals panel, an endocrinology panel, a thyroid panel, a sepsis cytokine panel, an allergy panel, an autoimmune panel, an oncology panel (e.g., blood oncology panel; e.g., for cancer staging), a blood cell panel, a complete blood cell (CBC) panel, an infectious disease panel, a sexually transmitted disease (STD) panel of analytes, or combinations thereof.

In some embodiments, panels comprising analytes of interest comprise a pre-diabetes panel, a cholesterol/lipid panel, a nutrition panel, a fertility panel, an STD panel, a thyroid panel, an electrolyte panel, a complete metabolic panel, or a CBC panel.

In some embodiments, the pre-diabetes panel comprises hemoglobin A1C, fasting blood glucose, trigycleride, high-sensitivity C-reactive protein (hsCRP), cytostatin C, alanine-aminotransferase (ALT), aspartate aminotransferase (AST), or combinations thereof.

In some embodiments, the cholesterol/lipid analyte panel comprises total cholesterol, triglyceride, high-density lipoprotein (HDL), low-density lipoprotein (LDL), fasting blood glucose, hsCRP, or combinations thereof.

In some embodiments, the complete metabolic panel (CMP) comprises glucose, calcium, albumin, total protein, sodium, potassium, carbon dioxide, chloride, blood urea nitrogen (BUN), creatine, alanine aminotransferase (ALT), alkaline phophatase (ALP), aspartate aminotransferase (AST), bilirubin, or combinations thereof.

In some embodiments, the nutrition panel comprises iron, potassium, sodium, zinc, calcium, vitamin D, magnesium, folate, vitamin B12, or combinations thereof.

In some embodiments, the cardiac marker panel, comprises troponin, heart muscle creatine kinase (CK-MB), lactate dehydrogenase (LDH), aspartate transaminase (AST), myoglobin (Mb), ischemia-modified albumin (IMA), pro-brain natiuretic peptide, glycogen phosphorylase isoenzyme BB, soluble urokinase-type activator receptor (suPAR), or combinations thereof.

In some embodiments, the electrolyte panel can comprise the ion of any salt that dissolves in water. In some embodiments, the electrolyte panel comprises sodium ($Na^+$), potassium ($K^+$), calcium ($CA^{2+}$), magnesium ($Mg^{2+}$), chloride ($Cl^-$), hydrogen phosphate, hydrogen carbonate ($HCO_3^-$), carbon dioxide ($CO_2$), phosphate ($HPO_4^{2-}$, $PO_4^{3-}$), sulfate ($SO_4^{2-}$), an organic acid (lactate, pyruvate, and the like), a proton ($H^+$), hydroxide ($OH^-$), ammonium ($NH_4^+$) or combinations thereof.

In some embodiments, the electrolyte panel comprises chloride, potassium, sodium, carbon dioxide, or combinations thereof.

In some embodiments, the mineral panel comprises potassium (K), phosphorus (P), magnesium (Mg), sulfate (S), sodium (Na), chloride (Cl), iron (Fe), iodine (I), cobalt (Co), zinc (Zn), copper (Cu), calcium (Ca), nickel (Ni), selenium (Se), boron (B), fluoride (F), silicon (Si), chromium (Cr), manganese (Mn), or combinations thereof.

In some embodiments, the endocrine panel comprises an endocrine organ or a secreted hormone subpanel. In some embodiments, the endocrine organ or secreted hormone subpanel comprises a hypothalamus subsubpanel, a thyroid subsubpanel, a pineal gland subsubpanel, a pituitary gland subsubpanel, or combinations thereof. In some embodiments, the hypothalamus subsubpanel comprises thyrotropin-releasing hormone (TRH), dopamine or prolactin-inhibiting hormone (DA or PIH), growth hormone-releasing hormone (GHRH), somatostatin or growth hormone-inhibiting hormone (SS, GHIH, or SRIF), gonadotropin-releasing hormone (GnRH or LHRH), corticotrophin-releasing hormone (CRH or CRF), vasopressin or antidiuretic hormone (ADH, AVP, or VP), or combinations thereof. In some embodiments, the pineal body (epiphysis) subsubpanel comprises melatonin. In some embodiments, the pituitary gland (hypophysis) subsubpanel comprises growth hormone, thyroid-stimulating hormone or thyrotropin (TSH), adrenocorticotropic hormone or corticotrophin (ACTH), β-endorphin, follicle-stimulating hormone (FSH), luteinizing hormone (LH), prolactin (PRL), melanocyte-stimulating hormone (MSH), oxytocin, vasopressin or antidiuretic hormone (ADH or AVP), or combinations thereof. In some embodiments, the thyroid subsubpanel comprises triiodothyronine (T3), thyroxine or tetraiodothyronine (T4), calcitonin, or combinations thereof.

In some embodiments, the endocrine panel comprises a digestive system subpanel. In some embodiments, the digestive system subpanel comprises a stomach subsubpanel, a duodenum subpanel, a liver subpanel, a pancreas subpanel, or combinations thereof. In some embodiments, the stomach subsubpanel comprises gastrin, ghrelin, neuropeptide Y (NPY), somatostatin, histamine, endothelin, or combinations thereof. In some embodiments, the duodenum subsubpanel comprises secretin or cholecystokinin. In some embodiments, the liver subsubpanel comprises insulin-like growth factor or somatomedin (IGF), angiotensinogen, angiotensin, thrombopoietin, hepcidin, or combinations thereof. In some embodiments, the pancreas subsubpanel comprises, insulin, glucagon, somatostatin, pancreatic polypeptide, or combinations thereof.

In some embodiments, the endocrine panel comprises a kidney subpanel. In some embodiments, the kidney subpanel comprises rennin, erythropoietin (EPO), calcitriol (1,25-dihydroxyvitamin $D_3$), thrombopoietin, or combinations thereof.

In some embodiments, the endocrine panel comprises an adrenal glands subpanel. In some embodiments, the adrenal glands subpanel comprises an adrenal cortex, an adrenal medulla subsubpanel, or both. In some embodiments, the adrenal cortex subsubpanel comprises a glucocorticoid (e.g., cortisol), a mineralocorticoid (e.g., aldosterone), an androgen (e.g., DHEA, testosterone), or combinations thereof. In some embodiments, the adrenal medulla subsubpanel comprises adrenaline (epinephrine), noradrenaline (norepinephrine), dopamine, enkephalin, or combinations thereof.

In some embodiments, the endocrine panel comprises a reproductive system subpanel. In some embodiments, the reproductive system subpanel comprises a testes subsubpanel, an ovarian follicle and corpus luteum subsubpanel, a placenta (e.g., when pregnant) subsubpanel, a uterus subsubpanel, or combinations thereof. In some embodiments, the testes subsubpanel comprises an androgen (e.g., testosterone), estradiol, inhibin, or combinations thereof. In some embodiments, the ovarian follicle and corpus luteum subsubpanel comprises progesterone, androstenedione, an estrogen (e.g., estradiol), inhibin, or combinations thereof. In some embodiments, the placenta subsubpanel comprises progesterone, estrogen (e.g., estriol (oestriol, E3)), human chorionic gonadotropin (HCG), human placental lactogen, or inhibin, or combinations thereof. In some embodiments, the uterus subsubpanel comprises prolactin, relaxin, or combinations thereof.

In some embodiments, the endocrine panel comprises a skin subsubpanel, a parathyroid subsbupanel, or both. In some embodiments, the skin subsubpanel comprises calcidiol (25-hydroxyvitamin $D_3$). In some embodiments, the parathyroid subsubpanel comprises parathyroid hormone.

In some embodiments, the endocrine panel comprises a subpanel organized according to a hormone's target organ, e.g., in a human. In some embodiments, the target organ subpanel comprises as heart subsubpanel, a bone marrow subsubpanel, a skeletal muscle subsubpanel, an adipose tissue subsubpanel, or combinations thereof. In some embodiments, the heart subsubpanel comprises atrial-natiuretic peptide (ANP), brain natiuretic peptide (BNP), or both. In some embodiments, the bone marrow subsubpanel comprises thrombopoietin. In some embodiments, the skeletal muscle (myokine) subsubpanel comprises myostatin, leukemia inhibitory factor (LIF), interleukine 1 (IL-1), IL-1 receptor antagonist (IL-Ira), interleukine 6 (IL-6), interleukine 7 (IL-7), interleukine 10 (IL-10), bone-derived neurotrophic factor (BDNF), IGF-1, fibroblast growth factor 2 (FGF-2), follistatin-related protein 1 (FSTL-1), irisine, or combinations thereof. In some embodiments, the adipose tissue subsubpanel comprises leptin an estrogen (e.g., estrone (oestrone, E1)), or both.

In some embodiments, the endocrine panel comprises a functional subpanel organized according to a regulatory relationship between panel members (e.g., a feedback loop, e.g., mediated via the hypothalamus or pituitary). In some embodiments, the functional subpanel comprises TRH, TSH, and T3/T4. In some embodiments, the functional subpanel comprises GnRH, LH/FSH, and a sex hormone. In some embodiments, the functional subpanel comprises CRH, ACTH, and cortisol. In some embodiments, the functional subpanel comprises renin, angiotensin, and aldosterone. In some embodiments, the functional subpanel comprises leptin and insulin.

In some embodiments, the fertility panel comprises human chorionic gonadotropin (HCG), follicle-stimulating hormone (FSH), estradiol, Anti-Mullerian hormone (AMH), progesterone, prolactine (PRL), or combinations thereof.

In some embodiments, the vitamin panel comprises, vitamin A (retinol, retinal, carotenoids, e.g., $\beta$-carotene), vitamin $B_1$ (thiamine), vitamin $B_2$ (riboflavin), vitamin $B_3$ (niacin, niacinamide), vitamin $B_5$ (pantothenic acid), vitamin $B_6$ (pyridoxine, pyridoxamine, pyridoxal), vitamin $B_7$ (biotin), vitamin $B_9$ (folic acid, folinic acid), vitamin $B_{12}$ (cyanocobalamin, hydroxocobalamin, methylcobalamin), vitamin C (ascorbic acid), vitamin D (cholecalciferol ($D_3$), ergocalciferol ($D_2$)), vitamin E (tocopherols, tocotrienols), vitamin K (phylloquinone, menaquinones), or combinations thereof.

In some embodiments, the thyroid panel comprises thyroid-stimulating hormone (TSH), triiodothyronine (T3), thyroxine (T4), or combinations thereof.

In some embodiments, the infectious disease panel comprises an analyte related to hepatitis (e.g., A, B, C, D, E, F, or G; e.g., hepatitis B surface antigen, hepatitis B virus core antigen, hepatitis nucleic acids; hepatitis C virus encoded antigen), herpes (e.g., HSV-1, HSV-2), influenza (e.g., A, B), respiratory syncytial virus (RSV), human immunodeficiency virus (HIV-1, HIV-2), human T-lymphotrophic virus (e.g., HTLV-1, HTLV-2), *Treponema* palladium (Syphilis), *Chlamydia trachomatis* (*Chlamydia*), *Neisseria gonorrhoeae* (Gonorrhea), *Trypanosoma cruzi* (Chagas), west nile virus (WNV), cytomegalo virus (CMV), or combinations thereof.

In some embodiments, the STD panel comprises *Chlamydia trachomatis, Neisseria gonorrhoeae, Treponema* palladium, HSV-1, HSV-2, HIV, hepatitis B, hepatitis C, or combinations thereof.

In some embodiments, the sepsis cytokine panel comprises tumor necrosis factor alpha (TNF$\alpha$), interleukin 1 (e.g., IL-1$\beta$), interleukin 2 (IL-2), interleukin 6 (IL-6), interleukin 8 (IL-8), interleukin 10 (IL-10), or combinations thereof.

In some embodiments, the allergy panel comprises IgE.

In some embodiments, the autoimmune panel comprises an autoantibody, rheumatoid factor (RF), C-reactive protein (CRP, e.g., hsCRP), a complement protein, or combinations thereof. In some embodiments, the autoimmune panel comprises an erythrocyte sedimentation rate (ESR). In some embodiments, the autoantibody comprises an antinuclear antibody (ANA). In some embodiments, the antinuclear antibody comprises an anti-Ro(SSA) antibody, an anti-La (SSB) antibody, an anti-Smith (Sm) antibody, an antinuclear ribonucleoprotein (nRNP) antibody, an anti-topoisomerase 1 (Scl-70) antibody, an anti-double-stranded DNA (dsDNA) antibody, an anti-histone antibody, an antibody to a nuclear pore complex, an anti-centromere antibody, an anti-sp100 nuclear antigen antibody, an anti-histidine-tRNA ligase (Jo1) antibody, an anti-histone antibody, an anti-nucleoprotein 62 (p62) antibody, an anti-glycoprotein-210 (nucleoporin 210 kDa) antibody, or combinations thereof. In some embodiments, the autoantibody comprises an anti-transglutaminase (e.g., anti-tissue transglutaminase (tTG), anti-epidermal transglutaminase (eTG) antibody). In some embodiments, the autoantibody comprises an anti-ganglioside antibody (e.g., ganglioside GQTB, GD3 or GMT). In some embodiments, the autoantibody comprises an anti-actin antibody. In some embodiments, the autoantibody comprises an anti-cyclic citrullinated peptide (anti-CCP) antibody. In some embodiments, the autoantibody comprises a liver kidney microsomal type 1 antibody. In some embodiments, the autoantibody comprises a lupus anticoagulant or anti-thrombin antibody. In some embodiments, the autoantibody comprises an antiphospholipid antibody. In some embodiments, the autoantibody comprises an anti-neutrophil cytoplasmic antibody (e.g., c-ANCA (directed to proteins in neutrophil cytoplasm) or p-ANCA (neutrophil perinuclear)). In some embodiments, the autoantibody comprises an anti-smooth muscle antibody. In some embodiments, the autoantibody comprises an anti-mitochondrial antibody. In some embodiments, the autoantibody comprises an anti-signal recognition particle (SRP) antibody. In some embodiments, the autoantibody comprises an anti-nicotinic acetylcholine receptor (AChR) antibody. In some embodiments, the autoantibody comprises an anti-muscle-specific kinase (MUSK) antibody. In some embodiments, the autoantibody comprises an anti-voltage-gated calcium channel (P/Q-type; VGCC) antibody. In some embodiments, the autoantibody comprises an anti-thyroid autoantibody (e.g., anti-thryroid peroxidase (TPO) antibody, anti-thyroglobulin, anti-thyrotropin receptor (TSH receptor) antibody). In some embodiments, the autoantibody comprises an anti-neuronal nuclear protein (e.g., anti-Hu (ANNA-1), anti-Ri (ANNA-2)) antibody. In some embodiments, the autoantibody comprises an anti-Yo (cerebellar Purkinje cell) antibody. In some embodiments, the autoantibody comprises an anti-Ma antibody. In some embodiments, the autoantibody comprises an anti-glutamate receptor (anti-Tr) antibody. In some embodiments, the autoantibody comprises an anti-amphiphysin antibody. In some embodiments, the autoantibody comprises an anti-glutamate decarboxylase (GAD) antibody. In some embodiments, the autoantibody comprises an anti-voltage gated potassium channel (VGKC) antibody. In some embodiments, the autoantibody comprises a collapsing response mediator protein 5 (CRMP-5) antibody. In some embodiments, the autoantibody comprises an anti-N-methyl-D-aspartate receptor (NMDAr) antibody. In some embodiments, the autoantibody comprises an aquaporin-4 (NMO antibody).

In some embodiments, the oncology panel (e.g., blood oncology panel) comprises an anaplastic lymphoma kinase (ALK) mutation, alpha-fetoprotein (AFP), $\beta$2-microglobulin (B2M), beta-human chorionic gonadotropin (beta-hCG), BRCA1, BRCA2, BCR-ABL, a BRAF mutation (e.g., V600 mutations, V600E), carcinoma antigen 15-3 (CA15-3), cancer antigen 27-29 (CA27-29), carbohydrate antigen 19-9 (CA19-9), cancer antigen 125 (CA-125), calcitonin, carcinoembryonic antigen (CEA), CD20, chromogranin A (CgA), chromosomes 3, 7, 17, and 9p21, circulating tumor cells of epithelial origin (CTC), cytokeratin fragment 21-1, an EGFR mutation, KIT, estrogen receptor (ER), progesterone receptor (PR), fibrin/fibrinogen, human epididymis protein 4 (HE4), immunoglobulins (e.g., IgG, IgM, IgA); free immunoglobulin light chains (e.g., Bence Jones protein in urine), a KRAS mutation, lactate dehydrogenase (LDH), neuron-specific enolase (NSE), nuclear matrix protein 22 (NMP22), prostatic acid phosphatase (PAP), programmed death ligand 1 (PD-L1), prostate-specific antigen (PSA), S-100, soluble mesothelin-related peptides (SMRP), thyroglobulin, uroki-nase plasminogen activator (uPA), plasminogen activator inhibitor (PAI-1), or combinations thereof. In some embodiments, the blood oncology panel (e.g., ovarian cancer panel, 5-protein signature) comprises CA-125, β2-microglobulin (B2M), ApoA1, transerytin (TT) and transferrin (TF).

In some embodiments, the blood cell panel comprises red blood cells (RBC; e.g., RBC count), platelets (e.g., platelet count), or white blood cells (WBC; e.g., WBC count). In some embodiments, the WBC comprises the totality of WBCs in a blood sample (e.g., cluster of differentiation 45 (CD45)-positive cells, e.g., CD45RA-isotype or CD45RO-isotype; e.g., total WBC count). In some embodiments, the WBC comprises a T-cell (e.g., cluster of differentiation 3 (CD3)-positive cells), a B-cell (e.g., cluster of differentiation 19 (CD19)-positive cells), a natural killer (NK) cell (e.g., CD3-negative and cluster of differentiation 16 (CD16) and cluster of differentiation 56 (CD56)-positive cells), or combinations thereof. In some embodiments, the T-cell comprises a T-helper cell (e.g., CD4-positive cells) or a cytotoxic T-cell (e.g., CD8-positive cells). In some embodiments, T-helper cells or cytotoxic T-cells can be further classified into naive cells (e.g., CD4RA$^+$ or CD8 RA$^+$), or memory cells (e.g., CD4RO$^+$ or CD8RO$^+$). In some embodiments, the blood cell panel comprises a circulating tumor cell (CTC; e.g., CTC count). In some embodiments, the CTC comprises a traditional CTC (e.g., CD45− negative, creatin kinase (CK)-positive cell with intact nucleus), a cytokeratin negative (CK$^-$) CTC (e.g., CD45-negative cell with cancer cell-like morphology), a small CTC (e.g., a CD45-negative cell with a size and morphology similar to an average WBC), or a CTC cluster (e.g., two or more CTCs bound together, e.g., cluster of traditional, CK-negative or small CTCs). In some embodiments, the blood cell panel comprises CD45 (e.g., CD45RA or CD45RO, or both), CD3, CD16, CD56, CD4, CD8, CK, cell morphology (e.g., cell size or shape, tumor cell-like or WBC-like phenotype or appearance, intact or apoptotic nucleus, and the like), or combinations thereof.

In some embodiments, the complete blood cell (CBC) panel comprises white blood cell count (WBC), white blood cell differential (DIFF), absolute neutrophil count, % neutrophils (Neu, PMN, polys), absolute lymphocyte count, % lymphocytes (Lymph), absolute monocyte count, % monocytes (Mono), absolute eosinophil count, % eosinophils (EOS), absolute basophil count, % basophils (BASO), red blood count (RBC), red blood cell distribution (RDW), hemoglobin (Hb), hematocrit (Hct), mean corpuscular volume (MCV), mean corpuscular hemoglobin (MCH), mean corpuscular hemoglobin concentration (MCHC), platelet count (PIT), mean platelet volume (MPV), or combinations thereof.

Analytes, or clinical parameters, that can be analyzed using the multiwell plates, systems, or methods described therein can comprise analytes present at a wide range of different concentrations in a sample (e.g., a blood sample or urine sample). Analytes can include high-abundance analytes, medium-abundance analytes, and low-abundance analytes. In some embodiments, high-abundance analytes comprise analytes present in a sample at concentrations of >100 μM, e.g., >500 μM, >1 mM, >2 mM, >3 mM, >4 mM, >5 mM, >6 mM, >7 mM, >8 mM, >9 mM, >10 mM, >15 mM, >20 mM, >25 mM, >50 mM, >75 mM, >100 mM, >125 mM, >150 mM, or >200 mM. In some embodiments, medium abundance analytes comprise analytes present in a sample at concentrations between 100 nM and 100 μM (e.g., between 100 nM and 1 μM, between 1 μM and 10 μM, or between 10 μM and 100 μM). In some embodiments, low abundance analytes comprise analytes present in a sample at concentrations of <100 nM, such as <10 nM, <1 nM, <100 pM, <10 pM, or <1 pM.

In some embodiments, analyte concentrations can vary in different patients, e.g., due to genetic, environmental, or health or wellness status differences. In some embodiments, analyte concentrations can vary between two or more patients by more than 10%, more than 20%, more than 30%, more than 40%, more than 50%, more than 60%, more than 70%, more than 80%, more than 90%, more than 100%, more than 3-fold, more than 4-fold, more than 5-fold, more than 6-fold, more than 7-fold, more than 8-fold, more than 9-fold, more than 10-fold, more than 15-fold, more than 20-fold, more than 25-fold, more than 50-fold, more than 100-fold, more than 300-fold, or more than 1,000-fold.

In some embodiments, analyte concentrations can vary in the same patient over time, e.g., due to changing environmental, or health or wellness status differences. In some embodiments, analyte concentrations can vary between two or more patients by more than 10%, more than 20%, more than 30%, more than 40%, more than 50%, more than 60%, more than 70%, more than 80%, more than 90%, more than 100%, more than 3-fold, more than 4-fold, more than 5-fold, more than 6-fold, more than 7-fold, more than 8-fold, more than 9-fold, more than 10-fold, more than 15-fold, more than 20-fold, more than 25-fold, more than 50-fold, more than 100-fold, more than 300-fold, or more than 1,000-fold.

5.10 Uses

The systems and methods described herein can provide ready access to comprehensive diagnostic information for consumers, physicians and scientific researchers. By facilitating access to diagnostic testing the systems and methods described herein encourage consumers to repeatedly and frequently test health and wellness related analytes, thereby helping consumers and their physicians to make informed choices, e.g., regarding possible medical treatments options or lifestyle changes. Frequent diagnostic testing can also provide rapid feedback to consumers as to possible beneficial or harmful effects of new medical treatment regimens or of changes in their daily routines (e.g., diet, exercise) and can allow physicians to respond faster to changes in a patient's health condition, e.g., by adjusting medication.

For example, the systems and methods described herein can be useful to consumers interested in monitoring personal healthcare information. For example, a consumer may be interested in tracking the status of a chronic disease condition (e.g., diabetes or metabolic syndrome) or monitor the early effects of a new medical treatment. Such a consumer may be interested in testing a blood sample on a regular basis for a panel of metabolic analytes. The diagnostic results obtained using the systems and methods described herein can inform the consumer's decision on whether or when a doctor should be consulted.

Also, the systems and methods described herein can be useful to a consumer interested in general wellness related information. For example, a consumer may be interested in monitoring the effects of certain lifestyle choices on the consumer's general wellbeing (e.g., new diet, smoking cessation, new job, vacation, new exercise regimen, meditation, new partner). Such a consumer may be interested in testing a blood sample on a regular basis for an analyte panel including, e.g., stress hormones and other markers. The diagnostic results obtained using the systems and methods described herein can help guide the consumer towards steady improvements in the consumer's general wellbeing.

The systems and methods described herein can also be useful to pharmaceutical companies, and medical research organizations generally, e.g., in the pursuit of new diagnostic or prognostic markers, e.g., to facilitate patient selection for personalized treatment regimens.

The recitation of a listing of elements in any definition of a variable herein includes definitions of that variable as any single element or combination (or subcombination) of listed elements. The recitation of an embodiment herein includes that embodiment as any single embodiment or in combination with any other embodiments or portions thereof.

All patents and publications mentioned in this specification are herein incorporated by reference to the same extent as if each independent patent and publication was specifically and individually indicated to be incorporated by reference.

The following examples are provided by way of illustration, not limitation.

Example 1

Glucose Assay (Fluorescence)

This example illustrates results of homogeneous fluorescence-based glucose assays performed in a Truvian Sciences multiwell plate and system.

The glucose assay was performed in a rectangular Truvian multiwell plate component ("chip") with 24 wells in a 6×4 arrangement (also referred to as a "cartridge") and read on a Truvian assay measurement unit (AMU). The optics module of the AMU was rotated 180 deg to allow for bottom reads of a sample on a cartridge. An inverted macro confocal imaging system allowed for fluorescence reads in an assay well without potential optical interference from the fluid meniscus or bubbles on the surface of the fluid. An inverted system moved the cartridge to the top of the AMU which allowed for pipette access directly to the cartridge and room for a heater.

The AMU further included an absorbance module (see also FIG. 2). The absorbance module consisted of a strobing xenon arc lamp light source, fiber optic cables, a mount for the focusing lenses, and a spectrometer. Light source and measurement spectral bandwidth of measurements were optimized to cover a range from 350 nm to 800 nm.

The AMU was integrated with an automated pipettor (Tecan, Mannedorf, Switzerland). The pipettor was found to have fluid transfer precision of 2-3% CVs for volumes less than 10 μl, and 1-2% CVs for volumes greater than 10 μl with a 200 μl pipette tip.

A glucose assay was performed by adapting a commercially available fluorometric glucose assay kit (Cell Biolabs, Inc., San Diego, CA; cat no. STA-681) to a Truvian multiwell plate (cartridge) and system described herein. In brief, 10× assay buffer, glucose peroxidase, horseradish peroxidase (HRP), and fluorometric probe were thawed; lx assay buffer was prepared by diluting the 10× assay buffer 1:10 with deionized water. The glucose standards were then prepared from a 40 mM glucose solution by diluting the stock glucose standard 1:10 in 1× assay buffer. A serial dilution from the 40 mM glucose solution was utilized to generate a series of glucose standards corresponding to 1.8 mg/dL, 0.9 mg/dL, 0.45 mg/dL, 0.225 mg/dL, 0.113 mg/dL, 0.056 mg/dL, 0.028 mg/dL, 0.014 mg/dL, and 0 mg/dL glucose. Two different donor plasma samples were thawed and diluted 1:400 in 1× assay buffer. Plasma was isolated from whole blood samples from these two donors collected under an institutional review board (IRB) approved protocol at the Scripps Normal Donor Blood Bank, and was stored at −80° C. until used. A reaction mix was created which included 1:50 glucose oxidase, 1:500 HRP, and 1:100 fluorometric probe all diluted in 1× assay buffer. Cartridges were then prepared. To each well, L of reaction mix and 10 μL of diluted patient sample was added. The cartridge was placed on a heater shaker (37° C.) for 60 minutes then read on the Assay Measurement Unit (AMU). The AMU read the bulk fluorescence in each individual well and image analysis software developed by Truvian Sciences was used to analyze the images and reported back fluorescent units. The glucose standard curve data was utilized to calculate the glucose values for the two normal donor samples. 100 μL of non-diluted plasma from each donor was run in parallel on a Piccolo Xpress chemistry analyzer (Abaxis, Union City, CA) as a comparator reading, using the manufacturer's instructions. Piccolo Xpress is a commercially available point-of-care clinical chemistry analyzer that is approved for home use by the United States Food and Drug Administration (CLIA-waived).

FIG. 17 shows a graph illustrating an exemplary glucose standard curve obtained using a Truvian cartridge component. The standard curves was found to be linear in a concentration range from 0 mg/dL to 1.8 mg/dL glucose.

Table 1 shows comparative results of exemplary glucose concentration determinations in two donor blood samples obtained using a Truvian cartridge component and AMU, or an FDA-approved comparator device ("Piccolo"). Glucose assay results obtained with the Truvian Sciences system were found to be within 10% (Table 1) of comparator readings.

TABLE 1

| Glucose Levels in Donor Samples (mg/dL glucose) | | | |
|---|---|---|---|
| Sample | Truvian | Piccolo | % Error |
| 1 | 73.9 mg/dL | 73 mg/dL | −1% |
| 2 | 115.0 mg/dL | 107 mg/dL | −7% |

In another study, frozen Healthy Donor (HD) plasma samples and horseradish peroxidase (HRP) stock (10 U/mL resuspended in 50 mM sodium phosphate buffer, pH 7.4, Thermo Fisher Scientific, Waltham, MA) were thawed on ice. Glucose reagent R1 (10×, Cliniqa Corp., San Marcos, CA), multi-analyte standard containing 300 mg/dL glucose and 300 mg/dL triglyceride (Cliniqa Corp.), and assayed control serum level 1 and 2 (Cliniqa Corp.) were set on ice until use. Amplex red stock (10 mM prepared in DMSO, Thermo Fisher Scientific) was prepared fresh and set at room temperature until use. Truvian fluorescent reagent B (10×) was prepared by diluting 10 mM amplex red stock to 1 mM and 10 U/mL HRP stock to 2 U/mL in 1×PBS, pH 7.4 (Thermo Fisher Scientific). 2× Reaction mix was then prepared by diluting 10× glucose reagent Ri and 10× Truvian fluorescent reagent B to 2× in 1×PBS, pH 7.4. Following reagent preparation, multi-analyte standard was diluted in 1×PBS, pH 7.4 to generate a series of glucose standards corresponding to 70 mg/dL, 35 mg/dL, 17.5 mg/dL, 8.75 mg/dL, 4.375 mg/dL, 2.19 mg/dL, 1.1 mg/dL, and 0 (1×PBS blank). Assayed serum controls and HD plasma samples were each diluted 1:10 in 1×PBS, pH 7.4. All standards, control serum samples and HD plasma samples were then further diluted 1:75 in 1×PBS, pH 7.4 for ease of sample loading. To perform the assay, 15.2 μL of each diluted standard, blank, assayed serum controls and HD plasma samples were loaded into a black clear bottom 384-well high content imaging microplate (Corning Inc., Fremont, CA) in triplicates. Then 15 μL of 2× reaction mix were added to each well using a multi-channel micropipette. The plate was then immediately placed into the SpectraMax M2 plate reader (Molecular Devices) that was pre-set and equilibrated at 37° C., mixed using the "shake" function on the Spec-traMax instrument for 30 seconds, and data collected every minute for 20 minutes using the kinetic fluorescence reading mode with wavelength settings of 540 nm for excitation, 590 nm for emission, and 570 nm for cut-off. Glucose concentrations (mg/dL) for assayed serum controls and HD plasma samples were then calculated based on a glucose standard curve using Microsoft Excel. Each assayed serum control and HD plasma sample was also run on the Piccolo Xpress as a comparator.

FIG. 18 shows a graph illustrating an exemplary glucose standard curve obtained using the Truvian assay. The standard curves was found to be linear in a concentration range from 5.6 mg/dL to 720 mg/dL glucose.

Table 2 shows averaged comparative results of 5-7 exemplary glucose concentration determinations in donor blood samples using the Truvian assay, or an FDA-approved comparator device ("Piccolo"). Glucose assay results obtained with the Truvian Sciences system were found to be within 15% (Table 2) of comparator readings.

TABLE 2

| Glucose Levels in Donor Samples (mg/dL glucose) | | | |
| --- | --- | --- | --- |
| Sample | Piccolo | Truvian | % Error |
| 79 | 89 | 80 | −10% |
| 81 | 110 | 94 | −14% |
| 85 | 155 | 149 | −4% |
| 87 | 87 | 80 | −8% |
| L1 (100 mg/dL) | 96 | 103 | 8% |
| L2 (250 mg/dL) | 219 | 253 | 15% |

L1 = low glucose control (100 mg/dL);
L2 = high glucose control (250 mg/dL)

Glucose concentration results for donor samples were found to be highly reproducible. FIG. 19 shows a graph illustrating results of 12 glucose assays for each of four donor samples (HD079, HD081, HD085, and HD087) and a low glucose control (CNT L1, 100 mg/dL glucose) and a high glucose control (CNT L2, 250 mg/dL glucose). Intra-assay precision was determined to be <10% CV and inter-assay precision was determined to be <12% CV. Blood samples were typically diluted 1:1,500-1:3,00-fold in the final glucose assay (30 μl volume), requiring 10 nl-20 nl neat plasma equivalents per assay.

A modified glucose assay protocol was developed to provide glucose assay reagents in a dried form. In brief, glucose reagent R1 (Cliniqa Corp.) was dried down in black clear bottom 384-well high content imaging microplate (Corning, Inc.) in the presence of a drying buffer. The microplate with dried reagents was then tested together with either Cliniqa glucose assay reagent (normal assay control) or with Cliniqa glucose assay reagent mixed with Truvian's DRT buffer as a "wet" drying buffer control. 2× reaction mix with Cliniqa glucose assay reagent only (normal assay control) was prepared by adding 200 μL of Cliniqa glucose reagent R1, 5 μL HRP stock, 30 μL 100 μM amplex ultrared (Thermo Fisher Scientific) to 1765 μL of 2×PBS at pH 7.4. 2× reaction mix with Cliniqa glucose assay reagent and drying buffer was prepared by adding 200 μL glucose reagent R1, 5 μL HRP stock, 30 μL 100 μM amplex ultrared and 100 μL of 2×DRT buffer to 765 μL 2×PBS, pH 7.4. Following reagent preparation, a series of glucose standards corresponding to 270 mg/dL, 135 mg/dL, 67.5 mg/dL, and 0 (1×PBS blank) was generated by diluting a 540 mg/dL stock in a 2-fold dilution series in 1×PBS. To perform the assay, 10 μL of water was added into wells with dried down reagents, 10 μL of 2× reaction mix with glucose assay reagent only was added into fresh (empty) wells, or 10 μL of 2× reaction mix with glucose assay reagent and drying buffer was added into fresh (empty) wells. Subsequently, 10 μL of glucose standards or blank was added into each well. The plate was then incubated for 30 minutes at 37° C. with shaking, after which 5 μL of a stop solution was added into each well and incubated for 1 minute with shaking. Data was collected on a SpectraMax M2 instrument with wavelength settings of 488 nm for excitation, 595 nm for emission, and 570 nm for cut-off. Raw relative fluorescent unit (RFU) readings were plotted in a graph, see, e.g., FIG. 20.

Glucose assays were performed in a mix-and-read format so that sample addition to a well containing dried assay reagents started the assay reaction. FIG. 20 shows a graph illustrating results of an exemplary glucose standard curve as determined using a dried reagents protocol. Table 3 shows results of comparative assays determining glucose levels in two control samples (L1 Control=100 mg/dL; L2 Control=250 mg/dL) and one blood donor sample (HD081) using a dried reagent fluorescence assay protocol (DR) besides the Piccolo comparator assay.

TABLE 3

| Glucose Levels in Donor and Control Samples Piccolo vs DR | | | |
| --- | --- | --- | --- |
| Sample | Piccolo | DR | % Error |
| L1 Control | 93 | 100.5 | 8% |
| L2 Control | 216 | 252.5 | 17% |
| HD081 | 110 | 115.9 | 5% |

This example demonstrates that adaptation of a fluorescence based glucose assay to the Truvian platform (cartridge and AMU) resulted in the collection of precise and accurate data from donor blood samples as compared to data generated with a CLIA-waived comparator system. The glucose assay was shown to be amenable to conversion into a dried reagent format.

Example 2

Cholesterol Assay (Fluorescence)

This example illustrates results of homogeneous fluorescence-based cholesterol assays performed using a Truvian Sciences multiwell plate and system.

The cholesterol assay was performed using the Truvian cartridge component and AMU described in Example 1. In brief, cholesterol standard, 1× assay buffer, cholesterol enzyme mix, cholesterol esterase and cholesterol probe all purchased from Sigma Aldrich (St. Louis, MO; Cholesterol Quantification Kit) were thawed. The cholesterol standards were then prepared from a 50 ng/μL cholesterol solution by diluting the stock cholesterol standard 1:80 in 1× assay buffer. A serial dilution from the 50 ng/μL cholesterol solution was utilized to generate a series of cholesterol standards corresponding to 1 mg/dL, 0.5 mg/dL, 0.25 mg/dL, 0.125 mg/dL, 0.0625 mg/dL, and 0 mg/mL cholesterol. Two different donor plasma samples were thawed and diluted 1:400 in 1× assay buffer. Neat sample from these same two donor samples were used for HDL precipitation. 100 μL of precipitation buffer was added to 100 μL of plasma sample. This solution was mixed and allowed to incubate for 10 minutes at room temperate. Following incubation, the precipitated sample was centrifuged at 2,000×g for 10 minutes. Supernatant was transferred to a fresh tube and was processed the same as the neat HD sample for cholesterol. 100 μL of non-diluted plasma from each donor was run on a Piccolo Xpress as a comparator reading. Plasma was isolated from whole blood samples from these two donors collected under IRB at the Scripps Normal Donor Blood Bank and was stored at −80° C. until used. A reaction mix was created which included 1:25 Cholesterol Enzyme Mix, 1:25 Cholesterol Esterase, and 1:25 cholesterol probe all diluted in 1× assay buffer. Cartridges were then prepared. To each well, 10 μL of reaction mix and 10 μL of diluted patient sample was added. The cartridge was placed on a heater shaker (37° C.) for 30 minutes then read on the Truvian Assay Measurement Unit (AMU). The AMU read the bulk fluorescence in each individual well and Truvian's image analysis software analyzed the images and reported back fluorescent units. The cholesterol standard curve data was utilized to calculate the Truvian cholesterol values for the two normal donor samples.

FIG. 21 shows a graph illustrating an exemplary glucose standard curve obtained using a 24-well (6×4) Truvian cartridge. Standard curves were found to be linear in a concentration range from 25 mg/dL to 400 mg/dL glucose.

Table 4 shows comparative results of exemplary cholesterol and HDL concentration determinations in two donor blood samples obtained using a Truvian cartridge and AMU, or a CLIA-waived comparator device ("Piccolo"). Generally, glucose assay results obtained with the Truvian system were found to fall within 10% of comparator readings.

TABLE 4

| Cholesterol and HDL Levels in Donor Samples (mg/dL glucose) | | | |
| --- | --- | --- | --- |
| Samples | Truvian | Piccolo | % Error |
| 1 - Chol | 237 | 236 | 0% |
| 1- HDL | 47 | 51 | −8% |
| 2 - Chol | 176 | 170 | 3% |
| 2- HDL | 66 | 66 | −1% |

A modified cholesterol assay protocol was developed to provide glucose assay reagents in a dried form. Cholesterol standard, Cholesterol Enzyme Mix, Cholesterol Esterase and Cholesterol probe (Sigma Aldrich; Cholesterol Quantification Kit) were thawed. Reaction mix for Truvian cartridge chips was created, which included 1:25 Cholesterol Enzyme Mix, 1:25 Cholesterol Esterase, and 1:25 cholesterol probe all diluted in 1× drying buffer. 10 μL of reaction mix was loaded into each well of the Truvian cartridge chip and dried. Dried chips were then stored at room temperature in an airtight container with desiccant until use. The cholesterol standards were prepared from a 50 ng/μL cholesterol solution by diluting the stock cholesterol standard 1:80 in 1× Assay Buffer. A serial dilution from the 50 ng/μL cholesterol solution was utilized to generate a series of cholesterol standards corresponding to 1.5 mg/dL, 0.75 mg/dL, 0.375 mg/dL, 0.1875 mg/dL, 0.09375 mg/dL, 0.046875 mg/dL and 0 mg/dL. Two different donor plasma samples were thawed and diluted 1:400 in 1× Assay Buffer. Neat sample from these same two donor samples were used for HDL precipitation. 100 μL of precipitation buffer was added to 100 μL of plasma sample. This solution was mixed and allowed to incubate for 10 minutes at room temperate. Following incubation, the precipitated sample was centrifuged at 2,000×g for 10 minutes. Supernatant was transferred to a fresh tube and was processed the same as the neat HD sample for cholesterol. 100 μL of non-diluted plasma from each donor was run on the Piccolo Xpress as a comparator reading. Plasma was isolated from whole blood samples from these two donors collected under IRB at the Scripps Normal Donor Blood Bank and was stored at −80° C. until use. To each well, 10 μL of PBS was added to reconstitute the dried reagents. Following reaction mix reconstitution, 10 μL of diluted patient sample was added. The cartridge was placed on a heater shaker (37° C.) for 30 minutes then read on the Truvian Assay Measurement Unit (AMU). The AMU read the bulk fluorescence in each individual well and Truvian's image analysis software analyzed the images and reported back fluorescent units. The cholesterol standard curve data was utilized to calculate the Truvian cholesterol values for the two normal donor samples.

FIG. 22 shows a graph illustrating an exemplary cholesterol standard curve obtained using dried assay reagents in a Truvian cartridge. The Standard curves were found to be linear in a concentration range from 25 mg/dL to 400 mg/dL glucose.

Table 5 shows results for exemplary cholesterol level determinations in two donor samples using dried down or wet cholesterol assay reagents. Dry reagent results were found to fall within 10% of wet reagents results.

TABLE 5

| Cholesterol Levels in Donor Samples Determined Using Dried Down and Wet Assay Reagents | | | |
| --- | --- | --- | --- |
| Cholesterol | Wet mg/dL | 1X Dry mg/dL | % Diff |
| 1 - Chol | 300 | 322 | 7% |
| 1 - HDL | 19 | 19 | 2% |
| 2 - Chol | 225 | 237 | 5% |
| 2- HDL | 54 | 54 | 1% |

This example demonstrates that adaptation of a fluorescence based cholesterol assay to the Truvian platform resulted in the collection of precise and accurate data across a wide dynamic range. Blood glucose levels determined in donor blood samples using a Truvian cartridge compared well to levels obtained with a CLIA-waived comparator system. The fluorescence based cholesterol assay was shown to be amenable to a dried reagent format.

Example 3

ALT Assay (Absorbance)

This example illustrates results of homogeneous absorbance-based alanine transaminase (ALT) assays expected to be compatible with the Truvian platform.

In brief, 10×PBS and deionized water were purchased from Thermo Fischer Scientific and 2×ALT assay reagent, serum controls, and ALT stock for spiking were provided by Cliniqa Corp. 2×PBS was prepared by diluting the 10×PBS 1:5 with deionized water. Seven different donor plasma samples were thawed, and three were selected for spiking with high concentration ALT stock to simulate samples with high ALT concentration. Sample spiking was performed by creating a 1:20 dilution of the ALT stock and pipetting aliquots into chosen plasma samples. Then, the samples, spiked samples, and serum controls were diluted 1:5.5 in 2×PBS. The 2×ALT assay reagent and a 384-well plate were pre-heated at 37° C. for 10 minutes. Following pre-heating, 20 μL of 2×ALT assay reagent was pipetted into the wells of the 384-well plate, then 24 μL of the diluted samples were pipetted into the reagent-containing wells in triplicate. The plate was then transferred to a Molecular Devices Spectramax M2 set to 37° C., shaken for 30 seconds, then the absorbance of each well at 340 nm was collected every 30 seconds for 30 minutes, with 3 second shakes between each absorbance measurement. ALT values were calculated by identifying the longest time interval in which the decrease in absorbance at 340 nm occurred at a constant rate, then using the slope of this decrease in absorbance vs. time to calculate the ALT activity. The calculated ALT values were compared against those evaluated using the Colorimetric ALT assay kit, purchased from Bioassay Systems, LLC (Hayward, CA). FIG. 23 shows a graph illustrating an exemplary ALT assay standard curve obtained using a Truvian-compatible colorimetric assay format or a Bioassay Systems comparator assay. The Truvian-compatible and comparator assay results were found to correlate well (correlation coefficient=0.981).

Table 6 shows comparative results of exemplary ALT assays performed in blood donor samples that were obtained using the Truvian-compatible absorbance assay versus a comparator assay run on a Piccolo Xpress system. Generally, ALT assay results obtained with the Truvian-compatible assay were found to fall within 15% of comparator readings.

TABLE 6

ALT Assay Results for Blood Donor Samples

| Sample | Nominal [U/L] | Truvian [U/L] | Percent Error |
|---|---|---|---|
| HD90 | 41.0 | 41.6 | 1.4% |
| HD91 | 84.0 | 75.2 | −10.5% |
| HD92 | 42.0 | 43.2 | 3.0% |
| S90 | 141.7 | 138.6 | −2.2% |
| S92 | 140.9 | 159.8 | 13.4% |
| S93 | 200.1 | 200.1 | 0.0% |
| HD94 | 40.0 | 35.2 | −12.0% |
| HD95 | 24.0 | 24.0 | 0.0% |
| HD96 | 18.0 | 17.4 | −3.3% |
| HD97 | 56.0 | 55.5 | −0.9% |

Example 4

Heterogeneous Assays

This example illustrates results of a heterogeneous immuno-assay for quantifying C-reactive protein (CRP), which is believed to be compatible with the Truvian system (cartridge and AMU).

CRP was detected using a fluorescence-linked immunosorbent assay format. CRP capture antibodies were bound to beads. The beads were dispensed into wells of a microtiter plate and incubated with a serial dilution of CRP standards. A fluorescence-labelled secondary anti-CRP antibody was added to the wells containing bead-bound CRP capture antibodies and CRP standards. Bead associated fluorescence was detected using a Truvian AMU and quantified using Truvian image analysis software. The assay was performed in a mix-and-read format, without washing steps.

FIG. 24A shows a CRP standard curve obtained in an exemplary CRP sandwich FLISA. FIG. 24B illustrates the detection of bead associated fluorescence detected as part of a CRP sandwich FLISA over low bulk fluorescence background signals.

Example 5

Cellular Assays

This example illustrates results of a fluorescence-based cellular assay detecting CD4-expressing cells, which is believed to be compatible with the Truvian system (cartridge and AMU).

A sample containing CD4-expressing cells was incubated in the well of a microtiter plate in the presence of a fluorescence labeled anti-CD4 antibody. Cell-associated fluorescence was quantified using a Truvian AMU and Truvian image analysis software. The cellular assay was performed in a mix-and-read format without a washing step. The samples were analyzed for CD4 cell content using a Truvian system and a standard FACS comparator assay.

FIG. 25A and FIG. 25B show results of an accuracy experiment comparing the CD4 cell content of a sample as determined using a Truvian AMU and a standard FACS comparator assay. Table 7 shows the results of linear regression analyses related to FIG. 25A and FIG. 25B.

TABLE 7

Cell Based Assays: CD4 Accuracy Study

| Parameter | Coefficient | Standard error | 95% CI |
|---|---|---|---|
| Regression Equation for CD4 counts: Y = 22.78 + 0.96 X | | | |
| Slope | 0.96 | 0.01 | 0.94 to 0.98 |
| Intercept | 22.78 | 7.81 | 7.37 to 38.18 |
| Regression Equation for % CD4 values: Y = 0.72 + 1.07 X | | | |
| Slope | 1.07 | 0.02 | 1.03 to 1.11 |
| Intercept | 0.72 | 0.65 | −0.56 to 1.99 |

What is claimed is:

1. A method of performing point-of-care assays for a plurality of analytes in a liquid sample, the method being performed within a single diagnostic system, the method comprising:

A. providing a multiwell plate comprising a plurality of wells, each well containing a portion of the liquid sample, the multiwell plate having a translucent bottom and opaque well walls wherein:

i) a first well contains a first reagent comprising a fluorogenic substrate or a fluorescently labeled binding protein configured to emit a fluorescent signal upon interaction with a first analyte in the sample; and ii) a second well contains a second reagent comprising a chromogenic substrate configured to produce a detectable absorbance change upon interaction with a second analyte in the sample;

a single light source;

a single CMOS;

a motor;

a platform configured to receive the multiwell plate, the platform comprises platform magnets, platform vertical keys and an opaque film wherein the opaque film is disposed on an upper surface of the platform;

wherein a peripheral portion of the multiwell plate comprising a plurality of overhang wells including the first well and the second well, overhangs the platform and a selected overhang well from the plurality of overhang wells is within an optical path of the light source and CMOS and is aligned to permit transmission of light through the translucent bottom of the first overhang well without obstruction from the platform or the motor;

the platform vertical keys engaged with a seat by a seat vertical key and platform magnets engaged with the seat by seat magnets in the seat, the seat coupled to the motor; and a processor operatively connected to the CMOS;

B. moving, under control of the motor, the multiwell plate relative to the single CMOS and single light source, such that the first well of the plurality of overhang wells is aligned with the CMOS and the light source;

C. directing light from the single light source to the translucent bottom of the first well of the plurality of overhang wells and detecting by the CMOS a fluorescence emission generated upon interaction between a first analyte in the sample and the first reagent;

D. moving, under control of the motor, the multiwell plate relative to the single CMOS and single light source, such that the second well of the plurality of overhang wells is aligned with the CMOS and the light source;

E. directing light from the single light source to the translucent bottom of the second well of the plurality of overhang wells and detecting by the CMOS transmitted or absorbed light generated upon interaction between a second analyte in the sample and the second reagent;

F. processing, by the processor, (i) the detected fluorescence emission from the CMOS to generate analyte measurements for the first analyte in the liquid sample and (ii) the transmitted or absorbed light detected from the CMOS to generate analyte measurements for the second analyte in the liquid sample.

* * * * *